United States Patent
Price et al.

(10) Patent No.: US 11,359,210 B2
(45) Date of Patent: Jun. 14, 2022

(54) INIR12 TRANSGENIC MAIZE

(71) Applicant: INARI AGRICULTURE TECHNOLOGY, INC., Cambridge, MA (US)

(72) Inventors: Joshua L. Price, Cambridge, MA (US); Michael Andreas Kock, Rheinfelden (DE); Michael Lee Nuccio, Salem, NH (US); Frédéric Van Ex, Kortrijk (BE); Alexandra Elata, Arlington, MA (US); Daniel Rodriguez Leal, Belmont, MA (US)

(73) Assignee: Inari Agriculture Technology, Inc., Cambridge, MA (US)

( * ) Notice: Subject to any disclaimer, the term of this patent is extended or adjusted under 35 U.S.C. 154(b) by 0 days.

(21) Appl. No.: 17/248,936

(22) Filed: Feb. 12, 2021

(65) Prior Publication Data

US 2022/0033842 A1 Feb. 3, 2022

Related U.S. Application Data

(60) Provisional application No. 63/199,949, filed on Feb. 4, 2021, provisional application No. 63/059,813, filed on Jul. 31, 2020, provisional application No. 63/059,916, filed on Jul. 31, 2020, provisional application No. 63/059,860, filed on Jul. 31, 2020, provisional application No. 63/059,963, filed on Jul. 31, 2020, provisional application No. 63/199,930, filed on Feb. 3, 2021.

(51) Int. Cl.
C12N 15/82 (2006.01)

(52) U.S. Cl.
CPC ..... C12N 15/8286 (2013.01); C12N 15/8213 (2013.01)

(58) Field of Classification Search
CPC ..................... C12N 15/8286; C12N 15/8213
See application file for complete search history.

(56) References Cited

U.S. PATENT DOCUMENTS

| | | | |
|---|---|---|---|
| 8,232,456 B2* | 7/2012 | Long | C12Q 1/6895 800/302 |
| 8,450,561 B2 | 5/2013 | Beazley et al. | |
| 8,455,720 B2 | 6/2013 | Long et al. | |
| 9,187,756 B2 | 11/2015 | Nuccio | |
| 2003/0088081 A1 | 5/2003 | Maliga et al. | |
| 2010/0162428 A1 | 6/2010 | Brown et al. | |
| 2013/0333071 A1 | 12/2013 | Boukharov et al. | |
| 2014/0162272 A1 | 6/2014 | Long et al. | |
| 2014/0196169 A1 | 7/2014 | D'Halluin et al. | |
| 2015/0059010 A1 | 2/2015 | Cigan et al. | |
| 2015/0082478 A1 | 3/2015 | Cigan et al. | |
| 2016/0333363 A1 | 11/2016 | Srivastava | |
| 2019/0352655 A1 | 11/2019 | Niu et al. | |
| 2020/0157554 A1 | 5/2020 | Cigan et al. | |

FOREIGN PATENT DOCUMENTS

| | | |
|---|---|---|
| CN | 104830860 B | 1/2018 |
| WO | 2018111553 A1 | 6/2018 |

OTHER PUBLICATIONS

Ward and Huber (Petition for Determination of Nonregulated Status for Insect-Resistant MIR162 Maize. 1-268, Aug. 31, 2007). (Year: 2007).*
Du et al (Construction of Marker-Free Genetically Modified Maize Using a Heat-Inducible Auto-Excision Vector. Genes. 10, 1-17, May 2019). (Year: 2019).*
Que et al (Maize transformation technology development for commercial event generation. Frontiers in plant science. 5, 1-19, 2004) . (Year: 2004).*
Bortesi et al., "The CRISPR/Cas9 system for plant genome editing and beyond", Biotechnology Advances, vol. 33, pp. 41-52, Dec. 16, 2014.
Cho et al., "Nonallelic homologous recombination events responsible for copy number variation within an RNA silencing locus", Plant Direct, vol. 3, 16 pages, Aug. 5, 2019.
Luo et al., "Improperly Terminated, Unpolyadenylated mRNA of Sense Transgenes is Targeted by RDR6-Mediated RNA Silencing in *Arabidopsis*", The Plant Cell, vol. 19, pp. 943-958, Mar. 2007.
Srivastava et al., "Gene Stacking by recombinases", Plant Biotechnology Journal, vol. 14, pp. 471-482, 2016.
Xing et al., "Revealing frequent alternative polyadenylation and widespread low-level transcription read-through of novel plant transcription terminators", Plant Biotechnology Journal, vol. 8, pp. 772-782, 2010.
Young et al., "CRISPR-Cas9 Editing in Maize: Systematic Evaluation of Off-target Activity and Its Relevance in Crop Improvement", Scientific Reports, vol. 9, 11 pages, Apr. 15, 2019.
Biopesticides Registration Action Document, "Bacillus thuringiensis Vip3Aa20 Insecticidal Protein and the Genetic Material Necessary for Its Production (via Elements of Vector pNOV1300) in Event MIR162 Maize (OECD Unique Identifier: SYN-IR162-4)", PC Code: 006599, Vip3Aa20 Maize, pp. 1-175, Mar. 2009.

(Continued)

*Primary Examiner* — Bratislav Stankovic
*Assistant Examiner* — Wayne Zhong
(74) *Attorney, Agent, or Firm* — McKee, Voorhees & Sease, PLC

(57) ABSTRACT

Transgenic INIR12 maize plants comprising a vip3Aa19 expression cassette linked to a secondary nopaline synthase terminator element which lack a selectable marker gene are provided. In certain embodiments such INIR12 transgenic plants comprise modifications that provide for facile excision of the INIR12 transgenic locus from the maize plant genome. Genomic DNA of INIR12 transgenic plants, detection of INIR12 plants and products thereof, methods of making INIR12 plants, and use of INIR12 plants to facilitate breeding are disclosed.

10 Claims, 21 Drawing Sheets

Figure 1L:
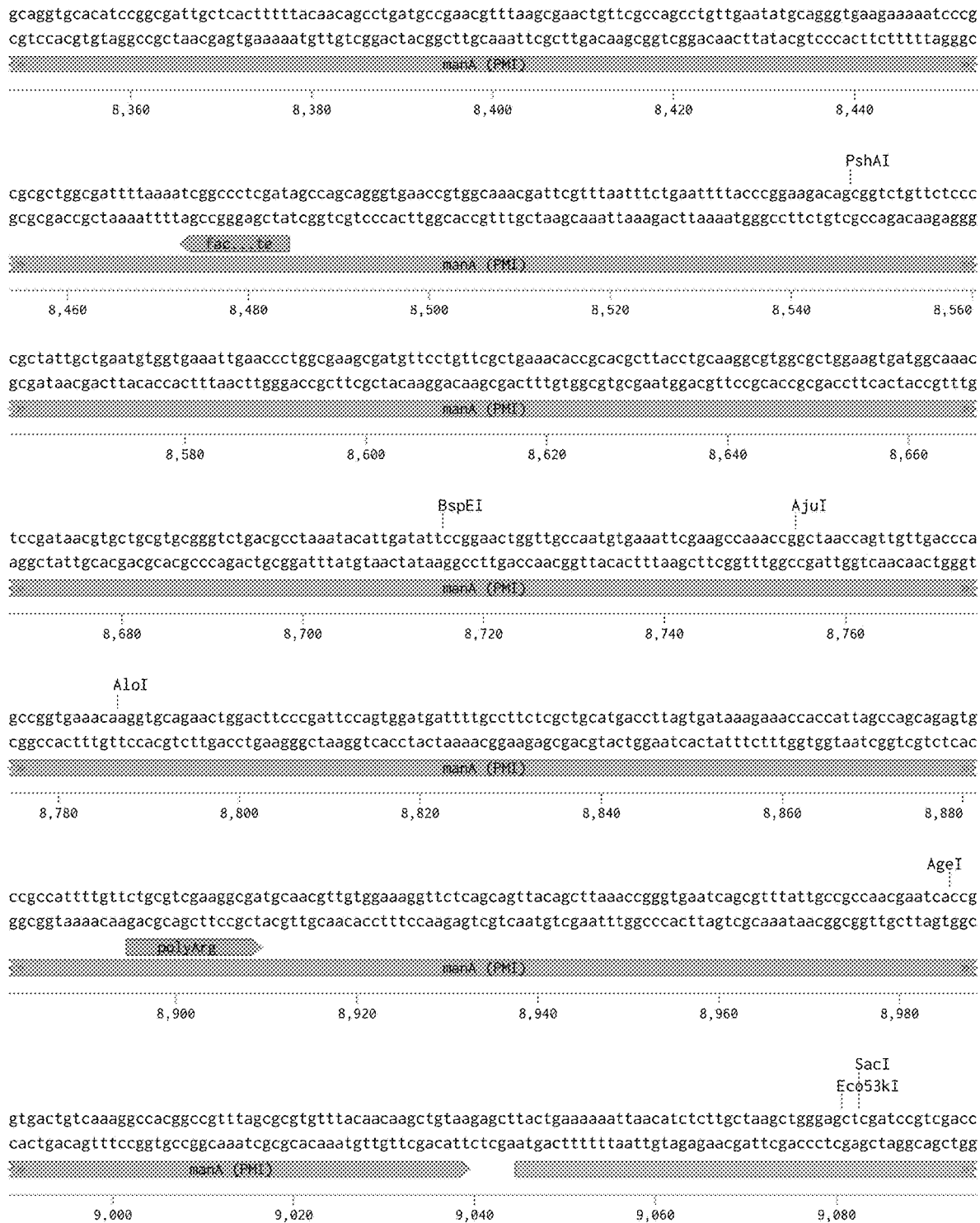
Figure 1M:
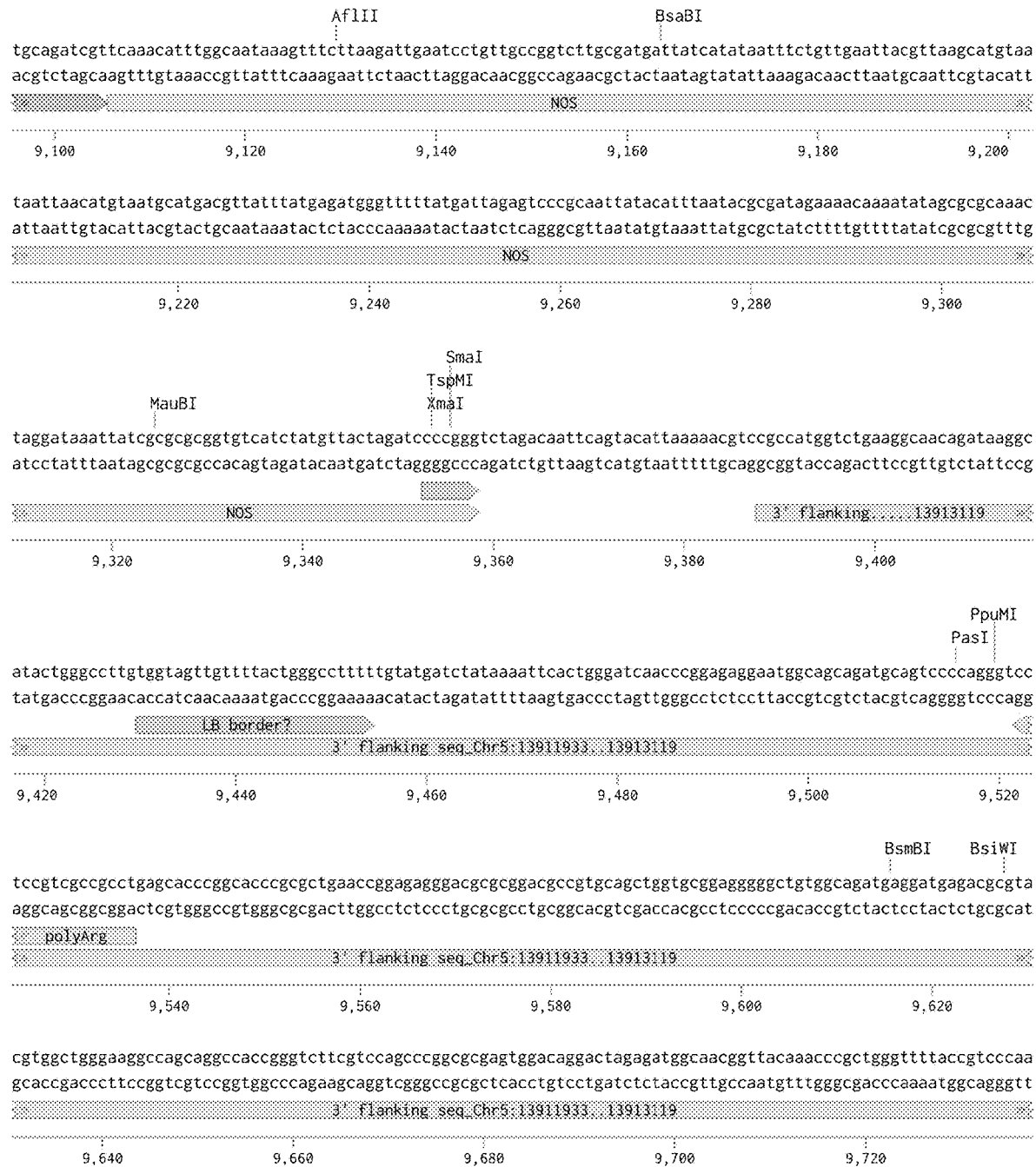
Figure 1N:
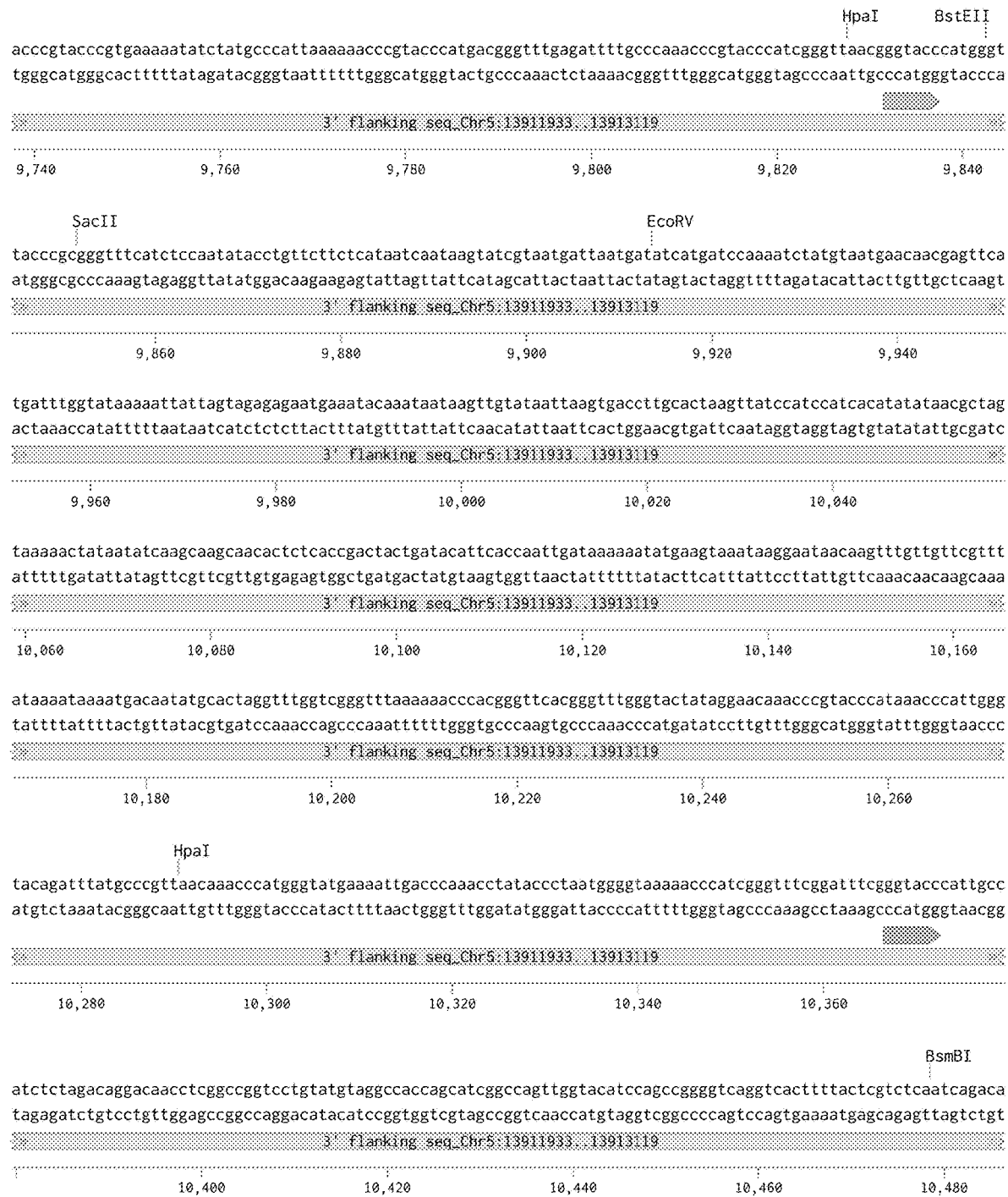

Specification includes a Sequence Listing.

(56) References Cited

OTHER PUBLICATIONS

Du et al., "Infection of Embryonic Callus with Agrobacterium Enables High-Speed Transformation of Maize", International Journal of Molecular Sciences, vol. 20,. No 279, pp. 1-15, doi:10.3390/ijms20020279, 2019.

International Searching Authority in connection with PCT/US2021/043468 filed Jul. 28, 2021, "The International Search Report and the Written Opinion of the International Searching Authority, or the Declaration", 19 pages, dated Nov. 26, 2021.

Du et al., "Construction of Marker-Free Genetically Modified Maize Using a Heat-Inducible Auto-Excision Vector", Genes, vol. 10, No. 374, pp. 1-17, 2019.

Stine, Harry H., "Request for Extension of Determination of Nonregulated Status to the Additional Regulated Article: Maize Line HCEM485", USDA Extension Petition (online), https://www.aphis.usda.gov/brs/aphisdocs/09_06301p_a3.pdf, pp. 1-3, Feb. 14, 2011.

U.S. Department of Agriculture, "BE Corn Crop Summary", USDA Report (online), https://www.ams.usda.gov/sites/defauiUfiles/media/BECornCropSummary.pdf, pp. 1-5, 2018.

International Searching Authority in connection with PCT/US21/43187 filed Jul. 26, 2021, "The International Search Report and the Written Opinion of the International Searching Authority, or the Declaration", 27 pages, dated Jan. 6, 2022.

International Searching Authority in connection with PCT/US21/43161 filed Jul. 26, 2021, The International Search Report and The Written Opinion of the International Searching Authority, or the Declaration, 23 pages, dated Jan. 5, 2022.

U.S. Department of Agriculture, "Approval of AgrEvo Request (98-014-01p) Seeking Extension of Determination of Non-regulated Status for Glufosinate Resistant Soybean Transformation Event A5547-127", 6 pages Apr. 30, 1998.

U.S. Department of Agriculture, "Response to AgrEvo Petition 98-278-01p for Determination of Nonregulated Status for Canola Transformation Events MS8 and RF3 Genetically Engineered for Pollination Control and Tolerance to Glufosinate Herbicide", 4 pages Mar. 22, 1999.

U.S. Department of Agriculture, "Syngenta Petition 03-155-01p for Determination of Nonregulated Status for Lepitodopteran Resistant Cotton Event COT102", 3 pages May 2005.

* cited by examiner

MIR162_US8455720B2 (10579 bp)

```
              PshAI                          SwaI
tcctgtgttgttggaacagacttctgtctcttctggtgatcataaatatttaaatgaaccagttgtgttggaaaatgttgttttcttttgtctctagactggaaagc
aggacacaacaaccttgtctgaagacagagaagaccactagtatttataaatttacttggtcaacacaaccttttacaacaaaagaaaacagagatctgacctttcg
                           genomic_DNA_5'_Chr5:13910790..13911882
          20            40            60            80           100 ggagttctcgtcaacacggttctttcaactagggatgaaagtggtaatccgaattgttagtacaaatttaatattttaaaatagatatgtataaaattttatgttga
cctcaagagcagttgtgccaagaaagttgatccctactttcaccattaggcttaacaatcatgtttaaattataaaattttatctatacatatttaaaatacaact
                           genomic_DNA_5'_Chr5:13910790..13911882
         120           140           160           180           200 tcttttttatgttatcaagcacattagtatataattagtataaatatgaataaaatattacataaaatgttttatgtattatttggtccctacaacataaatagttga
agaaaaaatacaatagttcgtgtaatcatatttaatcatatttatacttattttataatgtattttacaaaatacataataaaccagggatgttgtatttatcaact
                           genomic_DNA_5'_Chr5:13910790..13911882
         220           240           260           280           300           320 aaaaattactaaatttgttttcgaatctatatcgaagtttatatctattatttaagaaaaatataggatgaaaaggtttatcttttatgaatctttacaagctggat
tttttaatgatttaaacaaaagcttagatatagcttcaaatatagataataaattcttttatatcctacttttccaaatagaaaatacttagaaatgttcgaccta
                           genomic_DNA_5'_Chr5:13910790..13911882
         340           360           380           400           420 cttataaacaagaaaataaatttatattgtagattttatatcctatttattcgcaatcaaagaaaagcgactaaaaaactgattaccgagtaaatactgtttccaac
gaatatttgttcttttattttaaatataacatctaaaatataggatgaataagcgttagtttcttttcgctgattttttgactaatggctcatttatgacaaaggttg
                           genomic_DNA_5'_Chr5:13910790..13911882
         440           460           480           500           520 cgtttcgtcccctactatcaacgccttctcccaaccgcagtcgatctgtccgtctgtatcaggcgcagcggcaccctgctgttcgactatctagaccatagaatat
gcaaaagcagggatgatagttgcggaagagggttggcgtcagctagacaggcagacatagtccgcgtcgccgtggggacgacaagctgatagatctggtatcttata
                           genomic_DNA_5'_Chr5:13910790..13911882
         540           560           580           600           620           640

BsmI
tttaggtatacaataattttagttccacgctagaacattttagttagaataataacaagatttgctattgatgtaggactcgcccgtcactgtctaaaaaagcattc
aaatccatatgttattaaaatcaaggtgcgatcttgtaaaatcaatcttattattgttctaaacgataactacatcctgagcgggcagtgacagatttttcgtaag
                           genomic_DNA_5'_Chr5:13910790..13911882
         660           680           700           720           740 tgtcggtcttattcttttaggcatcagcgggtgtactatctcattttccctatcatattcctcagtactctgttaagtataaatggtctattttacatgatgaactaa
acagccagaataagaaatccgtagtcgcccacatgatagagtaaaaaggatagtataaggagtcatgagacaattcatatttaccagataaaatgtactacttgatt
                           genomic_DNA_5'_Chr5:13910790..13911882
         760           780           800           820           840
```

FIGURE 1A

SnaBI taaaactaattaaggatcctaacttttttgtgaaggtaatttggatcattatgcattaccatcctacgtatacctgctgcagcagcatctgcgtaagcacagcctaga
attttgattaattcctaggattgaaaaacacttccattaaacctagtaatacgtaatggtaggatgcatatggacgacgtcgtcgtagacgcattcgtgtcggatct genomic_DNA_5_Chr5:13910790..13911882

860        880        900        920        940        960 tatatgcttctgtgtggactgaaaggagactttgtttatcaattagtatactcccaaaaaactgatgacaccaatgatgcaaataggctgggaatagtctgtctaat
atatacgaagacacacctgactttcctctgaaacaaatagttaatcatatgagggttttttgactactgtggttactacgtttatccgacccttatcagacagatta genomic_DNA_5_Chr5:13910790..13911882

980        1,000        1,020        1,040        1,060

PmeI agtttgagtgaatcatgtcactgatagtttaaactgaaggcgggaaacgacaatctgatcatgagcggagaattaagggagtcacgttatgaccccccgccgatgacg
tcaaactcacttagtacagtgactatcaaatttgacttccgccctttgctgttagactagtactcgcctcttaattccctcagtgcaatactgggggcggctactgc genomic ... 3911882

1,080        1,100        1,120        1,140        1,160

HindIII cgggacaagccgttttacgtttggaactgacagaaccgcaacgttgaaggagccactcagcaagctggtacaagcttgcatgcctgcagtgcagcgtgacccggtcg
gccctgttcggcaaaatgcaaaccttgactgtcttggcgttgcaacttcctcggtgagtcgttcgaccatgttcgaacgtacggacgtcacgtcgcactgggccagc ZmUbiInt 1,180        1,200        1,220        1,240        1,260        1,280 tgcccctctctagagataatgagcattgcatgtctaagttataaaaaattaccacatatttttttgtcacacttgtttgaagtgcagtttatctatctttatacat
acggggagagatctctattactcgtaacgtacagattcaatattttttaatggtgtataaaaaaaacagtgtgaacaaacttcacgtcaaatagatagaaatatgta ZmUbiInt 1,300        1,320        1,340        1,360        1,380 atatttaaactttactctacgaataatataatctatagtactacaataatatcagtgttttagagaatcatataaatgaacagttagacatggtctaaaggacaatt
tataaatttgaaatgagatgcttattatattagatatcatgatgttattatagtcacaaaatctcttagtatatttacttgtcaatctgtaccagatttcctgttaa ZmUbiInt 1,400        1,420        1,440        1,460        1,480 gagtattttgacaacaggactctacagttttatcttttttagtgtgcatgtgttctccttttttttttgcaaatagcttcacctatataatacttcatccatttt atta
ctcataaaactgttgtcctgagatgtcaaaatagaaaaatcacacgtacacaagaggaaaaaaaaacgtttatcgaagtggatatattatgaagtaggtaaaataat ZmUbiInt 1,500        1,520        1,540        1,560        1,580        1,600

FIGURE 1B

```
gtacatccatttagggtttagggttaatggttttttatagactaatttttttagtacatctattttattctattttagcctctaaattaagaaaactaaaactctatt
catgtaggtaaatcccaaatcccaattaccaaaaatatctgattaaaaaaatcatgtagataaaataagataaaatcggagatttaattcttttgattttgagataa
                                                ZmUbiInt
          1,620          1,640          1,660          1,680          1,700 ttagtttttttatttaataatttagatataaaatagaataaaataaagtgactaaaaattaaacaaatacccttttaagaaattaaaaaaactaaggaaacattttc
aatcaaaaaaataaattattaaatctatattttatcttattttatttcactgattttaatttgtttatgggaaattctttaattttttttgattcctttgtaaaaag
                                                ZmUbiInt
          1,720          1,740          1,760          1,780          1,800

SgrDI
ttgtttcgagtagataatgccagcctgttaaacgccgtcgacgagtctaacggacaccaaccagcgaaccagcagcgtcgcgtcgggccaagcgaagcagacggcac
aacaaagctcatctattacggtcggacaattgcggcagctgctcagattgcctgtggttggtcgcttggtcgtcgcagcgcagcccggttcgcttcgtctgccgtg
                                               polyArg
                                                ZmUbiInt
                                   polyArg
          1,820          1,840          1,860          1,880          1,900          1,920

PaeR7I
                                  XhoI
                                  PliI
ggcatctctgtcgctgcctctggaccccctctcgagagttccgctccaccgttggacttgctccgctgtcggcatccagaaattgcgtggcggagcggcagacgtgag
ccgtagagacagcgacggagacctggggagagctctcaaggcgaggtggcaacctgaacgaggcgacagccgtaggtctttaacgcaccgcctcgccgtctgcactc
                                                ZmUbiInt
          1,940          1,960          1,980          2,000          2,020

NaeI
  NgoMIV
ccggcacggcaggcggcctcctcctcctctcacggcaccggcagctacgggggattcctttcccaccgctccttcgctttcccttcctcgcccgccgtaataaatag
ggccgtgccgtccgccggaggaggaggagagtgccgtggccgtcgatgcccctaaggaaagggtggcgaggaagcgaagggaaggagcgggcggcattatttatc
                                                ZmUbiInt
              polyArg
          2,040          2,060          2,080          2,100          2,120          2,140 acacccctccacaccctctttccccaacctcgtgttgttcggagcgcacacacacacaaccagatctcccccaaatccaccccgtcggcacctccgcttcaaggtac
tgtggggagtgtgggagaaagggttggagcacaacaagcctcgcgtgtgtgtgttggtctagagggggttaggtgggcagccgtggaggcgaagttccatg
                                                ZmUbiInt
          2,160          2,180          2,200          2,220          2,240
```

FIGURE 1C

```
                                                              ApaI
                                                              PspOMI
gccgctcgtcctccccccccccccctctctaccttctctagatcggcgttccggtccatggttagggcccggtagttctacttctgttcatgtttgtgttagatccg
cggcgagcaggaggggggggggggagagatggaagagatctagccgcaaggccaggtaccaatcccgggccatcaagatgaagacaagtacaaacacaatctaggc
                                              ZmUbiInt 2,260          2,280          2,300          2,320          2,340 tgtttgtgttagatccgtgctgctagcgttcgtacacggatgcgacctgtacgtcagacacgttctgattgctaacttgccagtgtttctctttggggaatcctggg
acaaacacaatctaggcacgacgatcgcaagcatgtgcctacgctggacatgcagtctgtgcaagactaacgattgaacggtcacaaagagaaacccccttaggaccc
                                              ZmUbiInt 2,360         2,380          2,400          2,420          2,440          2,460 atggctctagccgttccgcagacgggatcgatttcatgattttttttgtttcgttgcataggggtttggtttgccctttttcctttatttcaatatatgccgtgcactt
taccgagatcggcaaggcgtctgccctagctaaagtactaaaaaaaacaaagcaacgtatcccaaaccaaacgggaaaaggaaataaagttatatacggcacgtgaa
                                              ZmUbiInt 2,480          2,500          2,520          2,540          2,560

EcoRI
gtttgtcgggtcatcttttcatgctttttttttgtcttggttgtgatgatgtggtctggttgggcggtcgttctagatcggagtagaattctgtttcaaactacctgg
caaacagcccagtagaaaagtacgaaaaaaaacagaaccaacactactacaccagaccaacccgccagcaagatctagcctcatcttaagacaaagtttgatggacc
                                              ZmUbiInt 2,580          2,600          2,620          2,640          2,660 tggatttattaattttggatctgtatgtgtgtgccatacatattcatagttacgaattgaagatgatggatggaaatatcgatctaggataggtatacatgttgatg
acctaaataattaaaacctagacatacacacacggtatgtataagtatcaatgcttaacttctactacctacctttatagctagatcctatccatatgtacaactac
                                              ZmUbiInt 2,680          2,700          2,720          2,740          2,760          2,780 cggggttttactgatgcatatacagagatgcttttgttcgcttggttgtgatgatgtggtgtggttgggcggtcgttcattcgttctagatcggagtagaatactgt
gcccaaaatgactacgtatatgtctctacgaaaaacaagcgaaccaacactactacaccacaccaacccgccagcaagtaagcaagatctagcctcatcttatgaca
                                              ZmUbiInt
                                                    Universal 2,800          2,820          2,840          2,860          2,880 ttcaaactacctggtgtatttattaattttggaactgtatgtgtgtgtcatacatcttcatagttacgagtttaagatggatggaaatatcgatctaggataggtat
aagtttgatggaccacataaataattaaaaccttgacatacacacacagtatgtagaagtatcaatgctcaaattctacctaccttttatagctagatcctatccata
                                              ZmUbiInt 2,900          2,920          2,940          2,960          2,980 acatgttgatgtgggttttactgatgcatatacatgatggcatatgcagcatctattcatatgctctaaccttgagtacctatctattataataaacaagtatgttt
tgtacaactacacccaaaatgactacgtatatgtactaccgtatacgtcgtagataagtatacgagattggaactcatggatagataatattatttgttcatacaaa
                                              ZmUbiInt 3,000          3,020          3,040          3,060          3,080          3,100
```

FIGURE 1D tataattattttgatcttgatatacttggatgatggcatatgcagcagctatatgtggattttttagccctgccttcatacgctatttatttgcttggtactgttt
atattaataaaactagaactatatgaacctactaccgtatacgtcgtcgatatacacctaaaaaaatcgggacggaagtatgcgataaataaacgaaccatgacaaa ZmUbiInt 3,120   3,140   3,160   3,180   3,200 cttttgtcgatgctcaccctgttgtttggtgttacttctgcaggtcgactctagaggatccaccatgaacaagaacaacaccaagctgagcacccgcgccctgccga
gaaaacagctacgagtgggacaacaaaccacaatgaagacgtccagctgagatctcctaggtggtacttgttcttgttgtggttcgactcgtgggcgcgggacggct ZmUbiInt                                                    vip3Aa19

3,220   3,240   3,260   3,280   3,300 gcttcatcgactacttcaacggcatctacggcttcgccaccggcatcaaggacatcatgaacatgatcttcaagaccgacaccggcggcgacctgaccctggacgag
cgaagtagctgatgaagttgccgtagatgccgaagcggtggccgtagttcctgtagtacttgtactagaagttctggctgtggccgccgctggactgggacctgctc vip3Aa19

3,320   3,340   3,360   3,380   3,400   3,420

PasI
atcctgaagaaccagcagctgctgaacgacatcagcggcaagctggacggcgtgaacggcagcctgaacgacctgatcgcccagggcaacctgaacaccgagctgag
taggacttcttggtcgtcgacgacttgctgtagtcgccgttcgacctgccgcacttgccgtcggacttgctggactagcgggtcccgttggacttgtggctcgactc vip3Aa19

3,440   3,460   3,480   3,500   3,520

AflII
caaggagatccttaagatcgccaacgagcagaaccaggtgctgaacgacgtgaacaacaagctggacgccatcaacaccatgctgcgcgtgtacctgccgaagatca
gttcctctaggaattctagcggttgctcgtcttggtccacgacttgctgcacttgttgttcgacctgcggtagttgtggtacgacgcgcacatggacggcttctagt vip3Aa19

3,540   3,560   3,580   3,600   3,620 ccagcatgctgagcgacgtgatgaagcagaactacgccctgagcctgcagatcgagtacctgagcaagcagctgcaggagatcagcgacaagctggacatcatcaac
ggtcgtacgactcgctgcactacttcgtcttgatgcgggactcggacgtctagctcatggactcgttcgtcgacgtcctctagtcgctgttcgacctgtagtagttg vip3Aa19

3,640   3,660   3,680   3,700   3,720   3,740 gtgaacgtcctgatcaacagcaccctgaccgagatcaccccggcctaccagcgcatcaagtacgtgaacgagaagttcgaagagctgaccttcgccaccgagaccag
cacttgcaggactagttgtcgtgggactggctctagtggggccggatggtcgcgtagttcatgcacttgctcttcaagcttctcgactggaagcggtggctctggtc vip3Aa19

3,760   3,780   3,800   3,820   3,840

FIGURE 1E

```
                                              PfoI
cagcaaggtgaagaaggacggcagcccggccgacatcctggacgagctgaccgagctgaccgagctggcgaagagcgtgaccaagaacgacgtggacggcttcgagt
gtcgttccacttcttcctgccgtcgggccggctgtaggacctgctcgactggctcgactggctcgaccgcttctcgcactggttcttgctgcacctgccgaagctca
                                                        vip3Aa19

3,860              3,880             3,900             3,920             3,940

XmnI
tctacctgaacaccttccacgacgtgatggtgggcaacaacctgttcggccgcagcgccctgaagaccgccagcgagctgatcaccaaggagaacgtgaagaccagc
agatggacttgtggaaggtgctgcactaccacccgttgttggacaagccggcgtcgcgggacttctggcggtcgctcgactagtggttcctcttgcacttctggtcg
                                                        vip3Aa19

3,960            3,980            4,000            4,020            4,040            4,060

BsrGI                               SbfI      StuI             AhdI
ggcagcgaggtgggcaacgtgtacaacttcctgatcgtgctgaccgccctgcaggcccaggccttcctgaccctgaccacctgtcgcaagctgctgggcctggccga
ccgtcgctccacccgttgcacatgttgaaggactagcacgactggcgggacgtccgggtccggaaggactgggactggtggacagcgttcgacgacccggaccggct
                                                        vip3Aa19

4,080             4,100             4,120             4,140             4,160 catcgactacaccagcatcatgaacgagcacttgaacaaggagaaggaggagttccgcgtgaacatcctgccgaccctgagcaacaccttcagcaacccgaactacg
gtagctgatgtggtcgtagtacttgctcgtgaacttgttcctcttcctcctcaaggcgcacttgtaggacggctgggactcgttgtggaagtcgttgggcttgatgc
                                       polyArg
                                                        vip3Aa19

4,180             4,200             4,220             4,240             4,260             4,280 ccaaggtgaagggcagcgacgaggacgccaagatgatcgtggaggctaagccgggccacgcgttgatcggcttcgagatcagcaacgacagcatcaccgtgctgaag
ggttccacttcccgtcgctgctcctgcggttctactagcacctccgattcggcccggtgcgcaactagccgaagctctagtcgttgctgtcgtagtggcacgacttc
                                                        vip3Aa19

4,300            4,320            4,340            4,360            4,380

BspEI
gtgtacgaggccaagctgaagcagaactaccaggtggacaaggacagcttgagcgaggtgatctacggcgacatggacaagctgctgtgtccggaccagagcgagca
cacatgctccggttcgacttcgtcttgatggtccacctgttcctgtcgaactcgctccactagatgccgctgtacctgttcgacgacacaggcctggtctcgctcgt
                                                        vip3Aa19

4,400             4,420             4,440             4,460             4,480

AjuI            BstEII
aatctactacaccaacaacatcgtgttcccgaacgagtacgtgatcaccaagatcgacttcaccaagaagatgaagaccctgcgctacgaggtgaccgccaacttct
ttagatgatgtggttgttgtagcacaagggcttgctcatgcactagtggttctagctgaagtggttcttctacttctgggacgcgatgctccactggcggttgaaga
                                                        vip3Aa19

4,500             4,520            4,540             4,560             4,580             4,600
```

FIGURE 1F

```
acgacagcagcaccggcgagatcgacctgaacaagaagaaggtggagagcagcgaggccgagtaccgcaccctgagcgcgaacgacgacggcgtctacatgccactg
tgctgtcgtcgtggccgctctagctggacttgttcttcttccacctctcgtcgctccggctcatggcgtgggactcgcgcttgctgctgccgcagatgtacggtgac
```
polyArg
polyArg
vip3Aa19

4,620  4,640  4,660  4,680  4,700

SbfI
```
ggcgtgatcagcgagaccttcctgaccccgatcaacggctttggcctgcaggccgacgagaacagccgcctgatcaccctgacctgtaagagctacctgcgcgagct
ccgcactagtcgctctggaaggactggggctagttgccgaaaccggacgtccggctgctcttgtcggcggactagtgggactggacattctcgatggacgcgctcga
```
vip3Aa19

4,720  4,740  4,760  4,780  4,800

```
gctgctagccaccgacctgagcaacaaggagaccaagctgatcgtgccaccgagcggcttcatcagcaacatcgtggagaacggcagcatcgaggaggacaacctgg
cgacgatcggtggctggactcgttgttcctctggttcgactagcacggtggctcgccgaagtagtcgttgtagcacctcttgccgtcgtagctcctcctgttggacc
```
vip3Aa19

4,820  4,840  4,860  4,880  4,900  4,920

```
agccgtggaaggccaacaacaagaacgcctacgtggaccacaccggcggcgtgaacggcaccaaggccctgtacgtgcacaaggacggcggcatcagccagttcatc
tcggcaccttccggttgttgttcttgcggatgcacctggtgtggccgccgcacttgccgtggttccgggacatgcacgtgttcctgccgccgtagtcggtcaagtag
```
vip3Aa19

4,940  4,960  4,980  5,000  5,020

PsrI
```
ggcgacaagctgaagccgaagaccgagtacgtgatccagtacaccgtgaagggcaagccatcgattcacctgaaggacgagaacaccggctacatccactacgagga
ccgctgttcgacttcggcttctggctcatgcactaggtcatgtggcacttcccgttcggtagctaagtggacttcctgctcttgtggccgatgtaggtgatgctcct
```
vip3Aa19

5,040  5,060  5,080  5,100  5,120

AfeI
```
caccaacaacaacctggaggactaccagaccatcaacaagcgcttcaccaccggcaccgacctgaagggcgtgtacctgatcctgaagagccagaacggcgacgagg
gtggttgttgttggacctcctgatggtctggtagttgttcgcgaagtggtggccgtggctggacttcccgcacatggactaggacttctcggtcttgccgctgctcc
```
vip3Aa19

5,140  5,160  5,180  5,200  5,220  5,240

StuI   PfoI                                            PflMI
```
cctggggcgacaacttcatcatcctggagatcagcccgagcgagaagctgctgagcccggagctgatcaacaccaacaactggaccagcaccggcagcaccaacatc
ggaccccgctgttgaagtagtaggacctctagtcgggctcgctcttcgacgactcgggcctcgactagttgtggttgttgacctggtcgtggccgtcgtggttgtag
```
HQ
HQ
vip3Aa19

```
tttaaactttactctacgaataatataatctatagtactacaataatatcagtgttttagagaatcatataaatgaacagttagacatggtctaaaggacaattgag
aaatttgaaatgagatgcttattatattagatatcatgatgttattatagtcacaaaatctcttagtatatttacttgtcaatctgtaccagatttcctgttaactc
```
ZmUbiInt 6,000   6,020   6,040   6,060   6,080

```
tattttgacaacaggactctacagtttttatcttttttagtgtgcatgtgttctcctttttttttgcaaatagcttcacctatataatacttcatccatttttattagta
ataaaactgttgtcctgagatgtcaaaatagaaaaatcacacgtacacaagaggaaaaaaaaacgtttatcgaagtggatatattatgaagtaggtaaaataatcat
```
ZmUbiInt 6,100   6,120   6,140   6,160   6,180   6,200

```
catccatttagggtttagggttaatggttttttatagactaatttttttagtacatctattttattctatttttagcctctaaattaagaaaactaaaactctatttta
gtaggtaaatcccaaatcccaattaccaaaaatatctgattaaaaaaatcatgtagataaaataagataaaatcggagatttaattcttttgattttgagataaaat
```
ZmUbiInt 6,220   6,240   6,260   6,280   6,300

```
gttttttttatttaataatttagatataaaatagaataaaataaagtgactaaaaattaaacaaatacccttttaagaaattaaaaaaaactaaggaaacatttttcttg
caaaaaaataaattattaaatctatattttatcttattttatttcactgattttttaatttgtttatgggaaattctttaattttttttgattcctttgtaaaaagaac
```
ZmUbiInt 6,320   6,340   6,360   6,380   6,400   6,420

SgrDI
```
tttcgagtagataatgccagcctgttaaacgccgtcgacgagtctaacggacaccaaccagcgaaccagcagcgtcgcgtcgggccaagcgaagcagacggcacggc
aaagctcatctattacggtcggacaatttgcggcagctgctcagattgcctgtggttggtcgcttggtcgtcgcagcgcagcccggttcgcttcgtctgccgtgccg
```
polyArg
polyArg
ZmUbiInt 6,440   6,460   6,480   6,500   6,520

PaeR7I
         XhoI
         PliI                                                                                      NaeI
                                                                                                   NgoMIV
```
atctctgtcgctgcctctggaccccctctcgagagttccgctccaccgttggacttgctccgctgtcggcatccagaaattgcgtggcggagcggcagacgtgagccg
tagagacagcgacggagacctggggagagctctcaaggcgaggtggcaacctgaacgaggcgacagccgtaggtctttaacgcaccgcctcgccgtctgcactcggc
```
ZmUbiInt 6,540   6,560   6,580   6,600   6,620

```
gcacggcaggcggcctcctcctcctctcacggcaccggcagctacgggggattcctttcccaccgctccttcgctttcccttcctcgcccgccgtaataaatagaca
cgtgccgtccgccggaggaggaggagagtgccgtggccgtcgatgcccccctaaggaaagggtggcgaggaagcgaaagggaaggagcgggcggcattatttatctgt
```
polyArg
ZmUbiInt 6,640   6,660   6,680   6,700   6,720   6,740

FIGURE 1I ccccctccacaccctctttccccaacctcgtgttgttcggagcgcacacacacacaaccagatctcccccaaatccacccgtcggcacctccgcttcaaggtacgcc
gggggaggtgtgggagaaagggggttggagcacaacaagcctcgcgtgtgtgtgtgttggtctagagggggtttaggtgggcagccgtggaggcgaagttccatgcgg 6,760             6,780             6,800             6,820             6,840

ApaI
PspOMI
gctcgtcctcccccccccccccctctctaccttctctagatcggcgttccggtccatggttagggcccggtagttctacttctgttcatgtttgtgttagatccgtgt
cgagcaggaggggggggggggggagagatggaagagatctagccgcaaggccaggtaccaatcccgggccatcaagatgaagacaagtacaaacacaatctaggcaca 6,860             6,880             6,900             6,920             6,940 ttgtgttagatccgtgctgctagcgttcgtacacggatgcgacctgtacgtcagacacgttctgattgctaacttgccagtgtttctctttggggaatcctgggatg
aacacaatctaggcacgacgatcgcaagcatgtgcctacgctggacatgcagtctgtgcaagactaacgattgaacggtcacaaagagaaaccccttaggaccctac 6,960             6,980             7,000             7,020             7,040             7,060 gctctagccgttccgcagacgggatcgatttcatgattttttttgtttcgttgcatagggtttggtttgccctttttcctttatttcaatatatgccgtgcacttgtt
cgagatcggcaaggcgtctgccctagctaaagtactaaaaaaaacaaagcaacgtatcccaaaccaaacgggaaaaggaaataaagttatatacggcacgtgaacaa 7,080             7,100             7,120             7,140             7,160

EcoRI
tgtcgggtcatcttttcatgcttttttttgtcttggttgtgatgatgtggtctggttgggcggtcgttctagatcggagtagaattctgtttcaaactacctggtgg
acagcccagtagaaaagtacgaaaaaaaacagaaccaacactactacaccagaccaacccgccagcaagatctagcctcatcttaagacaaagtttgatggaccacc 7,180             7,200             7,220             7,240             7,260 atttattaattttggatctgtatgtgtgtgccatacatattcatagttacgaattgaagatgatggatggaaatatcgatctaggataggtatacatgttgatgcgg
taaataattaaaacctagacatacacacacggtatgtataagtatcaatgcttaacttctactacctaccttatagctagatcctatccatatgtacaactacgcc 7,280             7,300             7,320             7,340             7,360             7,380 gttttactgatgcatatacagagatgcttttgttcgcttggttgtgatgatgtggtgtggttgggcggtcgttcattcgttctagatcggagtagaatactgtttc
caaaatgactacgtatatgtctctacgaaaaacaagcgaaccaacactactacaccacaccaacccgccagcaagtaagcaagatctagcctcatcttatgacaaag 7,400             7,420             7,440             7,460             7,480 aaactacctggtgtatttattaattttggaactgtatgtgtgtgtcatacatcttcatagttacgagtttaagatggatggaaatatcgatctaggataggtataca
tttgatggaccacataaataattaaaaccttgacatacacacacagtatgtagaagtatcaatgctcaaattctacctaccttatagctagatcctatccatatgt 7,500             7,520             7,540             7,560             7,580

FIGURE 1J

```
tgttgatgtgggttttactgatgcatatacatgatggcatatgcagcatctattcatatgctctaaccttgagtacctatctattataataaacaagtatgttttat
acaactacacccaaaatgactacgtatatgtactaccgtatacgtcgtagataagtatacgagattggaactcatggatagataatattatttgttcatacaaaata
                                            ZmUbiInt
7,600          7,620          7,640          7,660          7,680          7,700 aattattttgatcttgatatacttggatgatggcatatgcagcagctatatgtggattttttttagccctgccttcatacgctatttatttgcttggtactgtttctt
ttaataaaactagaactatatgaacctactaccgtatacgtcgtcgatatacacctaaaaaaatcgggacggaagtatgcgataaataaacgaaccatgacaaagaa
                                            ZmUbiInt
7,720          7,740          7,760          7,780          7,800 ttgtcgatgctcaccctgttgtttggtgttacttctgcagggatccccgatcatgcaaaaactcattaactcagtgcaaaactatgcctggggcagcaaaacggcgt
aacagctacgagtgggacaacaaaccacaatgaagacgtccctaggggctagtacgttttttgagtaattgagtcacgttttgatacggaccccgtcgttttgccgca
                  ZmUbiInt                                          manA (PMI)
7,820          7,840          7,860          7,880          7,900

PflMI                                                          BsmI
tgactgaactttatggtatggaaaatccgtccagccagccgatggccgagctgtggatgggcgcacatccgaaaagcagttcacgagtgcagaatgccgccggagat
actgacttgaaataccataccttttaggcaggtcggtcggctaccggctcgacacctacccgcgtgtaggcttttcgtcaagtgctcacgtcttacggcggcctcta
                                           manA (PMI)
7,920          7,940          7,960          7,980          8,000          8,020

EcoRV                                                    AloI                               FspI
atcgtttcactgcgtgatgtgattgagagtgataaatcgactctgctcggagaggccgttgccaaacgctttggcgaactgcctttcctgttcaaagtattatgcgc
tagcaaagtgacgcactacactaactctcactatttagctgagacgagcctctccggcaacggtttgcgaaaccgcttgacggaaaggacaagtttcataatacgcg
                                           manA (PMI)
8,040          8,060          8,080          8,100          8,120

BciVI
agcacagccactctccattcaggttcatccaaacaaacacaattctgaaatcggttttgccaaagaaaatgccgcaggtatcccgatgatgccgccgagcgtaact
tcgtgtcggtgagaggtaagtccaagtaggtttgtttgtgttaagactttagccaaaacggtttcttttacggcgtccataggactacctacggcggctcgcattga
                                           manA (PMI)
8,140          8,160          8,180          8,200          8,220

AarI
ataaagatcctaaccacaagccggagctggttttttgcgctgacgcctttccttgcgatgaacgcgtttcgtgaattttccgagattgtctccctactccagccggtc
tatttctaggattggtgttcggcctcgaccaaaaacgcgactgcggaaaggaacgcctacttgcgcaaagcacttaaaaggctctaacagagggatgaggtcggccag
                                           manA (PMI)
8,240          8,260          8,280          8,300          8,320          8,340
```

FIGURE 1K atcaccgtccaccaacgaacgccaacgttgtcacttgtcaggtcggttgagacttgtatttttttttgtcctccgtaaaaatcggttcaccag
tagtggcaggtggttgcttgcggttgcaacagtgaacagtccagccaactctgaacataaaaaaaaacaggaggcatttttagccaagtggtc 3' flanking seq_Chr5:13911933..13913119

10,490　10,500　10,510　10,520　10,530　10,540　10,550　10,560　10,570

FIGURE 10

TACGTATACCTGCTGCAGCAGCATCTGCGTAAGCACAGCCTAGATATATGCTTCTGTGTGGACTGAAAGGAGACTT
TGTTTATCAATTAGTATACTCCCAAAAAACTGATGACACCAATGATGCAAATAGGCTGGGAATAGTCTGTCTAATA
GTTTGAGTGAATCATGTCACTGATAGTTTAAACTGAAGGCGGGAAACGACAATCTGATCATGAGCGGAGAATTAAG
GGAGTCACGTTATGACCCCCGCCGATGACGCGGGACAAGCCGTTTTACGTTTGGAACTGACAGAACCGCAACGTTG
AAGGAGCCACTCAGCAA

FIGURE 4

INIR12 TRANSGENIC MAIZE

REFERENCE TO SEQUENCE LISTING SUBMITTED ELECTRONICALLY

The sequence listing contained in the file named "10085US1_ST25.txt", which is 100,907 bytes as measured in the Windows operating system, and which was created on Feb. 12, 2021 and electronically filed via EFS-Web on Feb. 12, 2021, is incorporated herein by reference in its entirety.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic maize event which confers tolerance to certain lepidopteran insect pests is the MIR162 transgenic maize event disclosed in U.S. Patent No.; 8455720. MIR162 transgenic maize plants express a VIP3Aa20 protein which can confer resistance to fall armyworm (*Spodoptera frugiperda*), corn earworm (*Helicoverpa zea*), western bean cutworm (*Striacosta albicosta*), and black cutworm (*Agrotis ipsilon*) infestations. MIR162 transgenic maize plants also express a phosphomannose isomerase selectable marker protein.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015,1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells comprising a first ZmUbilnt promoter, a vip3Aa19 coding region which is operably linked to said promoter, a CaMV 35S terminator element which is operably linked to said vip3Aa19 coding region, and a nopaline synthase terminator element, wherein said cell does not contain a second ZmUbilnt promoter and an operably linked phosphomannose isomerase coding region between said terminator elements are provided. Transgenic maize plant cell comprising a nucleotide sequence comprising a first ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a second ZmUbilnt promoter and an operably linked phosphomannose isomerase coding region between said terminator elements are provided. Transgenic maize plant cells comprising a nucleotide sequence comprising a ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a phosphomannose isomerase coding region between said terminator elements are provided. Transgenic maize plant cells comprising a nucleotide sequence comprising a first ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a second ZmUbilnt promoter and an operably linked phosphomannose isomerase coding region are provided. Transgenic maize plant cell comprising a nucleotide sequence comprising a ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a phosphomannose isomerase coding region are provided. In certain embodiments, aforementioned transgenic maize plant cells wherein:(i) the ZmUbilnt promoter, the vip3Aa19 coding region which is operably linked to said promoter, the CaMV 35S terminator element which is operably linked to said vip3Aa19 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait are provided. Transgenic maize plant cells comprising an INIR12 transgenic locus comprising the first ZmUbilnt promoter, the vip3Aa19 coding region which is operably linked to said promoter, the CaMV 35S terminator element which is operably linked to said vip3Aa19 coding region, and the nopaline synthase terminator element of an original MIR162 transgenic locus allelic variants thereof, or other variants thereof, wherein DNA of said original MIR162 transgenic locus, allelic variants thereof, or other variants thereof comprising a second ZmUbilnt promoter and an operably linked phosphomannose isomerase coding region is absent are provided. In certain embodiments, the original MIR162 transgenic locus is set forth in SEQ ID NO: 1, is present in seed deposited at the ATCC under accession No. PTA-8166 or progeny thereof, is an allelic variant thereof, or is another variant thereof. In certain embodiments, an INIR12 transgenic locus further comprises an insertion and/or substitution of a DNA element comprising a cognate guide RNA recognition site (CgRRS) in a junction polynucleotide of said INIR12 transgenic locus, wherein the CgRRS optionally comprises SEQ ID NO: 37. In certain embodiments, transgenic maize plant cells comprising a INIR12 transgenic locus set forth in SEQ ID NO: 2, 3, 4, 5, 6, 29, or 43 are provided. Also provided are transgenic maize plants and parts thereof including seeds which comprise the aforementioned transgenic maize plant cells. INIR12 transgenic maize plants provided herein can exhibit resistance to fall armyworm (*Spodoptera frugiperda*), corn earworm (*He-* licoverpa zea), western bean cutworm (*Striacosta albicosta*), and black cutworm (*Agrotis ipsilon*) infestations in comparison to control maize plants which lack the Vip3Aa protein.

Methods or obtaining a bulked population of inbred seed comprising selfing any of the aforementioned INIR12 transgenic maize plants and harvesting seed comprising the INIR12 transgenic locus from the selfed maize plant are provided.

Methods of obtaining hybrid maize seed comprising crossing any of the aforementioned INIR12 transgenic maize plant to a second maize plant which is genetically distinct from the first maize plant and harvesting seed comprising the INIR12 transgenic locus from the cross are provided.

DNA molecules comprising any one of SEQ ID NO: 7, 8, 9, 10, 11, 12, 13, 14, 15, 16, 17, 18, 19, 25, 37, 40, 41, 42, or 43 are provided. Processed transgenic maize plant products and biological samples comprising the aforementioned DNA molecules are also provided. Methods of detecting a maize plant cell comprising a INIR12 transgenic locus comprising the step of detecting a DNA molecule comprising SEQ ID NO: 7, 8, 9, 10, 11, 12, 13, 14, 15, 16, 17, 18, 19, 25, 37, 39, 40, 41, 42, or 43 are also provided.

Also provided are methods of excising a INIR12 transgenic locus comprising an CgRRS and an originator guide RNA recognition site (OgRRS) from the genome of a maize plant cell comprising the steps of: (a) contacting a transgenic plant genome of a maize plant cell comprising the INIR12 transgenic locus with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR12 transgenic locus flanked by the OgRRS and the CgRRS has been excised.

Also provided are methods of making transgenic maize plant cell comprising an INIR12 transgenic locus comprising: (a) contacting the transgenic plant genome of a maize MIR162 plant cell with: (i) a first set of gene editing molecules comprising a first site-specific nuclease which introduces a first double stranded DNA break in a 5' junction polynucleotide of an MIR162 transgenic locus; and (ii) a second set of gene editing molecules comprising a second site-specific nuclease which introduces a second double stranded DNA break between the CaMV35S terminator element and the ZmUbi promoter of said MIR162 transgenic locus which is operably linked to DNA encoding a phosphomannose isomerase (pmi) and a third site specific nuclease which introduces a third double stranded DNA break between the DNA encoding the pmi and DNA encoding the nopaline synthase (nos) terminator element of said MIR162 transgenic locus; and (b) selecting a transgenic maize plant cell, transgenic maize callus, and/or a transgenic maize plant comprising an INIR12 transgenic locus wherein one or more nucleotides of said 5' junction polynucleotide have been deleted and/or substituted, wherein the first ZmUbilnt promoter, the vip3Aa19 coding region which is operably linked to the first ZmUbilnt promoter, the CaMV 35S terminator element which is operably linked to said vip3Aa19 coding region, and the nos terminator element of said MIR162 transgenic locus are present, and wherein DNA of said MIR162 transgenic locus comprising a second ZmUbilnt promoter and an operably linked phosphomannose isomerase coding region is absent, thereby making a transgenic maize plant cell comprising an INIR12 transgenic locus. Transgenic maize plant cells, transgenic maize plant callus, transgenic maize plants, and transgenic maize plant seeds comprising an INIR12 transgenic locus made by the aforementioned methods are also provided. Also provided are methods of modifying a transgenic maize plant cell comprising: obtaining a MIR162 maize event plant cell, a representative sample of which was deposited at the ATCC under accession No. PTA-8166, comprising a nucleotide sequence comprising a first ZmUbilnt promoter, a vip3Aa19 coding region which is operably linked to said promoter, a CaMV 35S terminator element which is operably linked to said vip3Aa19 coding region, a second ZmUbilnt promoter and an operably linked phosphomannose isomerase coding region, and a nopaline synthase terminator element; and modifying said nucleotide sequence to eliminate functionality of said phosphomannose isomerase coding region and/or to substantially, essentially, or completely remove said phosphomannose isomerase coding region, and optionally to eliminate functionality of, or substantially, essentially, or completely remove, said second ZmUbilnt promoter. Also provided are methods of modifying a transgenic maize plant cell comprising: obtaining a MIR162 maize event plant cell, a representative sample of which was deposited at the ATCC under accession No. PTA-8166, comprising a nucleotide sequence comprising a first ZmUbilnt promoter, a vip3Aa19 coding region which is operably linked to said promoter, a CaMV 35S terminator element which is operably linked to said vip3Aa19 coding region, a second ZmUbilnt promoter and an operably linked phosphomannose isomerase coding region, and a nopaline synthase terminator element; and modifying said nucleotide sequence to substantially, essentially, or completely remove said phosphomannose isomerase coding region, and optionally substantially, essentially, or completely remove said second ZmUnilnt promoter.

BRIEF DESCRIPTION OF THE DRAWINGS/FIGURES

Figure 1H:
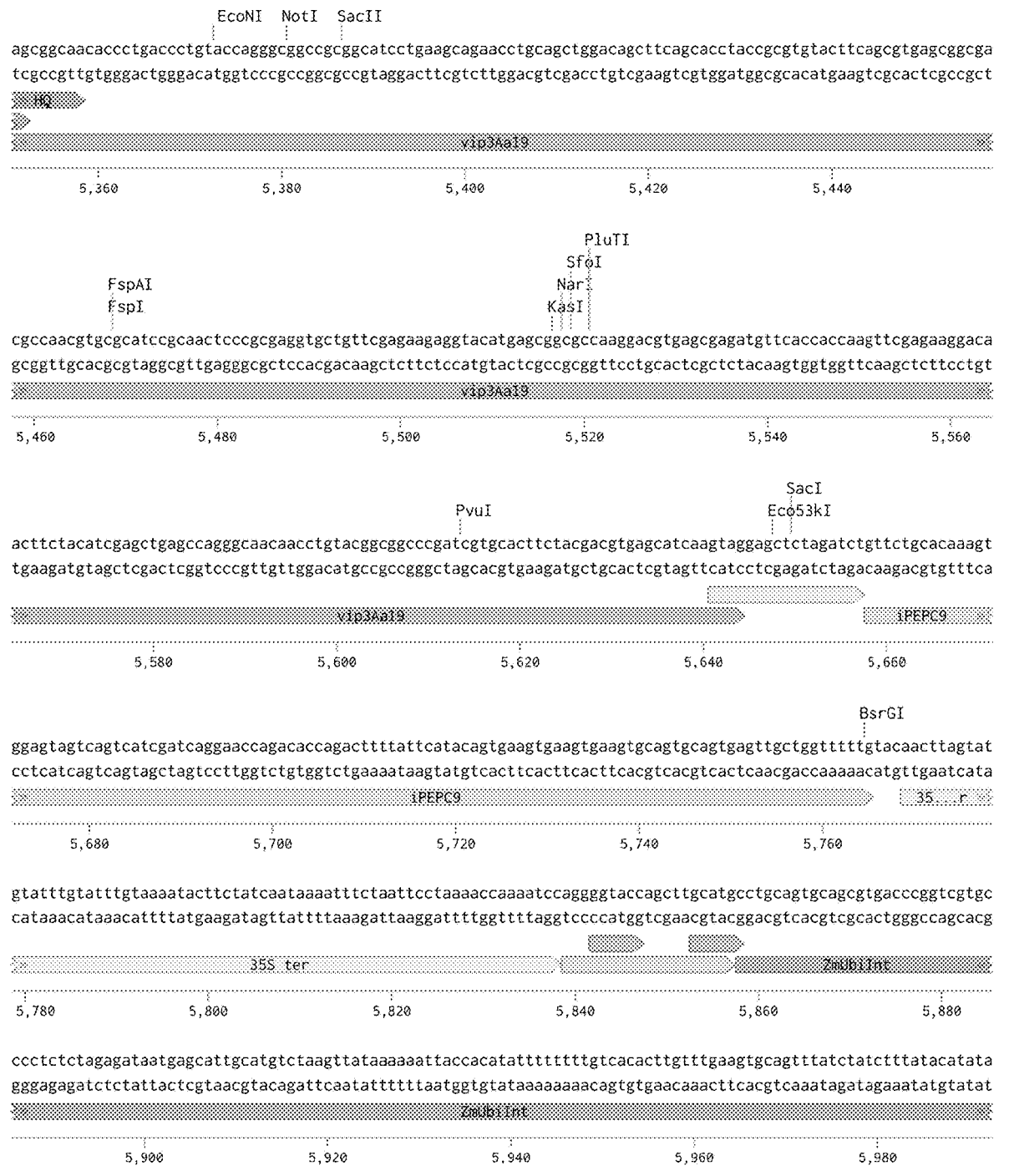
Figure 1P:
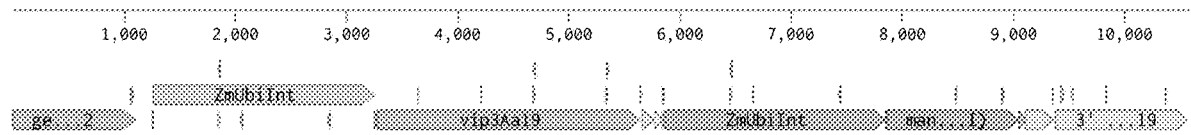

FIG. 1A-P shows sequence (SEQ ID NO: 1) of the MIR162 event transgenic locus including the genomic DNA and 5' and 3' junction sequences flanking the inserted transgenic DNA as well as a diagram of transgene expression cassettes and selectable markers in the transgenic locus.

Figure 2:
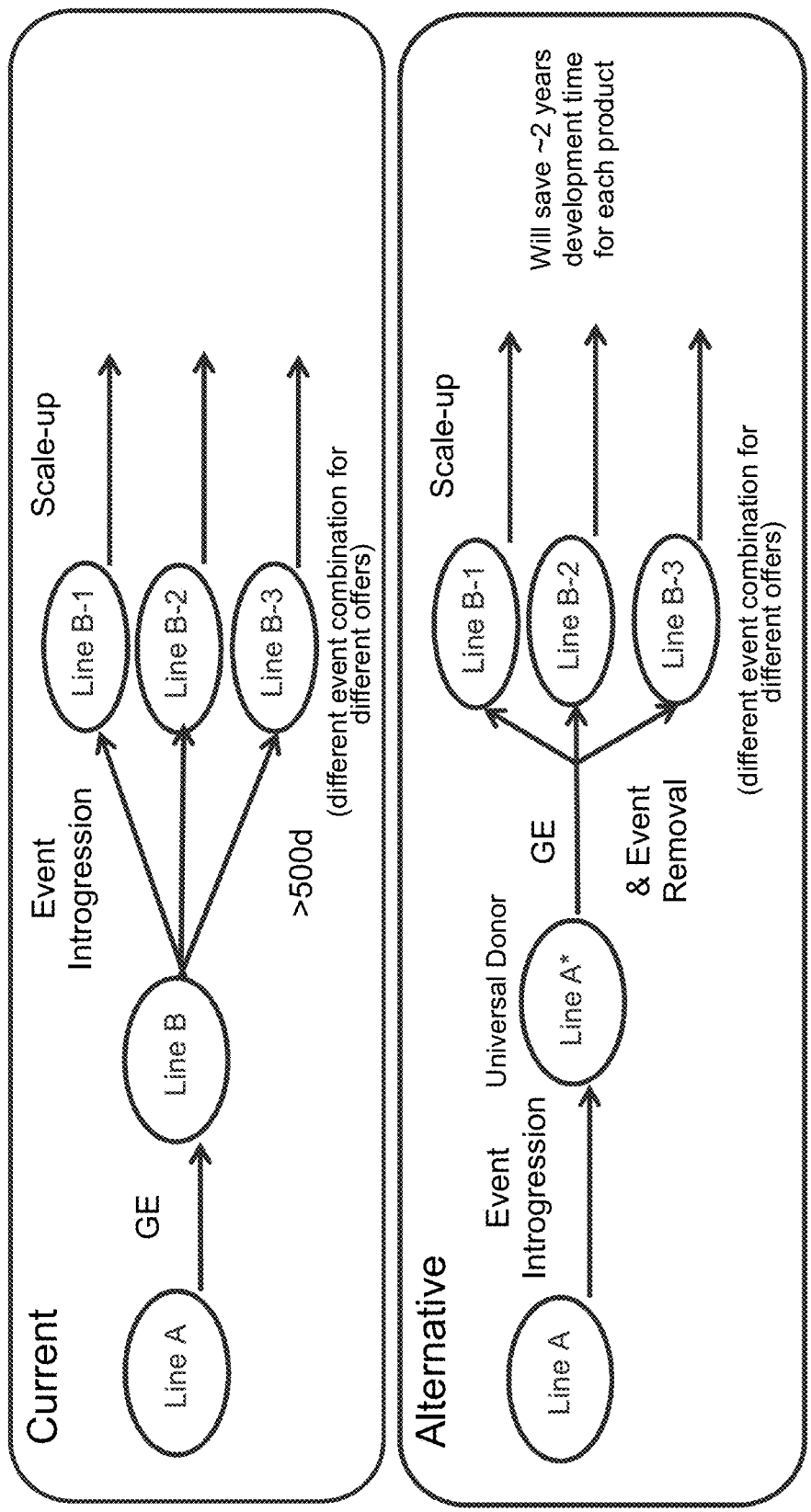

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") or portion thereof with genome editing molecules.

Figure 3A:
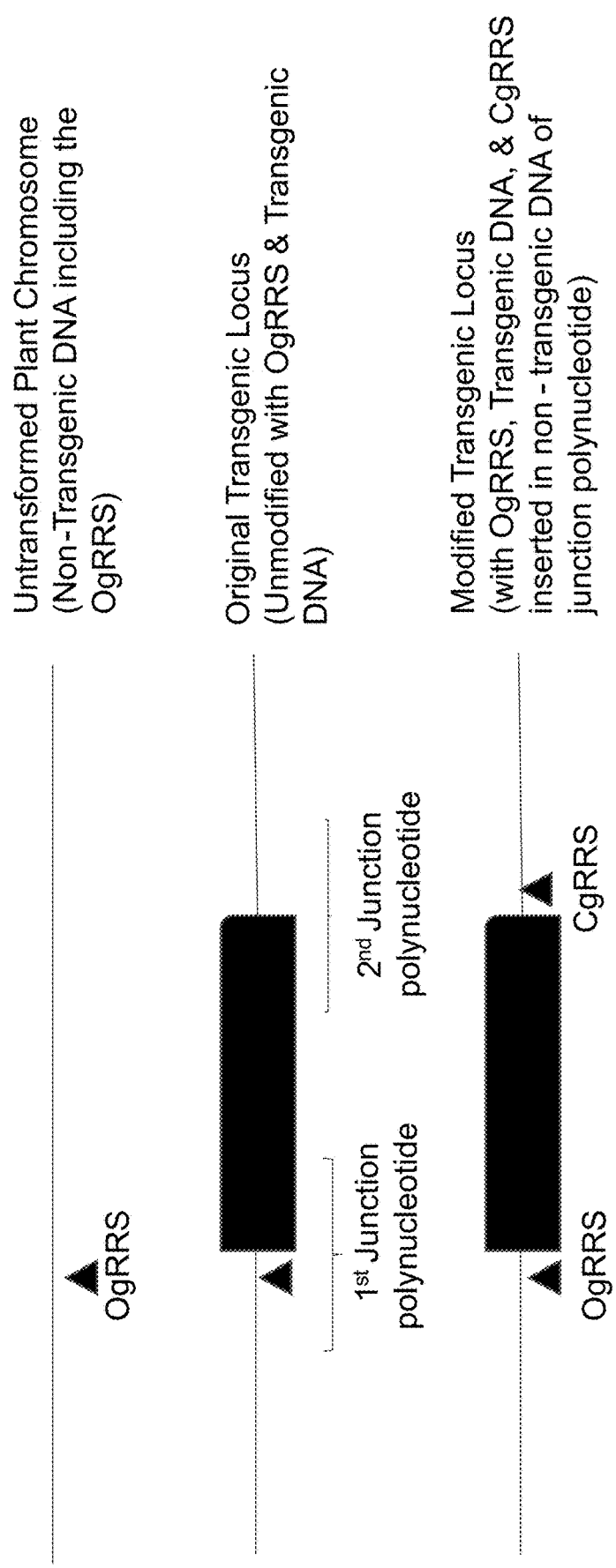
Figure 3B:
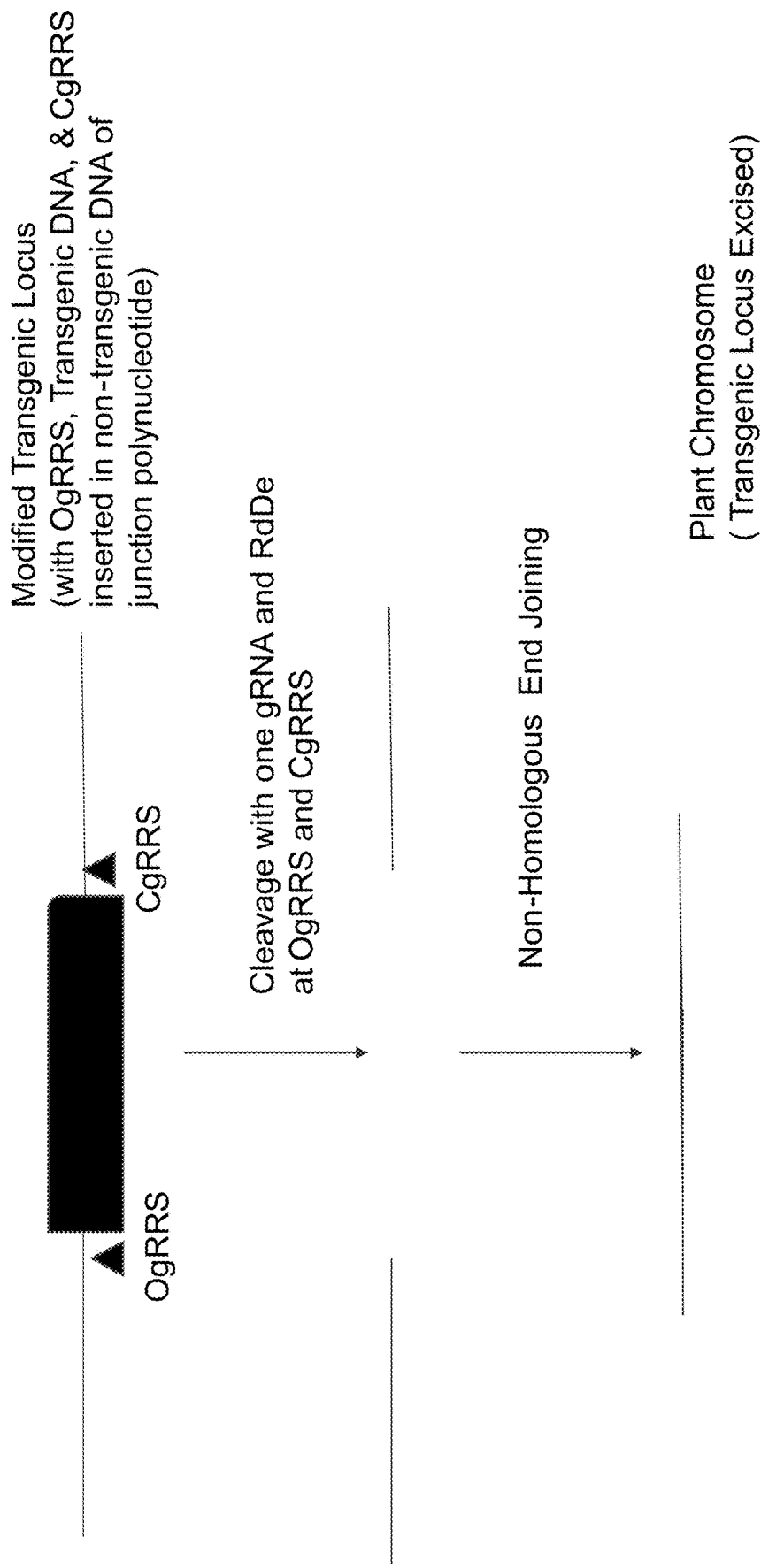
Figure 3C:
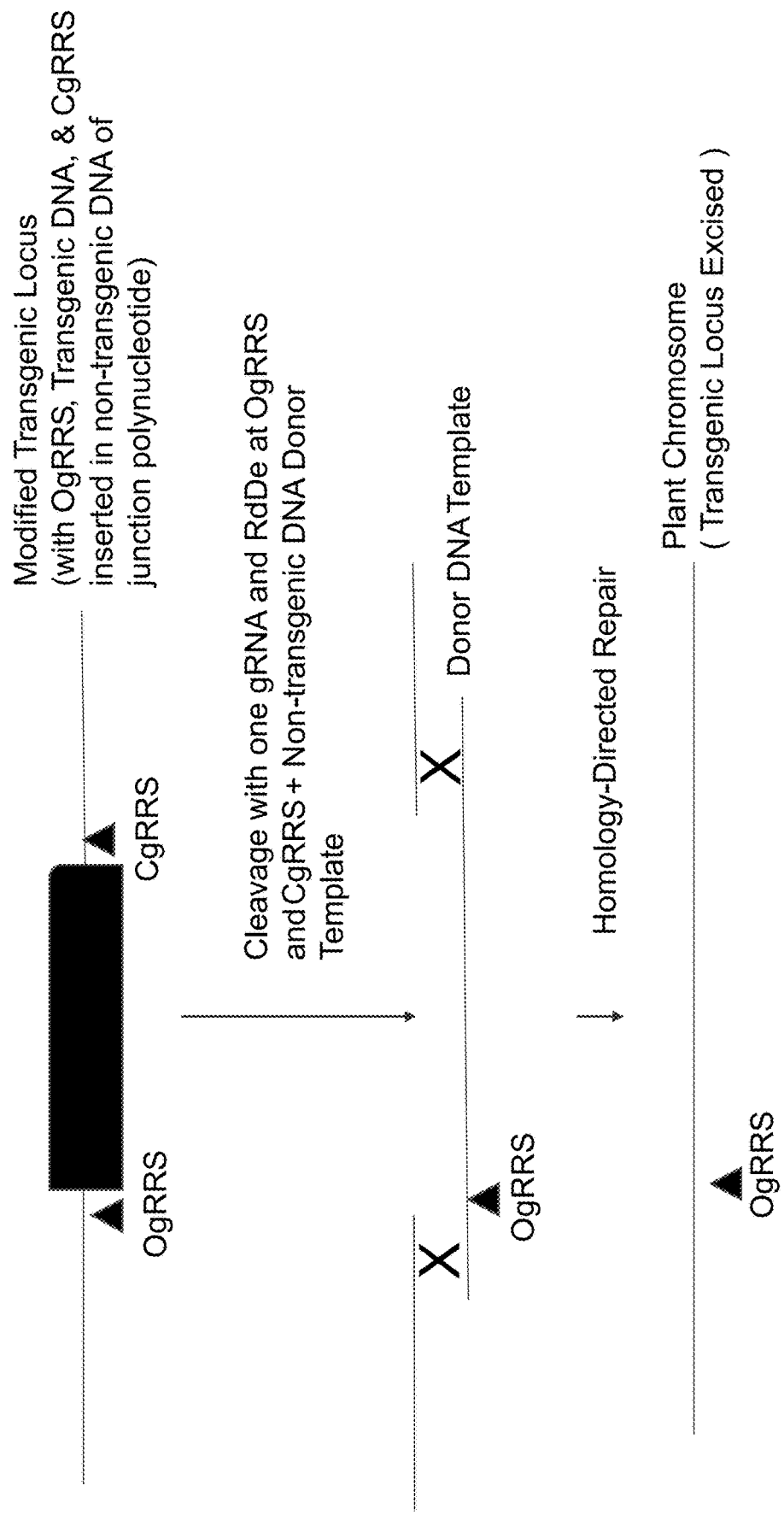

FIG. 3A, B, C. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the 1$^{st}$ junction polynucleotide (middle); and (iii) the modified transgenic locus with a cognate guide RNA inserted into the non-transgenic DNA of the 2$^{nd}$ junction polynucleotide (bottom). FIG. 3B shows a schematic diagram of a non-limiting example of a process where a modified transgenic locus with a cognate guide RNA inserted into the non-transgenic DNA of the 2$^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 3C shows a schematic diagram of a non-limiting example of a process where a modified transgenic locus with a cognate guide RNA inserted into the non-transgenic DNA of the 2$^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template containing the OgRRS. In FIG. 3C, cleavage of the modified transgenic locus in the presence of the donor DNA template containing the OgRRS which has homology to non-transgenic DNA in the 1$^{st}$ and 2$^{nd}$ junction polynucleotides followed by homology-directed repair processes to provide a plant chromosome where the transgenic locus is excised and the OgRRS and other non-transgenic DNA present in the untransformed plant chromosome is at least partially restored.

FIG. 4 shows a schematic diagram of the hybridization sites for gRNAs of SEQ ID NO: 20, 21, and 22. The 5' junction polynucleotide sequence set forth in FIG. 4 corresponds to nucleotides 920 to 1240 of SEQ ID NO: 1.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g. milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). Cas12a proteins include the protein provided herein as SEQ ID NO: 38.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g. inbred or doubled haploid. Elite crop plants can include inbred lines used as is or used as pollen donors or pollen recipients in hybrid seed production (e.g. used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g. DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR12" is used herein to refer either individually or collectively to items that include any or all of the MIR162 transgenic maize loci which have been modified as disclosed herein, transgenic maize plants and parts thereof including seed that comprise the modified MIR162 transgenic loci, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

As used herein, the term "MIR162" is used to refer to items that include a transgenic maize locus, transgenic maize plants and parts thereof including seed set forth in U.S. Pat. No. 8,455,720, which is incorporated herein by reference in its entirety. Representative MIR162 transgenic maize seed have been deposited at the American Type Culture Collection (ATCC, Manassas, Va., USA) as accession No. PTA-8166. MIR162 transgenic loci include loci having the sequence of SEQ ID NO:1, the sequence of the MIR162 locus in the deposited seed of accession No. PTA-8166 and any progeny thereof, as well as allelic variants and other variants of SEQ ID NO:1. Other variants of a MIR162 locus can include variants in MIR162 other than those disclosed herein obtained by gene editing techniques (e.g., by use of RdDe, CBE, or ABE and gRNAs, TALENs, and/or ZFN).

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS, sPAM sites, or sigRNAR sites are operably linked to junction polynucleotides when they can be recognized by a gRNA and an RdDe to provide for excision of the transgenic locus or portion thereof flanked by the junction polynucleotides. When the phrase "operably linked" is used in the context of a signature PAM site and a DNA junction polynucleotide, it refers to a PAM site which permits cleavage of at least one strand of DNA in the junction polynucleotide with an RNA dependent DNA endonuclease, RNA dependent DNA binding protein, or RNA dependent DNA nickase which recognizes the PAM site when a guide RNA complementary to sequences adjacent to the PAM site is present. When the phrase "operably linked" is used in the context of a sigRNAR site and a DNA junction polynucleotide, it refers to a sigRNAR site which permits cleavage of at least one strand of DNA in the junction polynucleotide with an RNA dependent DNA endonuclease, RNA dependent DNA binding protein, or RNA dependent DNA nickase which recognizes the sigRNAR site when a guide RNA complementary to the heterologous sequences adjacent in the sigRNAR site is present.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus or portion thereof has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "signature protospacer adjacent motif (sPAM)" or acronym "sPAM" refer to a PAM which has been introduced into a transgenic plant genome by genome editing, wherein the sPAM is absent from a transgenic plant genome comprising the original transgenic locus. An sPAM can be introduced by an insertion, deletion, and or substitution of one or more nucleotides in genomic DNA.

As used herein the phrase "signature guide RNA Recognition site" or acronym "sigRNAR" refer to a DNA polynucleotide comprising a heterologous crRNA (CRISPR RNA) binding sequence located immediately 5' or 3' to a PAM site, wherein the sigRNAR site has been introduced into a transgenic plant genome by genome editing and wherein at least the heterologous crRNA binding sequence is absent from a transgenic plant genome comprising the original transgenic locus. In certain embodiments, the heterologous crRNA binding sequence is operably linked to a pre-existing PAM site in the transgenic plant genome. In other embodiments, the heterologous crRNA binding sequence is operably linked to a sPAM site in the transgenic plant genome.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel).

INIR12 transgenic loci comprising modifications of a MIR162 transgenic loci in a maize plant genome by directed insertion, deletion, and/or substitution of DNA within or adjacent to such MIR162 transgenic loci as well as methods of making and using such INIR12 transgenic loci are provided herein. In certain embodiments, the INIR12 transgenic loci comprise the first ZmUbilnt promoter, the vip3Aa19 coding region which is operably linked to said promoter, the CaMV 35S terminator element which is operably linked to said vip3Aa19 coding region, and the nopaline synthase terminator element of an MIR162 transgenic locus, wherein DNA of said MIR162 transgenic locus comprising a second ZmUbilnt promoter and an operably linked phosphomannose isomerase (pmi) coding region is absent. Such INIR12 transgenic loci can thus comprise a vip3Aa19 expression cassette having two tandemly arrayed terminator elements (i.e., a CaMV35S and a NOS terminator) while lacking non-essential DNA elements (i.e., the duplicate copy of the ZmUbilnt promoter and pmi selectable marker gene which is operably linked thereto).

In certain embodiments, INIR12 transgenic loci provided herein can thus comprise deletions of selectable marker genes and/or repetitive sequences. In its unmodified form (in certain embodiments, the "unmodified form" is the "original form," "original transgenic locus," etc.) a MIR162 transgenic locus comprises a phosphomannose isomerase (pmi)-encoding selectable marker gene which confers the ability to grow on mannose as a carbon source. In embodiments provided herein, the selectable marker gene which is deleted comprises, consists essentially of, or consists of a DNA molecule encoding: (i) the phosphomannose isomerase (pmi) of a MIR162 transgenic locus and the ZmUbi promoter that is operably linked thereto; or (ii) the phosphomannose isomerase (pmi) of a MIR162 transgenic locus and both the ZmUbi promoter and NOS terminator that are operably linked thereto. In certain embodiments, DNA elements comprising the ZmUbi promoter and operably linked pmi coding region corresponding to at least nucleotides 5837, 5838, 5840, 5845, or 5850 to 8040, 9060, 9080, 9090, 9100, or 9105 of SEQ ID NO: 1 can be absent from an INIR12 locus. In certain embodiments, the INIR12 locus comprising a deletion of DNA encoding the pmi gene and the operably linked ZmUbi promoter is set forth in SEQ ID NO: 2, wherein nucleotides designated n in the sequence are either absent, independently selected from a guanine, a cytosine, an adenine residue, or a thymine, comprise or consist of 1 or more nucleotides corresponding to nucleotides 5831 to 5836 of SEQ ID NO: 1 and/or comprise or consist of 1 or more nucleotides corresponding to nucleotides 9102 to 9107 of SEQ ID NO: 1. In certain embodiments, the deletion junction sequence present in an INIR12 transgenic locus comprises a DNA molecule set forth in SEQ ID NO: 25 which corresponds to nucleotides 5821 to 5850 of SEQ ID NO: 6. In certain embodiments, the DNA comprising the ZmUbi promoter and operably linked pmi coding region to be deleted is flanked by operably linked protospacer adjacent motif (PAM) sites in a MIR162 transgenic locus which are recognized by an RNA dependent DNA endonuclease (RdDe); for example, a class 2 type II or class 2 type V RdDe. In certain embodiments, the deleted selectable marker gene is replaced in an INIR12 transgenic locus by an introduced DNA sequence as discussed in further detail elsewhere herein. For example, in certain embodiments, the introduced DNA sequence comprises a trait expression cassette such as a trait expression cassette of another transgenic locus. In addition to the deletion of a selectable marker gene, in certain embodiments at least one copy of a repetitive sequence has also been deleted with genome editing molecules from an MIR162 transgenic locus. In certain embodiments, the repetitive sequence comprises, consists essentially of, or consists of the two distinct ZmUbilnt promoters which are each operably linked to the VIP3Aa gene and to the pmi selectable marker gene within the MIR162 transgenic locus (e.g., as depicted in FIG. 1). In certain embodiments, the repetitive sequence which comprises, consists essentially of, or consists of the second ZmUbilnt promoter and which is operably linked to the pmi selectable maker of an MIR162 transgenic locus is absent from the INIR12 transgenic locus. In certain embodiments, any of the aforementioned INIR12 transgenic loci can optionally further comprise: (i) an OgRRS and a CgRRS which are operably linked to a $1^{st}$ and a $2^{nd}$ junction sequence of the INIR12 transgenic locus; (ii) one or more signature protospacer adjacent motif (sPAM) sites which are operably linked to a $1^{st}$ and a $2^{nd}$ junction sequence of the INIR12 transgenic locus; or (iii) signature guide RNA Recognition site (sigRNAR) sites which are operably linked to a $1^{st}$ and a $2^{nd}$ junction sequence of the INIR12 transgenic locus. Also provided herein are plants comprising any of aforementioned INIR12 transgenic loci.

In certain embodiments, an INIR12 transgenic locus can further comprise modifications of a 5' or 3' junction polynucleotide of an MIR162 transgenic locus (e.g., as set forth in SEQ ID NO: 1 and in FIG. 1). Such modifications of junction polynucleotides include deletions of DNA segments comprising non-essential transgenic DNA in the junction polynucleotide. In certain embodiments, such deletions of non-essential DNA of a 5' junction polynucleotide of an INIR12 transgenic locus include those set forth in SEQ ID NO: 3, wherein one or more nucleotides in a segment corresponding to nucleotides 1089 to 1098 are absent or independently selected from A, C, G, or T, with the proviso that the nucleotides 1089 to 1098 of SEQ ID NO:3 are not identical to nucleotides 1089 to 1098 of SEQ ID NO: 1. In certain embodiments, such deletions of non-essential DNA of a 5' junction polynucleotide of an INIR12 transgenic locus include those wherein nucleotides corresponding to nucleotides 1081 to 1104 of SEQ ID NO:3 are: (i) each either absent or independently selected from a guanine, a cytosine, an adenine residue, or a thymine residue; (ii) comprise about 2 to 8 consecutive residues of nucleotides 1,081 to 1092 of SEQ ID NO: 1 and/or about 2 to 8 consecutive residues of nucleotides 1093 to 1104 of SEQ ID NO: 1; or (iii) any combination of (i) and (ii), wherein each of (i), (ii), and (iii) are with the proviso that the nucleotides corresponding to nucleotides 1081 to 1104 of SEQ ID NO: 3 are not identical to nucleotides 1081 to 1104 of SEQ ID NO: 1. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 7, wherein n is absent, is independently selected from A, C, G, or T, correspond to 1 to 10 residues of nucleotides 1083 to 1092 of SEQ ID NO: 1, and/or correspond to 1 to 10 residues of nucleotides 1093 to 1102 of SEQ ID NO: 1 with the proviso that nucleotides corresponding to nucleotide 3 to 22 of SEQ ID NO: 7 are not identical to residues 1083 to 1102 of SEQ ID NO: 1. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 8, wherein n is absent, is independently selected from A, C, G, or T, correspond to 1 to 5 residues of nucleotides 1088 to 1092 of SEQ ID NO: 1, and/or correspond to 1 to 5 residues of nucleotides 1093 to 1097 of SEQ ID NO: 1 with the proviso that nucleotides corresponding to residues 8 to 17 of SEQ ID NO: 8 are not identical to residues 1088 to 1097 of SEQ ID NO: 1. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 9; wherein n is absent, is independently selected from A, C, G, or T, correspond to 1 to 3 residues of nucleotides 1090-1092 of SEQ ID NO: 1, and/or correspond to 1 to 3 residues of nucleotides 1093 to 1095 of SEQ ID NO: 1 with the proviso that nucleotides corresponding to residues 1090 to 1095 of SEQ ID NO: 9 are not identical to nucleotides 1090 to 1095 of SEQ ID NO: 1. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 10, 11, 12, 13, 14, 15, 16, 17, 18, or 19. In certain embodiments, such deletions of non-essential DNA of a 5' junction polynucleotide of an INIR12 transgenic locus include those set forth in SEQ ID NO: 39 and 40.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR12 transgenic loci provided here are characterized by polynucleotide sequences that can facilitate as necessary the removal of the INIR12 transgenic loci from the genome. Useful applications of such INIR12 transgenic loci and related methods of making include targeted excision of a INIR12 transgenic locus or portion thereof in certain breeding lines to facilitate recovery of germplasm with subsets of transgenic traits tailored for specific geographic locations and/or grower preferences. Other useful applications of such INIR12 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR12 transgenic loci or portions thereof which can be selectively excised with one or more gRNA molecules and RdDe (RNA dependent DNA endonucleases) which form gRNA/target DNA complexes. Such selectively excisable INIR12 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. Examples of OgRRS polynucleotide sequences in or near a 3' junction polynucleotide in an MIR162 transgenic locus include SEQ ID NO: 26, 27, and 28. OgRRS polynucleotide sequences located in a first junction polynucleotide can be introduced into the second junction polynucleotide using donor DNA templates as illustrated in FIG. 3C and as elsewhere described herein. A donor DNA template for introducing the SEQ ID NO: 27 OgRRS into the 5' junction polynucleotide of an MIR162 locus includes the donor DNA template of SEQ ID NO: 32. Integration of the SEQ ID NO: 32 donor DNA template into the 5' junction polynucleotide of an MIR162 locus can provide an INIR12 locus comprising the CgRRS sequence set forth in SEQ ID NO: 37.

Such selectively excisable INIR12 transgenic loci can also comprise signature protospacer adjacent motif (sPAM) sites and/or signature guide RNA recognition (sigRNAR) sites, wherein the sPAM and/or sigRNAR sites are operably linked to both DNA junction polynucleotides of the INIR12 transgenic locus. Such sigRNAR sites can be recognized by RdDe and suitable guide RNAs containing crRNA complementary to heterologous DNA sequences adjacent to a PAM or sPAM site to provide for cleavage within or near the two junction polynucleotides. Such heterologous sequences which introduced at the sigRNAR site are at least 17 or 18 nucleotides in length and are complementary to the crRNA of a guide RNA. In certain embodiments, the heterologous polynucleotide of the sigRNAR is about 17 or 18 to about 24 nucleotides in length. Non-limiting features of the heterologous DNA sequences in the sigRNAR include: (i) absence of significant homology or sequence identity (e.g., less than 50% sequence identity across the entire length of the heterologous sequence) to any other endogenous or transgenic sequences present in the transgenic plant genome or in other transgenic genomes of the maize plant being edited (ii) absence of significant homology or sequence identity (e.g., less than 50% sequence identity across the entire length of the heterologous sequence) of a heterologous sequence of a first sigRNAR site to a heterologous sequence of a second or third sigRNAR site; and/or (ii) optimization of the heterologoussequence for recognition by the RdDe and guide RNA when used in conjunction with a particular PAM sequence. In certain embodiments, the sigRNAR sites which are created are recognized by the same class of RdDe (e.g., Class 2 type II or Class 2 type V) or by the sameRdDe (e.g., both sPAMs or PAMs of the sigRNAR recognized by the same RdDe (e.g., Cas9 or Cas 12 RdDe). In certain embodiments, the same sigRNAR sites can be introduced in both 5' and 3' junction polynucleotides to permit excision of the INIR12 transgenic locus by a single guide RNA and a single RdDe. In certain embodiments, different sets of distinct sigRNAR sites can be introduced in the 5' and 3' junction polynucleotides of different transgenic loci to permit selective excision of any single transgenic locus by a single guide RNA and a single RdDe directed to the distinct sigRNAR sites that flank the transgenic locus. A sigRNAR site can be created in the plant genome by inserting the heterologous sequence adjacent to a pre-existing PAM sequence using genome editing molecules. A sigRNAR site can be created in the plant genome by inserting the heterologous sequence adjacent to a preexisting PAM sequence using genome editing molecules. A sigRNAR site also can be created in the plant genome by inserting both the heterologous sequence and an associated PAM or sPAM site in a junction polynucleotide. Such insertions can be made in non-transgenic plant genomic DNA of the junction polynucleotide, in the inserted transgenic DNA of the junction polynucleotide, or can span the junction comprising both non-transgenic plant genomic DNA and inserted transgenic DNA of the junction polynucleotide. Such nucleotide insertions can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion. Guide RNAs can be directed to the junction polynucleotides by using a pre-existing PAM site located within or adjacent to a junction polynucleotide of the transgenic locus.

Also provided are unique transgenic locus excision sites created by excision of INIR12 transgenic loci or selectively excisable INIR12 transgenic loci, DNA molecules comprising the INIR12 transgenic loci or unique fragments thereof (i.e., fragments of an INIR12 locus which are not found in an MIR162 transgenic locus), INIR12 plants comprising the same, biological samples containing the DNA, nucleic acid markers adapted for detecting the DNA molecules, and related methods of identifying maize plants comprising unique INIR12 transgenic locus excision sites and unique fragments of a INIR12 transgenic locus. DNA molecules comprising unique fragments of an INIR12 transgenic locus are diagnostic for the presence of an INIR12 transgenic locus or fragments thereof in a maize plant, maize cell, maize seed, products obtained therefrom (e.g., seed meal or stover), and biological samples. DNA molecules comprising unique fragments of an INIR12 transgenic locus include DNA molecules comprising modified 5' junction polynucleotides. Unique 5' junction polynucleotides of an INIR12 transgenic locus include: (i) a DNA molecule comprising nucleotides corresponding to nucleotides 1080 or 1082 to 1102 or 1104 of SEQ ID NO: 1 with the proviso that the DNA molecules is not identical to residues 1080 or 1082 to 1102 or 1104 of SEQ ID NO: 1); or (ii) any one of SEQ ID NO: 7, 8, or 9, with the proviso that the DNA molecules is not identical to residues 1080 or 1082 to 1102 or 1104 of SEQ ID NO: 1; or (iii) or SEQ ID NO: 10, 11, 12, 13, 14, 15, 16, 17, 18, 19, 39, or 40. DNA molecules comprising unique fragments of an INIR12 transgenic locus also include DNA molecules comprising modified junction polynucleotides containing CgRRS sequences comprising insertions of OgRRS sequences (e.g., a CgRRS element comprising SEQ ID NO: 37). DNA molecules comprising unique fragments of an INIR12 transgenic locus also include DNA molecules comprising deletion junctions corresponding to residues spanning the deletion of the phosphomannose isomerase coding region and operably linked ZmUbilnt promoter in the INIR12 transgenic locus. Such deletion junctions thus comprise one or more nucleotides located between the 35S terminator element and the 5' end of the ZmUbilnt promoter (e.g., nucleotides 5839 to 5858 of SEQ ID NO: 1) which are directly joined to (i.e., are contiguous with) nucleotides located between or at the 3' terminus of the pmi coding region and the 5' end of the NOS terminator in a MIR162 locus (e.g., nucleotides 9040 to 9105 of SEQ ID NO: 1). Examples of unique INIR12 DNA fragment comprising a such deletion include nucleotides 5821 to 5850 of SEQ ID NO: 2, wherein one or more nucleotides designated n are absent, independently selected from a guanine, a cytosine, an adenine residue, or a thymine residue, comprise or consist of 1 or more nucleotides corresponding to nucleotides 5831 to 5836 of SEQ ID NO: 1 and/or comprise or consist of 1 or more nucleotides corresponding to nucleotides 9102 to 9107 of SEQ ID NO: 1 junction. Another example of a unique INIR12 DNA fragment comprising such adeletion junction include SEQ ID NO: 25, which corresponds to residues 5821 to 5850 of an INIR12 locus set forth in SEQ ID NO: 6. Another example of a unique INIR12 DNA fragment comprising such a deletion junction include SEQ ID NO: 41 and 42. In certain embodiments, any of the aforementioned unique fragments of an INIR12 transgenic locus comprise DNA molecules of at least about 18, 20, or 24 nucleotides to about 30, 50, 100, or 200 nucleotides in length. Also provided herein are nucleic acid hybridization probes and primers (e.g., for SNP analysis) adapted for detection of INIR12 transgenic loci which can comprise all or part of any of the aforementioned DNA molecules and optionally a detectable label. Methods and reagents (e.g., nucleic acid markers including nucleic acid probes and/or primers) for detecting plants, edited plant genomes, and biological samples containing DNA molecules comprising the transgenic loci excision sites and/or non-essential DNA deletions are also provided herein. Detection of the DNA molecules can be achieved by any combination of nucleic acid amplification (e.g., PCR amplification), hybridization, sequencing, and/or mass-spectrometry based techniques. Methods set forth for detecting junction nucleic acids in unmodified transgenic loci set forth in U.S. 20190136331 and U.S. Pat. No. 9,738,904, both incorporated herein by reference in their entireties, can be adapted for use in detection of the nucleic acids provided herein. In certain embodiments, such detection is achieved by amplification and/or hybridization-based detection methods using a method (e.g., selective amplification primers) and/or probe (e.g., capable of selective hybridization or generation of a specific primer extension product) which specifically recognizes the target DNA molecule (e.g., transgenic locus excision site) but does not recognize DNA from an unmodified transgenic locus. In certain embodiments, the hybridization probes can comprise detectable labels (e.g., fluorescent, radioactive, epitope, and chemiluminescent labels). In certain embodiments, a single nucleotide polymorphism detection assay can be adapted for detection of the target DNA molecule (e.g., transgenic locus excision site). Detection of any of the aforementioned unique DNA fragments comprising SEQ ID NO: 10, 11, 12, 13, 14, 15, 16, 17, 18, 19, 39, 40, 41, and/or 42 in a biological sample indicates that the sample contains material from a INIR12 plant or seed.

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize MIR162 transgenic locus. The maize MIR162 transgenic locus and its transgenic junction sequences are also depicted in FIG. 1. Maize plants comprising the MIR162 transgenic locus and seed thereof have been cultivated, been placed in commerce, and have been described in a variety of publications by various governmental bodies. Databases which have compiled descriptions of the MIR162 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of an original MIR162 transgenic locus which can be improved by the methods provided herein are set forth or otherwise provided in SEQ ID NO: 1, U.S. Pat. No. 8,455,720, the sequence of the MIR162 locus in the deposited seed of ATCC accession No. PTA-8166, and elsewhere in this disclosure. In certain embodiments provided herein, the MIR162 transgenic locus set forth in SEQ ID NO: 1 or present in the deposited seed of ATCC accession No. PTA-8166 is referred to as original MIR162 transgenic locus. Allelic or other variants of the sequence set forth SEQ ID NO: 1, the patent references set forth therein and incorporated herein by reference in their entireties, and elsewhere in this disclosure which may be present in certain variant MIR162 transgenic plant loci (e.g., progeny of deposited seed of accession No. PTA-8166 which contain allelic variants of SEQ ID NO:1 or progeny originating from transgenic plant cells comprising the original MIR162 transgenic set forth in U.S. Pat. No. 8,455,720 which contain allelic variants of SEQ ID NO:1) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, or 10,579 nucleotides of SEQ ID NO: 1. Also provided are plants, plant parts including seeds, genomic DNA, and/or DNA obtained from INIR12 plants which comprise one or more modifications (e.g., via insertion of a CgRRS in a junction polynucleotide sequence) which provide for selective excision of the INIR12 transgenic locus or a portion thereof (e.g., the Vip3A coding region and operably linked promoter). Such INIR12 transgenic loci can be treated with gene editing molecules (e.g., RdDe and gRNA(s)) to obtain plants wherein a segment comprising, consisting essentially of, or consisting of the INIR12 transgenic locus or a portion thereof (e.g., the Vip3A coding region and operably linked promoter) is deleted. In certain embodiments, the MIR162 transgenic loci set forth in SEQ ID NO: 1 and allelic variants thereof are further modified by deletion of a segment of DNA comprising, consisting essentially of, or consisting of a selectable marker gene or portions thereof (e.g, the pmi coding region and operably linked ZmUbi promoter) and/or non-essential DNA (e.g., T-DNA border sequences or anything other than the ZmUbi1::VIP3a::t35S expression cassette) to obtain INIR12 transgenic loci. In certain embodiments, the INIR12 transgenic locus comprises a deletion of the phosphomannose isomerase (PMI) coding region and operably linked ZmUbi promoter which are in a MIR162 transgenic locus. Also provided herein are methods of detecting plants, genomic DNA, and/or DNA obtained from plants comprising a INIR12 transgenic locus which contains one or more of a CgRRS, deletions of selectable marker genes, deletions of non-essential DNA, and/or a transgenic locus excision site. A first junction polynucleotide of a MIR162 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INIR12 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the MIR162 transgenic locus of SEQ ID NO: 1, allelic variants thereof, or other variants thereof to obtain an INIR12 transgenic locus. In other embodiments, the OgRRS is found in non-transgenic DNA or transgenic DNA of the 3' junction polynucleotide of the MIR162 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INIR12 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR12 transgenic locus, in transgenic DNA of a DNA junction polynucleotide of an INIR12 transgenic locus or can span the junction of the transgenic and non-transgenic DNA of a DNA junction polynucleotide of an INIR12 transgenic locus. An OgRRS can likewise be located in non-transgenic plant genomic DNA of a DNA junction polynucleotide of an INIR12 transgenic locus, in transgenic DNA of a DNA junction polynucleotide of an INIR12 transgenic locus or can span the junction of the transgenic and non-transgenic DNA of a DNA junction polynucleotide of an INIR12 transgenic locus.

Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR12 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g. Line A+ in FIG. 2) comprising two or more of the modified transgenic loci. This elite germplasm containing the modified transgenic loci (e.g. "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR12 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019): 321-342 as well as in U.S. Pat. No. 8,618,358; U.S. 20130031674; and U.S. 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in U.S. 20030082813, U.S. 20080134353, U.S. 20090328252, U.S. 20100100981, U.S. 20110165679, U.S. 20140157453, U.S. 20140173775, and U.S. 20170240911, which are each incorporated by reference in their entireties. In certain embodiments, the genome edits can be effected in regenerable plant parts (e.g.; plant embryos) of elite crop plants by transient provision of gene editing molecules or polynucleotides encoding the same and do not necessarily require incorporating a selectable marker gene into the plant genome (e.g., U.S. 20160208271 and U.S. 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR12 transgenic locus comprising an OgRRS in non-transgenic DNA of a 1' junction polynucleotide sequence and a CgRRS in a $2^{nd}$ junction polynucleotide sequence is deleted with a gRNA and RdDe that recognize the OgRRS and the CgRRS to produce an INIR12 transgenic locus excision site. In certain embodiments, a segment comprising an INIR12 transgenic locus comprising a sPAM and/or a sigRNAR site in a $1^{st}$ junction polynucleotide sequence and a sPAM and/or a sigRNAR in a $2^{nd}$ junction polynucleotide sequence is deleted with at least one gRNA and RdDe that recognize the sPAM and/or a sigRNAR to produce an INIR12 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR12 transgenic loci excision sites are provided herein.

In other embodiments, a segment comprising a INIR12 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a MIR162 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR12 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides nd repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are at least partially or essentially restored.

In certain embodiments, edited transgenic plant genomes provided herein can lack one or more selectable and/or scoreable markers found in an original event (transgenic locus). Original MIR162 transgenic loci (events), including those set forth in SEQ ID NO: 1), U.S. Pat. No. 8,455,720, the sequence of the MIR162 locus in the deposited seed of accession No. PTA-8166 and progeny thereof, contain a selectable phosphomannose isomerase (pmi) transgene marker conferring an ability to grow on mannose. Transgenes encoding a phosphomannose isomerase (pmi) can confer the ability to grow on mannose. In certain embodiments provided herein, the DNA element comprising, consisting essentially of, or consisting of the ZmUbi promoter which is operably linked to a pmi coding region of an MIR162 transgenic locus is absent from an INIR12 transgenic locus, or scoreable marker transgenes can be excised from an original transgenic locus by contacting the transgenic locus with one or more gene editing molecules which introduce double stranded breaks in the transgenic locus at the 5' and 3' end of the expression cassette comprising the selectable marker transgene (e.g., an RdDe and guide RNAs directed to PAM sites located at the 5' and 3' end of the expression cassette comprising the selectable marker transgenes) and selecting for plant cells, plant parts, or plants wherein the selectable or scoreable marker has been excised. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable or scoreable marker transgene by eliminating or reducing promoter activity, introducing a missense mutation, and/or introducing a pre-mature stop codon. In certain embodiments, the selectable and/or scoreable marker transgene can be replaced by an introduced transgene. In certain embodiments, an original transgenic locus that was contacted with gene editing molecules which introduce double stranded breaks in the transgenic locus at the 5' and 3' end of the expression cassette comprising the selectable marker and/or scoreable transgene can also be contacted with a suitable donor DNA template comprising an expression cassette flanked by DNA homologous to remaining DNA in the transgenic locus located 5' and 3' to the selectable marker excision site. In certain embodiments, a coding region of the selectable and/or scoreable marker transgene can be replaced with another coding region such that the replacement coding region is operably linked to the promoter and 3' terminator or polyadenylation site of the selectable and/or scoreable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in U.S. Patent Application Public. Nos. 20090038026, 20130031674, 20150361446, 20170088904, 20150267221, 201662346688, and 20200190533 as well as in U.S. Pat. Nos. 6,342,660, 7,323,556, 8,575,434, 6,040,497, 8,759, 618, 7,157,281, 6,852,915, 7,705,216, 10316330, 8618358, 8450561, 8212113, 9428765, 7897748, 8273959, 8093453, 8901378, 9994863, 7928296, and 8466346, each of which are incorporated herein by reference in their entireties.

In certain embodiments, INIR12 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in U.S. Patent Application Publication 20190352655, which is incorporated herein by example, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; U.S. 20190032070; incorporated herein by reference in its entirety); (e) TMSS (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in U.S. Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in U.S. Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in U.S. Patent Application Publications 2016/0138008A1 and U.S.2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in U.S. Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in U.S. Patent Application Publications US 2015/0082478A1 and U.S. 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in U.S. Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in U.S. Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) *Nature,* 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., *Sci Adv.* 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) *Nature* 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) *Nature Rev. Genet.,* 11:636-646; Mohanta et al. (2017) *Genes* vol. 8,12: 399; Ramirez et al. Nucleic Acids Res. (2012); 40(12): 5560-5568; Liu et al. (2013) *Nature Communications,* 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8,12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e.g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor DNA template (e.g., SEQ ID NO: 32). In certain embodiments, integration of the donor DNA templates can be facilitated by use of a bacteriophage lambda exonuclease, a bacteriophage lambda beta SSAP protein, and an E. coli SSB essentially as set forth in U.S. Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e.g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor DNA template e (e.g., SEQ ID NO: 32).

Various treatments are useful in delivery of gene editing molecules and/or other molecules to a MIR162 or INIR12 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in U.S. Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature*, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g.; herbicide tolerance, insect resistance, and/or male sterility) are introduced into a MIR162 or INIR12 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in U.S. Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in U.S. Patent Application Publication 2002/0192813 A1. All of the patent publications referenced in this paragraph are incorporated herein by reference in their entireties.

In certain embodiments, the MIR162 or INIR12 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www [dot]openwetware[dot]org/images/d/d3/Haploid_Arabidopsis_protocol[dot]pdf; (Ravi et al. (2014) *Nature Communications*, 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the MIR162 or INIR12 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the MIR162 or INIR12 plant cells in used in the methods provided herein can include dividing cells. Dividing cells can include those cells found in various plant tissues including leaves, meristems, and embryos. These tissues include but are not limited to dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in U.S. Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR12 plant from a INIR12 plant cell that had been subjected to the gene editing or from a regenerable plant structure obtained from that INIR12 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from U.S. Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR12 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

EMBODIMENTS

Various embodiments of the plants, genomes, methods, biological samples, and other compositions described herein are set forth in the following sets of numbered embodiments.

1a. A transgenic maize plant cell comprising a first ZmUbilnt promoter, a vip3Aa19 coding region which is operably linked to said promoter, a CaMV 35S terminator element which is operably linked to said vip3Aa19 coding region, and a nopaline synthase terminator element, wherein said cell does not contain a second ZmUbilnt promoter and an operably linked phosphomannose isomerase coding region between said terminator elements, optionally wherein: (i) the ZmUbilnt promoter, the vip3Aa19 coding region which is operably linked to said promoter, the CaMV 35S terminator element which is operably linked to said vip3Aa19 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1b. A transgenic maize plant cell comprising a nucleotide sequence comprising a first ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a second ZmUbilnt promoter and an operably linked phosphomannose isomerase coding region between said terminator elements optionally wherein: (i) the ZmUbilnt promoter, the vip3Aa19 coding region which is operably linked to said promoter, the CaMV 35S terminator element which is operably linked to said vip3Aa19 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1c. A transgenic maize plant cell comprising a nucleotide sequence comprising a ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a phosphomannose isomerase coding region between said terminator elements, optionally wherein: (i) the ZmUbilnt promoter, the vip3Aa19 coding region which is operably linked to said promoter, the CaMV 35S terminator element which is operably linked to said vip3Aa19 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1d. A transgenic maize plant cell comprising a nucleotide sequence comprising a first ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a second ZmUbilnt promoter and an operably linked phosphomannose isomerase coding region, optionally wherein: (i) the ZmUbilnt promoter, the vip3Aa19 coding region which is operably linked to said promoter, the CaMV 35S terminator element which is operably linked to said vip3Aa19 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1e. A transgenic maize plant cell comprising a nucleotide sequence comprising a ZmUbilnt promoter, a vip3Aa19 coding region which is operably linked to said promoter, a CaMV 35S terminator element which is operably linked to said vip3Aa19 coding region, and a nopaline synthase terminator element, wherein said nucleotide sequence does not contain a phosphomannose isomerase coding region, optionally wherein: (i) the ZmUbilnt promoter, the vip3Aa19 coding region which is operably linked to said promoter, the CaMV 35S terminator element which is operably linked to said vip3Aa19 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1f. A transgenic maize plant cell comprising an INIR12 transgenic locus comprising the first ZmUbilnt promoter, the vip3Aa19 coding region which is operably linked to said promoter, the CaMV 35S terminator element which is operably linked to said vip3Aa19 coding region, and the nopaline synthase terminator element of a MIR162 transgenic locus, allelic variants thereof, or other variants thereof, wherein DNA of said original MIR162 transgenic locus, allelic variants thereof, or other variants thereof comprising a second ZmUbilnt promoter and an operably linked phosphomannose isomerase coding region is absent.

2. The transgenic maize plant cell of embodiment 1a, b, c, d, e, or f, wherein said INIR12 transgenic locus comprises DNA corresponding to at least nucleotide number 1101 to 5830 of SEQ ID NO:1 and nucleotide number 9111 to 9360 of SEQ ID NO:1, wherein nucleotides corresponding to at least 5850 to 9090 of SEQ ID NO: 1 are absent.

3. The transgenic maize plant cell of embodiment 1 a, b, c, d, e, or f, wherein said INIR12 transgenic locus comprises the DNA molecule set forth in SEQ ID NO: 2, 6, 29, or 43.

4. The transgenic maize plant cell of embodiment 1 a, b, c, d, e, or f, wherein said INIR12 transgenic locus comprises:

(a) the DNA molecule set forth in SEQ ID NO: 3 wherein nucleotide residues 1081 to 1104 are: (i) each either absent or independently selected from a guanine, a cytosine, an adenine residue, or a thymine residue, with the proviso that nucleotides corresponding to residues 1081 to 1104 of SEQ ID NO: 3 are not identical to residues 1081 to 1104 of SEQ ID NO: 1; (ii) comprise about 2 to 8 consecutive residues of nucleotides 1081 to 1092 of SEQ ID NO: 1 and/or about 2 to 8 consecutive residues of nucleotides 1093 to 1104 of SEQ ID NO: 1, with the proviso that nucleotides corresponding to residues 1081 to 1104 of SEQ ID NO: 3 are not identical to residues 1081 to 1104 of SEQ ID NO: 1; (iii) any combination of (i) and (ii); (v) are set forth in SEQ ID NO: 7, wherein n is absent, is independently selected from A, C, G, or T, correspond to 1 to 10 residues of nucleotides 1083 to 1092 of SEQ ID NO: 1, and/or correspond to 1 to 10 residues of nucleotides 1093 to 1102 of SEQ ID NO: 1 with the proviso that nucleotides corresponding to nucleotide 3 to 22 of SEQ ID NO: 7 are not identical to residues 1083 to 1102 of SEQ ID NO: 1; (vi) are set forth in SEQ ID NO: 8; wherein n is absent, is independently selected from A, C, G, or T, correspond to 1 to 5 residues of nucleotides 1088 to 1092 of SEQ ID NO: 1, and/or correspond to 1 to 5 residues of nucleotides 1093 to 1097 of SEQ ID NO: 1 with the proviso that nucleotides corresponding to residues 8 to 17 of SEQ ID NO: 8 are not identical to residues 1088 to 1097 of SEQ ID NO: 1; (vii) are set forth in SEQ ID NO: 9; wherein n is absent, is independently selected from A, C, G, or T, correspond to 1 to 3 residues of nucleotides 1090-1092 of SEQ ID NO: 1, and/or correspond to 1 to 3 residues of nucleotides 1093 to 1095 of SEQ ID NO: 1 with the proviso that nucleotides corresponding to residues 1090 to 1095 of SEQ ID NO: 9 are not identical to nucleotides 1090 to 1095 of SEQ ID NO: 1); or (viii) are set forth in SEQ ID NO: 10, 11, 12, 13, 14, 15, 16, 17, 18, or 19 and wherein nucleotides 5831 to 5842 of SEQ ID NO: 3 are each either absent, independently selected from a guanine, a cytosine, an adenine residue, or a thymine residue, comprise or consist of 1 or more nucleotides corresponding to nucleotides 5831 to 5836 of SEQ ID NO: 1, and/or comprise or consist of 1 or more nucleotides corresponding to nucleotides 9102 to 9107 of SEQ ID NO: 1.

5. The transgenic maize plant cell of embodiment 1 a, b, c, d, e, or f, wherein said INIR12 transgenic locus further comprises an insertion and/or substitution of a DNA element comprising a cognate guide RNA recognition site (CgRRS) in a DNA junction polynucleotide of said INIR12 transgenic locus.

6. The transgenic maize plant cell of embodiment 5, wherein said cognate guide RNA recognition site (CgRRS) comprises SEQ ID NO: 26, 27, or 28, wherein the insertion and/or substitution is in a 5' junction polynucleotide of said INIR12 transgenic locus and optionally wherein the insertion and/or substitution is in a 5' junction polynucleotide of the INIR12 transgenic locus corresponding to at least one of nucleotides 1079 to 1098 of SEQ ID NO: 1.

7. The transgenic maize plant cell of embodiment 6, wherein said CgRRS comprises the DNA molecule set forth in SEQ ID NO: 37.

8. The transgenic maize plant cell of embodiment 1 a, b, c, d, e, or f, wherein said INIR12 transgenic locus comprises the DNA molecule set forth in SEQ ID NO: 2, 3, 4, 5, 6, 29, or 43 or wherein said MIR162 transgenic locus is set forth in SEQ ID NO:1, is present in seed deposited at the ATCC under accession No. PTA-8166, is present in progeny thereof, is present in allelic variants thereof, or is present in other variants thereof.

9. A transgenic maize plant part comprising the maize plant cell of any one of embodiments 1 a, b, c, d, e, or f, 2, 3, 4, 5, 6, 7, or 8, wherein said maize plant part is optionally a seed.

10. A transgenic maize plant comprising the maize plant cell of any one of embodiments 1 a, b, c, d, e, or f, 2, 3, 4, 5, 6, 7, 8, or 8.

11. A method for obtaining a bulked population of inbred seed comprising selfing the transgenic maize plant of embodiment 10 and harvesting seed comprising the INIR12 transgenic locus from the selfed maize plant.

12. A method of obtaining hybrid maize seed comprising crossing the transgenic maize plant of embodiment 10 to a second maize plant which is genetically distinct from the first maize plant and harvesting seed comprising the INIR12 transgenic locus from the cross.

13. A DNA molecule comprising SEQ ID NO: 7, 8, 9, 10, 11, 12, 13, 14, 15, 16, 17, 18, 19, 25, 37, 39, 40, 41, or 42.

14. A processed transgenic maize plant product comprising the DNA molecule of embodiment 13.

15. A biological sample containing the DNA molecule of embodiment 13.

16. A nucleic acid molecule adapted for detection of genomic DNA comprising the DNA molecule of embodiment 13, wherein said nucleic acid molecule optionally comprises a detectable label.

17. A method of detecting a plant cell comprising the INIR12 transgenic locus of any one of embodiments 1 a, b, c, d, e, or f to 8, comprising the step of detecting DNA molecule comprising SEQ ID NO: 7, 8, 9, 10, 11, 12, 13, 14, 15, 16, 17, 18, 19, 25, 37, 39, 40, 41, or 42.

18. A method of excising the INIR12 transgenic locus from the genome of the maize plant cell of any one of embodiments 5, 6, or 7, comprising the steps of:

(a) contacting the edited transgenic plant genome of the plant cell of embodiment 5 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR12 transgenic locus flanked by the OgRRS and the CgRRS has been excised.

19. The method of embodiment 18, wherein the OgRRS is located in a 3' flanking DNA junction polynucleotide and comprises SEQ ID NO: 26, 27, or 28 and wherein the CgRRS comprises an insertion or substitution of SEQ ID NO: 26, 27, or 28 in a 5' junction polynucleotide of said INIR12 transgenic locus.

20. The method of embodiment 19, wherein the insertion and/or substitution is in a 5' junction polynucleotide of the INIR12 transgenic locus corresponding to at least one of nucleotides 1079 to 1098 of SEQ ID NO: 1.

21. The method of embodiment 19, wherein the CgRRS comprises the DNA molecule set forth in SEQ ID NO: 37.

20a. A method of modifying a transgenic maize plant cell comprising: obtaining a MIR162 maize event plant cell, a representative sample of which was deposited at the ATCC under accession No. PTA-8166, comprising a nucleotide sequence comprising a first ZmUbilnt promoter, a vip3Aa19 coding region which is operably linked to said promoter, a CaMV 35S terminator element which is operably linked to said vip3Aa19 coding region, a second ZmUbilnt promoter and an operably linked phosphomannose isomerase coding region, and a nopaline synthase terminator element; and modifying said nucleotide sequence to eliminate functionality of said phosphomannose isomerase coding region and/or to substantially, essentially, or completely remove said phosphomannose isomerase coding region, and optionally to eliminate functionality of, or substantially, essentially, or completely remove, said second ZmUbilnt promoter.

20b. A method of modifying a transgenic maize plant cell comprising: obtaining a MIR162 maize event plant cell, a representative sample of which was deposited at the ATCC under accession No. PTA-8166, comprising a nucleotide sequence comprising a first ZmUbilnt promoter, a vip3Aa19 coding region which is operably linked to said promoter, a CaMV 35S terminator element which is operably linked to said vip3Aa19 coding region, a second ZmUbilnt promoter and an operably linked phosphomannose isomerase coding region, and a nopaline synthase terminator element; and modifying said nucleotide sequence to substantially, essentially, or completely remove said phosphomannose isomerase coding region, and optionally substantially, essentially, or completely remove said second ZmUnilnt promoter.

20c. A method of making transgenic maize plant cell comprising an INIR12 transgenic locus comprising:
(a) contacting the transgenic plant genome of a maize MIR162 plant cell with: (i) a first set of gene editing molecules comprising a first site-specific nuclease which introduces a first double stranded DNA break in a 5' junction polynucleotide of an MIR162 transgenic locus; and (ii) a second set of gene editing molecules comprising a second site-specific nuclease which introduces a second double stranded DNA break between the CaMV35S terminator element and the ZmUbi promoter of said MIR162 transgenic locus which is operably linked to DNA encoding a phosphomannose isomerase (pmi) and a third site specific nuclease which introduces a third double stranded DNA break between the DNA encoding the pmi and DNA encoding the nopaline synthase (nos) terminator element of said MIR162 transgenic locus; and
(b) selecting a transgenic maize plant cell, transgenic maize callus, and/or a transgenic maize plant comprising an INIR12 transgenic locus wherein one or more nucleotides of said 5' junction polynucleotide have been deleted and/or substituted, wherein the first ZmUbilnt promoter, the vip3Aa19 coding region which is operably linked to the first ZmUbilnt promoter, the CaMV 35S terminator element which is operably linked to said vip3Aa19 coding region, and the nos terminator element of said MIR162 transgenic locus are present, and wherein DNA of said MIR162 transgenic locus comprising a second ZmUbilnt promoter and an operably linked phosphomannose isomerase coding region is absent, thereby making a transgenic maize plant cell comprising an INIR12 transgenic locus.

21. The method of embodiment 20c, comprising:
(a) contacting the transgenic plant genome of a maize MIR162 plant cell with: (i) a first set of gene editing molecules comprising a first site-specific nuclease which introduces a first double stranded DNA break between nucleotide residues corresponding to nucleotide number 1079 to 1098 of SEQ ID NO: 1; and (ii) a second set of gene editing molecules comprising a second site-specific nuclease which introduces a second double stranded DNA break between nucleotide residues corresponding to nucleotide number 5838 to 5858 of SEQ ID NO: 1 and a third site specific nuclease which introduces a third double stranded DNA break between nucleotide residues corresponding to nucleotide number 9040 to 9105 of SEQ ID NO: 1; and
(b) selecting a transgenic maize plant cell, transgenic maize plant callus, and/or a transgenic maize plant wherein one or more nucleotides corresponding to nucleotide number 1081 to 1104 of SEQ ID NO: 1 have been deleted and/or substituted, wherein nucleotides corresponding to at least nucleotide number 5858 to 9040 of SEQ ID NO: 1 have been deleted and/or replaced, and wherein nucleotides corresponding to at least nucleotide number 1105 to 5837 of SEQ ID NO: 1 are retained.

22. The method of embodiment 20c or 21, further comprising contacting the transgenic plant genome of the maize MIR162 plant cell with a donor DNA template comprising a cognate guide RNA recognition site (CgRRS), wherein said CgRRS optionally comprises a polynucleotide set forth in SEQ ID NO: 26, 27, 28, or 37; and selecting a transgenic plant cell wherein said CgRRS has integrated into and/or replaced one or more nucleotides corresponding to at least one of nucleotides 1079 to 1098 of SEQ ID NO: 1.

23. The method of any one of embodiments 20c or 21, wherein the gene editing molecules comprise: (i) a zinc finger nuclease; (ii) a TALEN; and/or (iii) an RNA dependent DNA endonuclease (RdDe) and a guide RNA.

24. The method of embodiment 23, wherein the RNA dependent DNA endonuclease (RdDe) comprises a Cas12a RdDe and wherein the guide RNA of said first set of gene editing molecules comprises SEQ ID NO: 20, the guide RNA of said second set of gene-editing molecules comprises SEQ ID NO: 21, and the guide RNA of said third set of gene-editing molecules comprises SEQ ID NO: 23.

25. The method of any one of embodiments 20a, b, or c to 24, further comprising the step of regenerating transgenic maize plant callus and/or a transgenic maize plant comprising the modification or the INIR12 transgenic locus from said transgenic maize plant cell selected in step (c).

26. The method of any one of embodiments 20a, b, or c to 25, further comprising the step of harvesting a transgenic maize plant seed comprising the modification or the INIR12 transgenic locus from the transgenic maize plant comprising the modification or the INIR12 transgenic locus.

27. A transgenic maize plant cell comprising a modification or an INIR12 transgenic locus made by the method of any one of embodiments 20a, b, or c to 25.

28. Transgenic maize plant callus comprising a modification or an INIR12 transgenic locus made by the method of any one of embodiments 20a, b, or c to 25.

29. A transgenic maize plant comprising a modification or an INIR12 transgenic locus made by the method of any one of embodiments 20a, b, or c to 25.

30. A transgenic maize plant seed comprising a modification or an INIR12 transgenic locus made by the method of embodiment 26.

EXAMPLES

Example 1. Application of a Cas12a and Guide RNAs to Change or Excise the 5'-T-DNA Junction Sequence in the MIR162 Event The MIR162 5'-junction sequence shown in FIG. 4 is flanked by three Cas12a recognition sequences, gRNA-1 (SEQ ID NO: 20), gRNA-2 (SEQ ID NO: 21), and gRNA-3 (SEQ ID NO: 22) that can be used to modify some of the 5' junction sequence or eliminate most of it. There are four possible iterations of this approach. The first two depend on gRNA-1 and gRNA-3 alone to disrupt the MIR162 5'-junction sequence. The second two combine gRNA-2 with either gRNA-1 or gRNA-3 to eliminate most of the MIR162 junction sequence. In certain instances, gRNA-1 (SEQ ID NO: 20) is used to modify the 5' DNA junction polynucleotide and obtain a modified 5' junction polynucleotide comprising SEQ ID NO: 39 or 40.

The Cas12a nuclease and the single or combined gRNAs are introduced into the MIR162 event. This can be accomplished in different ways that are familiar to those with ordinary skill in the art. The first is to encode expression of the Cas12a nuclease and gRNA(s) on a T-DNA and transform it into the MIR162 event via *Agrobacterium*-mediated transformation. Alternatively, the T-DNA can be transformed into any convenient maize line, and then crossed with the MIR162 event to combine the Cas12a ribonucleoprotein expressing T-DNA with the MIR162 event. The Cas12a nuclease and gRNAs can also be assembled in vitro then delivered to MIR162 explants as ribonucleoprotein complexes using a biolistic approach (Svitashev et al., 2016; doi: 10.1038/ncomms13274). Also, a plasmid encoding a Cas12a nuclease and the gRNA(s) can be delivered to MIR162 explants using a biolistic approach. This will produce plant cells that have a high likelihood of incurring mutations that disrupt the MIR162 junction sequence. To use the *Agrobacterium* approach a binary vector that contains a strong constitutive expression cassette like the ZmUbi1 promoter::ZmUbi1 terminator driving Cas12a, a PolII or PolIII gene cassette driving the Cas12a gRNA(s) and a CaMV 35S:PAT:NOS or other suitable plant selectable marker is constructed. An expression cassette driving a fluorescent protein like mScarlet may also be useful to the plant transformation process. Constructs are transformed into *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 µM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produce callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remain on Pre-Regeneration media for 7 days. Calli beginning to initiate shoots are transferred to Regeneration medium with 7.5 mg/L PPT in Phytatrays and cultured in light at 27-28° C. Shoots that reach the top of the Phytatray with intact roots are transferred to Shoot Elongation medium prior to transplant into soil and gradual acclimatization to greenhouse conditions.

When a sufficient amount of viable tissue is obtained, it can be screened for mutations at the MIR162 junction sequence, using a PCR-based approach. One way to screen is to design DNA oligonucleotide primers that flank and amplify the MIR162 junction plus surrounding sequence. For example, the primers (5'-tttgcatcattggtgtcatcagttttt-3'; SEQ ID NO: 30) and (5'-tttcccgccttcagtttaaactatcag-3'; SEQ ID NO: 31) will produce a ~310 bp product that can be analyzed for edits at the target site. The size of this product will vary based on the nature of the edit. Amplicons can be sequenced directly using an amplicon sequencing approach or ligated to a convenient plasmid vector for Sanger sequencing. Those plants in which the MIR162 5'-junction sequence is disrupted are selected and grown to maturity. The DNA encoding the Cas12a reagents can be segregated away from the modified junction sequence in a subsequent generation.

Example 2. Insertion of a CgRRS Element in the 5'-Junction of the MIR162 Event

This example describes the construction of plant expression vectors for *Agrobacterium* mediated maize transformation. Two plant gene expression vectors are prepared. Plant expression cassettes for expressing a Bacteriophage lambda exonuclease, a bacteriophage lambda beta SSAP protein, and an *E. coli* SSB are constructed essentially as set forth in U.S. Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of U.S. Patent Application Publication 20200407754, respectively, and incorporated herein by example. DNA sequences encoding the c2 NLS-Exo, c2 NLS lambda beta SSAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, S SAP, and SSB plant expression cassettes.

A donor DNA template sequence (SEQ ID NO: 32) that targets the 5'-T-DNA junction of the MIR162 event for insertion of a 27 base pair heterologous sequence, that is identical to a Cas12a recognition site at the 3'-junction of the MIR162 T-DNA insert, by HDR is constructed. The donor DNA template sequence includes a replacement template with desired insertion region (27 base pair long sequence of SEQ ID NO: 27) flanked on both sides by homology arms about 500-635 bp in length. The homology arms match (i.e., are homologous to) gDNA (genomic DNA) regions flanking the target gDNA insertion site. The replacement template region comprising the donor DNA template is flanked at each end by DNA sequences identical to the MIR162 5' polynucleotide sequence recognized by an RNA-guided nuclease and one or more gRNA(s) (e.g. gRNAs comprising SEQ ID NO: 20, 21, and 22). In certain cases, a deletion is made in the targeted MIR162 5' polynucleotide sequence (e.g., using gRNAs comprising SEQ ID NO: 20 and 21 in combination or by using gRNAs comprising SEQ ID NO: 21 and 22 in combination).

A plant expression cassette that provides for expression of the RNA-guided sequence-specific Cas12a endonuclease is constructed. A plant expression cassette that provides for expression of a guide RNA complementary to sequences adjacent to the insertion site (e.g. gRNAs comprising SEQ ID NO: 20, 21, and 22) is constructed. An *Agrobacterium* superbinary plasmid transformation vector containing a cassette that provides for the expression of the phosphinothricin N-acetyltransferasesynthase (PAT) protein is constructed. Once the cassettes, donor sequence and *Agrobacterium* superbinary plasmid transformation vector are constructed, they were combined to generate two maize transformation plasmids.

A maize transformation plasmid is constructed with the PAT cassette, the RNA-guided sequence-specific endonuclease cassette, the guide RNA cassette, and the MIR162 5'-junction polynucleotide donor DNA template sequence into the *Agrobacterium* superbinary plasmid transformation vector (the control vector).

A maize transformation plasmid is constructed with the PAT cassette, the RNA-guided sequence-specific endonuclease cassette, the guide RNA cassette, the SSB cassette, the lambda beta SSAP cassette, the Exo cassette, and the MIR162 5'-junction polynucleotide donor DNA template into the *Agrobacterium* superbinary plasmid transformation vector (the lambda red vector).

All constructs are delivered from superbinary vectors in *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 µM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remained on Pre-Regeneration media for 7 days. Calli beginning to initiate shoots are transferred to Regeneration medium with 7.5 mg/L PPT in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the MIR162 junction sequence, using a PCR-based approach. The PCR primer on the 5'-end can be 5'-ttttatgtattatttggtccctaca-3' (SEQ ID NO: 33) and the PCR primer on the 3'-end is 5'-gtcgacggcgtt-taacaggctggca-3'(SEQ ID NO: 34). These primers that flank donor DNA homology arms are used to amplify the MIR162 5'-junction sequence. The correct donor sequence insertion will produce a 1579 bp product. Amplicons can be sequenced directly using an amplicon sequencing approach or ligated to a convenient plasmid vector for Sanger sequencing. Those plants in which the MIR162 5' junction polynucleotide sequence now contains the intended CgRRS (e.g., Cas12a recognition sequence in SEQ ID NO: 37) are selected and grown to maturity. The T-DNA encoding the Cas12a reagents can be segregated away from the modified junction sequence in a subsequent generation. The resultant INIR12 transgenic locus comprising the CgRRS and OgRRS (e.g. which each comprise SEQ ID NO: 27 and an operably linked PAM site) can be excised using Cas12a and a suitable gRNA which hybridizes to DNA comprising SEQ ID NO: 27 at both the OgRRS and the CgRRS.

Example 3. Deletion of the MIR162 PMI Gene Cassette

The ZmUbi1::PMI coding sequence in MIR162 transgenic maize performs no useful function with respect to field productivity. It can be removed using a Cas12a-mediated genomic DNA deletion approach. The procedure calls for creating an *Agrobacterium* transformation vector encoding the Cas12a nuclease, the MIR162 PMI 5' guide RNA (5'-taattcctaaaaccaaaatccag-3'; SEQ ID NO: 23), the MIR162 PMI 3' guide RNA (5'-ttgccaaatgtttgaacgatctg-3'; SEQ ID NO: 24), and a plant selectable marker gene.

A binary vector that contains a strong constitutive expression cassette like the ZmUbi1 promoter::ZmUbi1 terminator driving Cas12a, a PolII or PolII gene cassette driving the Cas12a gRNAs and a CaMV 35S:PAT:NOS or other suitable plant selectable marker is constructed. An expression cassette driving a fluorescent protein like mScarlet may also be useful to the plant transformation process and included in the binary vector.

The aforementioned binary vector is transformed into maize using the procedure essentially as outlined in Example 1. The regenerated plants can be screened with the primer set below to identify individuals that have lost the ZmUbi1::PMI fragment. The primers span 3820 bases in the intact insert. If both cuts occur and the ends are ligated together, this will produce a ~555 bp amplicon. This is verified by DNA sequence analysis. The primer set includes 162-PMI-ampseq-5' (5'-ggcaacaacctgtacggcggcccga-3'; SEQ ID NO: 35) and 162-PMI-ampseq-3' (5'-gttgccttcagac-catggcggacgt-3'; SEQ ID NO: 36).

The breadth and scope of the present disclosure should not be limited by any of the above-described embodiments.

What is claimed is:

1. A transgenic maize plant cell comprising a transgenic locus, wherein the transgenic locus comprises a modification of the original MIR162 transgenic locus comprising SEQ ID NO: 1 or the original MIR162 transgenic locus present in seed deposited at the ATCC under accession No. PTA-8166, wherein the transgenic locus comprises the first zmUbiInt promoter operably linked to the Vip3Aa gene, the CaMV35S terminator, and the NOS terminator of the original MIR162 transgenic locus comprising SEQ ID NO:1 or present in the seed deposited at the ATCC under accession No. PTA-8166, and wherein the modification comprises a deletion of the DNA molecule encoding the second ZmUbiInt promoter and operably linked phosphomannose isomerase coding region of the original MIR162 locus.

2. A transgenic maize plant seed comprising a transgenic locus, wherein the transgenic locus comprises a modification of the original_MIR162 transgenic locus comprising SEQ ID NO: 1 or the original MIR162 transgenic locus present in seed deposited at the ATCC under accession No. PTA-8166, wherein the transgenic locus comprises the first zmUbiInt promoter operably linked to the Vip3Aa gene, the CaMV35S terminator, and the NOS terminator of the original MIR162 transgenic locus comprising SEQ ID NO:1 or present in the seed deposited at the ATCC under accession No. PTA-8166, and wherein the modification comprises a deletion of the DNA molecule encoding the second ZmUbiInt promoter and operably linked phosphomannose isomerase coding region of the original MIR162 locus.

3. A transgenic maize plant comprising a transgenic locus, wherein the transgenic locus comprises a modification of the original MIR162 transgenic locus comprising SEQ ID NO: 1 or the original MIR162 transgenic locus present in seed deposited at the ATCC under accession No. PTA-8166, wherein the transgenic locus comprises the first zmUbiInt promoter operably linked to the Vip3Aa gene, the CaMV35S terminator, and the NOS terminator of the original MIR162 transgenic locus comprising SEQ ID NO:1 or present in the seed deposited at the ATCC under accession No. PTA-8166, and wherein the modification comprises a deletion of the DNA molecule encoding the second ZmUbiInt promoter and operably linked phosphomannose isomerase coding region of the original MIR162 locus.

4. A method for obtaining a bulked population of seed comprising selfing the transgenic maize plant of claim 3 and harvesting transgenic seed comprising the transgenic locus, wherein the transgenic locus comprises a modification of the original MIR162 transgenic locus comprising SEQ ID NO: 1 or the original MIR162 transgenic locus present in seed deposited at the ATCC under accession No. PTA-8166, wherein the transgenic locus comprises the first zmUbiInt promoter operably linked to the Vip3Aa gene, the CaMV35S terminator, and the NOS terminator of the original MIR162 transgenic locus comprising SEQ ID NO:1 or present in the seed deposited at the ATCC under accession No. PTA-8166, and wherein the modification comprises a deletion of a DNA molecule encoding the second ZmUbiInt promoter and operably linked phosphomannose isomerase coding region of the original MIR162 locus.

5. The transgenic maize plant cell of claim 1, wherein the transgenic locus further comprises a deletion of a DNA segment comprising non-essential transgenic DNA in a junction polynucleotide of the original MIR162 transgenic locus.

6. The transgenic maize plant cell of claim 5, wherein the deletion results in the 5' junction polynucleotide of SEQ ID NO: 40.

7. The transgenic maize plant cell of claim 6, wherein the transgenic locus comprises the DNA molecule of SEQ ID NO: 43.

8. The transgenic maize plant seed of claim 2, wherein the transgenic locus comprises the DNA molecule of SEQ ID NO: 43.

9. The transgenic maize plant of claim 3, wherein the transgenic locus comprises the DNA molecule of SEQ ID NO: 43.

10. The method of claim 4, wherein the transgenic locus comprises the DNA molecule of SEQ ID NO: 43.

* * * * *

SEQUENCE LISTING

<160> NUMBER OF SEQ ID NOS: 43

<210> SEQ ID NO 1
<211> LENGTH: 10579
<212> TYPE: DNA
<213> ORGANISM: Artificial
<220> FEATURE:
<223> OTHER INFORMATION: synthetic

<400> SEQUENCE: 1

| | | | | | |
|---|---|---|---|---|---|
| tcctgtgttg | ttggaacaga | cttctgtctc | ttctggtgat | cataaatatt | taaatgaacc | 60 |
| agttgtgttg | gaaatgttg | ttttcttttg | tctctagact | ggaaagcgga | gttctcgtca | 120 |
| acacggttct | ttcaactagg | gatgaaagtg | gtaatccgaa | ttgttagtac | aaatttaata | 180 |
| ttttaaaata | gatatgtata | aaattttatg | ttgatctttt | ttatgttatc | aagcacatta | 240 |
| gtataaatta | gtataaatat | gaataaaata | ttacataaaa | tgttttatgt | attatttggt | 300 |
| ccctacaaca | taaatagttg | aaaaaattac | taaatttgtt | ttcgaatcta | tatcgaagtt | 360 |
| tatatctatt | atttaagaaa | aatataggat | gaaaaggttt | atcttttatg | aatctttaca | 420 |
| agctggatct | tataaacaag | aaaataaatt | tatattgtag | attttatatc | ctatttattc | 480 |
| gcaatcaaag | aaaagcgact | aaaaaactga | ttaccgagta | aatactgttt | ccaaccgttt | 540 |
| tcgtccctac | tatcaacgcc | ttctcccaac | cgcagtcgat | ctgtccgtct | gtatcaggcg | 600 |
| cagcggcacc | cctgctgttc | gactatctag | accatagaat | attttaggta | tacaataatt | 660 |
| ttagttccac | gctagaacat | tttagttaga | ataataacaa | gatttgctat | tgatgtagga | 720 |
| ctcgcccgtc | actgtctaaa | aaagcattct | gtcggtctta | ttctttaggc | atcagcgggt | 780 |
| gtactatctc | attttcccta | tcatattcct | cagtactctg | ttaagtataa | atggtctatt | 840 |
| ttacatgatg | aactaataaa | actaattaag | gatcctaact | ttttgtgaag | gtaatttgga | 900 |
| tcattatgca | ttaccatcct | acgtatacct | gctgcagcag | catctgcgta | agcacagcct | 960 |
| agatatatgc | ttctgtgtgg | actgaaagga | gactttgttt | atcaattagt | atactcccaa | 1020 |
| aaaactgatg | acaccaatga | tgcaaatagg | ctgggaatag | tctgtctaat | agtttgagtg | 1080 |
| aatcatgtca | ctgatagttt | aaactgaagg | cgggaaacga | caatctgatc | atgagcggag | 1140 |
| aattaaggga | gtcacgttat | gacccccgcc | gatgacgcgg | gacaagccgt | tttacgtttg | 1200 |
| gaactgacag | aaccgcaacg | ttgaaggagc | cactcagcaa | gctggtacaa | gcttgcatgc | 1260 |
| ctgcagtgca | gcgtgacccg | gtcgtgcccc | tctctagaga | taatgagcat | tgcatgtcta | 1320 |
| agttataaaa | aattaccaca | tatttttttt | gtcacacttg | tttgaagtgc | agtttatcta | 1380 |
| tctttataca | tatatttaaa | ctttactcta | cgaataatat | aatctatagt | actacaataa | 1440 |
| tatcagtgtt | ttagagaatc | atataaatga | acagttagac | atggtctaaa | ggacaattga | 1500 |
| gtattttgac | aacaggactc | tacagtttta | tcttttagt | gtgcatgtgt | tctccttttt | 1560 |
| ttttgcaaat | agcttcacct | atataatact | tcatccattt | tattagtaca | tccatttagg | 1620 |
| gtttagggtt | aatggttttt | atagactaat | tttttagta | catctatttt | attctatttt | 1680 |
| agcctctaaa | ttaagaaaac | taaaactcta | ttttagtttt | tttattaat | aatttagata | 1740 |
| taaaatagaa | taaaataaag | tgactaaaaa | ttaaacaaat | acccttaag | aaattaaaaa | 1800 |
| aactaaggaa | acatttttct | tgtttcgagt | agataatgcc | agcctgttaa | acgccgtcga | 1860 |
| cgagtctaac | ggacaccaac | cagcgaacca | gcagcgtcgc | gtcgggccaa | gcgaagcaga | 1920 |
| cggcacggca | tctctgtcgc | tgcctctgga | cccctctcga | gagttccgct | ccaccgttgg | 1980 |
| acttgctccg | ctgtcggcat | ccagaaattg | cgtggcggag | cggcagacgt | gagccggcac | 2040 |

```
ggcaggcggc ctcctcctcc tctcacggca ccggcagcta cggggggattc ctttcccacc    2100 gctccttcgc tttcccttcc tcgcccgccg taataaatag acaccccctc cacaccctct    2160
ttccccaacc tcgtgttgtt cggagcgcac acacacacaa ccagatctcc cccaaatcca    2220
cccgtcggca cctccgcttc aaggtacgcc gctcgtcctc ccccccccccc cctctctacc    2280 ttctctagat cggcgttccg gtccatggtt agggcccggt agttctactt ctgttcatgt    2340
ttgtgttaga tccgtgtttg tgttagatcc gtgctgctag cgttcgtaca cggatgcgac    2400
ctgtacgtca gacacgttct gattgctaac ttgccagtgt ttctctttgg ggaatcctgg    2460
gatggctcta gccgttccgc agacgggatc gatttcatga ttttttttgt ttcgttgcat    2520
agggtttggt ttgcccttt cctttatttc aatatatgcc gtgcacttgt ttgtcgggtc    2580
atcttttcat gcttttttt gtcttggttg tgatgatgtg gtctggttgg gcggtcgttc    2640
tagatcggag tagaattctg tttcaaacta cctggtggat ttattaattt tggatctgta    2700
tgtgtgtgcc atacatattc atagttacga attgaagatg atggatggaa atatcgatct    2760
aggataggta tacatgttga tgcgggtttt actgatgcat atacagagat gcttttgtt    2820 cgcttggttg tgatgatgtg gtgtggttgg gcggtcgttc attcgttcta gatcggagta    2880
gaatactgtt tcaaactacc tggtgtattt attaattttg gaactgtatg tgtgtgtcat    2940
acatcttcat agttacgagt ttaagatgga tggaaatatc gatctaggat aggtatacat    3000
gttgatgtgg gttttactga tgcatataca tgatggcata tgcagcatct attcatatgc    3060
tctaaccttg agtacctatc tattataata aacaagtatg ttttataatt attttgatct    3120
tgatatactt ggatgatggc atatgcagca gctatatgtg gatttttta gccctgcctt    3180 catacgctat ttatttgctt ggtactgttt cttttgtcga tgctcaccct gttgtttggt    3240
gttacttctg caggtcgact ctagaggatc caccatgaac aagaacaaca ccaagctgag    3300
cacccgcgcc ctgccgagct tcatcgacta cttcaacggc atctacgct cgccaccgg    3360 catcaaggac atcatgaaca tgatcttcaa gaccgacacc ggcggcgacc tgaccctgga    3420
cgagatcctg aagaaccagc agctgctgaa cgacatcagc ggcaagctgg acggcgtgaa    3480
cggcagcctg aacgacctga tcgcccaggg caacctgaac accgagctga gcaaggagat    3540
ccttaagatc gccaacgagc agaaccaggt gctgaacgac gtgaacaaca agctggacgc    3600
catcaacacc atgctgcgcg tgtacctgcc gaagatcacc agcatgctga gcgacgtgat    3660
gaagcagaac tacgccctga gcctgcagat cgagtacctg agcaagcagc tgcaggagat    3720
cagcgacaag ctggacatca tcaacgtgaa cgtcctgatc aacagcaccc tgaccgagat    3780 cacccccggcc taccagcgca tcaagtacgt gaacgagaag ttcgaagagc tgaccttcgc    3840
caccgagacc agcagcaagg tgaagaagga cggcagcccg gccgacatcc tggacgagct    3900
gaccgagctg accgagctgg cgaagagcgt gaccaagaac gacgtggacg gcttcgagtt    3960
ctacctgaac accttccacg acgtgatggt gggcaacaac ctgttcggcc gcagcgccct    4020
gaagaccgcc agcgagctga tcaccaagga gaacgtgaag accagcggca gcgaggtggg    4080
caacgtgtac aacttcctga tcgtgctgac cgccctgcag gcccaggcct tcctgaccct    4140
gaccacctgt cgcaagctgc tgggcctggc cgacatcgac tacaccagca tcatgaacga    4200
gcacttgaac aaggagaagg aggagttccg cgtgaacatc ctgccgaccc tgagcaacac    4260
cttcagcaac ccgaactacg ccaaggtgaa gggcagcgac gaggacgcca agatgatcgt    4320
ggaggctaag ccgggccacg cgttgatcgg cttcgagatc agcaacgaca gcatcaccgt    4380
```

```
gctgaaggtg tacgaggcca agctgaagca gaactaccag gtggacaagg acagcttgag    4440
cgaggtgatc tacggcgaca tggacaagct gctgtgtccg gaccagagcg agcaaatcta    4500
ctacaccaac aacatcgtgt tcccgaacga gtacgtgatc accaagatcg acttcaccaa    4560
gaagatgaag accctgcgct acgaggtgac cgccaacttc tacgcagca gcaccggcga     4620 gatcgacctg aacaagaaga aggtggagag cagcgaggcc gagtaccgca ccctgagcgc    4680
gaacgacgac ggcgtctaca tgccactggg cgtgatcagc gagaccttcc tgaccccgat    4740
caacggcttt ggcctgcagg ccgacgagaa cagccgcctg atcaccctga cctgtaagag    4800
ctacctgcgc gagctgctgc tagccaccga cctgagcaac aaggagacca agctgatcgt    4860
gccaccgagc ggcttcatca gcaacatcgt ggagaacggc agcatcgagg aggacaacct    4920
ggagccgtgg aaggccaaca caagaacgc ctacgtggac cacaccggcg gcgtgaacgg     4980
caccaaggcc ctgtacgtgc acaaggacgg cggcatcagc cagttcatcg gcgacaagct    5040
gaagccgaag accgagtacg tgatccagta caccgtgaag ggcaagccat cgattcacct    5100
gaaggacgag aacaccggct acatccacta cgaggacacc aacaacaacc tggaggacta    5160
ccagaccatc aacaagcgct tcaccaccgg caccgacctg aagggcgtgt acctgatcct    5220
gaagagccag aacggcgacg aggcctgggg cgacaacttc atcatcctgg agatcagccc    5280
gagcgagaag ctgctgagcc cggagctgat caacaccaac aactggacca gcaccggcag    5340
caccaacatc agcggcaaca ccctgaccct gtaccagggc ggccgcggca tcctgaagca    5400
gaacctgcag ctggacagct tcagcaccta ccgcgtgtac ttcagcgtga gcggcgacgc    5460
caacgtgcgc atccgcaact cccgcgaggt gctgttcgag aagaggtaca tgagcggcgc    5520
caaggacgtg agcgagatgt tcaccaccaa gttcgagaag acaacttct acatcgagct     5580 gagccagggc aacaacctgt acggcggccc gatcgtgcac ttctacgacg tgagcatcaa    5640
gtaggagctc tagatctgtt ctgcacaaag tggagtagtc agtcatcgat caggaaccag    5700
acaccagact tttattcata cagtgaagtg aagtgaagtg cagtgcagtg agttgctggt    5760
ttttgtacaa cttagtatgt atttgtattt gtaaaatact tctatcaata aaatttctaa    5820
ttcctaaaac caaaatccag gggtaccagc ttgcatgcct gcagtgcagc gtgacccggt    5880
cgtgcccctc tctagagata atgagcattg catgtctaag ttataaaaaa ttaccacata    5940 tttttttgt cacacttgtt tgaagtgcag tttatctatc tttatacata tatttaaact     6000
ttactctacg aataatataa tctatagtac tacaataata tcagtgtttt agagaatcat    6060
ataaatgaac agttagacat ggtctaaagg acaattgagt attttgacaa caggactcta    6120
cagttttatc tttttagtgt gcatgtgttc tcctttttt ttgcaaatag cttcacctat     6180
ataatacttc atccatttta ttagtacatc catttagggt ttagggttaa tggttttat     6240 agactaattt ttttagtaca tctattttat tctattttag cctctaaatt aagaaaacta    6300
aaactctatt ttagtttttt tatttaataa tttagatata aaatagaata aaataaagtg    6360
actaaaaatt aaacaaatac cctttaagaa attaaaaaaa ctaaggaaac atttttcttg    6420
tttcgagtag ataatgccag cctgttaaac gccgtcgacg agtctaacgg acaccaacca    6480
gcgaaccagc agcgtcgcgt cgggccaagc gaagcagacg gcacggcatc tctgtcgctg    6540
cctctggacc cctctcgaga gttccgctcc accgttggac ttgctccgct gtcggcatcc    6600
agaaattgcg tggcggagcg gcagacgtga gccggcacgg caggcggcct cctcctcctc    6660
tcacggcacc ggcagctacg ggggattcct ttcccaccgc tccttcgctt tcccttcctc    6720
gcccgccgta ataaatagac accccctcca caccctcttt ccccaacctc gtgttgttcg    6780
```

```
gagcgcacac acacacaacc agatctcccc caaatccacc cgtcggcacc tccgcttcaa    6840
ggtacgccgc tcgtcctccc ccccccccc  tctctacctt ctctagatcg gcgttccggt    6900
ccatggttag ggcccggtag ttctacttct gttcatgttt gtgttagatc cgtgtttgtg    6960
ttagatccgt gctgctagcg ttcgtacacg gatgcgacct gtacgtcaga cacgttctga    7020
ttgctaactt gccagtgttt ctctttgggg aatcctggga tggctctagc cgttccgcag    7080
acgggatcga tttcatgatt ttttttgttt cgttgcatag ggtttggttt gcccttttcc    7140
tttatttcaa tatatgccgt gcacttgttt gtcgggtcat cttttcatgc ttttttttgt    7200
cttggttgtg atgatgtggt ctggttgggc ggtcgttcta gatcggagta gaattctgtt    7260
tcaaactacc tggtggattt attaatttg  gatctgtatg tgtgtgccat acatattcat    7320
agttacgaat tgaagatgat ggatggaaat atcgatctag gataggtata catgttgatg    7380
cgggttttac tgatgcatat acagagatgc ttttgttcg  cttggttgtg atgatgtggt    7440
gtggttgggc ggtcgttcat tcgttctaga tcggagtaga atactgtttc aaactacctg    7500
gtgtatttat taattttgga actgtatgtg tgtgtcatac atcttcatag ttacgagttt    7560
aagatggatg gaaatatcga tctaggatag gtatacatgt tgatgtgggt tttactgatg    7620
catatacatg atggcatatg cagcatctat tcatatgctc taaccttgag tacctatcta    7680
ttataataaa caagtatgtt ttataattat tttgatcttg atatacttgg atgatggcat    7740
atgcagcagc tatatgtgga ttttttagc  cctgccttca tacgctattt atttgcttgg    7800
tactgtttct tttgtcgatg ctcaccctgt tgtttggtgt tacttctgca gggatccccg    7860
atcatgcaaa aactcattaa ctcagtgcaa aactatgcct ggggcagcaa aacggcgttg    7920
actgaacttt atggtatgga aaatccgtcc agccagccga tggccgagct gtggatgggc    7980
gcacatccga aaagcagttc acgagtgcag aatgccgccg gagatatcgt ttcactgcgt    8040
gatgtgattg agagtgataa atcgactctg ctcggagagg ccgttgccaa acgctttggc    8100
gaactgcctt tcctgttcaa agtattatgc gcagcacagc cactctccat tcaggttcat    8160
ccaaacaaac acaattctga atcggtttt  gccaaagaaa atgccgcagg tatcccgatg    8220
gatgccgccg agcgtaacta taaagatcct aaccacaagc cggagctggt ttttgcgctg    8280
acgcctttcc ttgcgatgaa cgcgtttcgt gaattttccg agattgtctc cctactccag    8340
ccggtcgcag gtgcacatcc ggcgattgct cactttttac aacagcctga tgccgaacgt    8400
ttaagcgaac tgttcgccag cctgttgaat atgcagggtg aagaaaaatc ccgcgcgctg    8460 gcgatttaa  atcggccct  cgatagccag cagggtgaac cgtggcaaac gattcgttta    8520
atttctgaat tttacccgga agacagcggt ctgttctccc cgctattgct gaatgtggtg    8580
aaattgaacc ctggcgaagc gatgttcctg ttcgctgaaa caccgcacgc ttacctgcaa    8640
ggcgtggcgc tggaagtgat ggcaaactcc gataacgtgc tgcgtgcggg tctgacgcct    8700
aaatacattg atattccgga actggttgcc aatgtgaaat cgaagccaa  accggctaac    8760 cagttgttga cccagccggt gaaacaaggt gcagaactgg acttcccgat tccagtggat    8820
gattttgcct tctcgctgca tgaccttagt gataaagaaa ccaccattag ccagcagagt    8880
gccgccattt tgttctgcgt cgaaggcgat gcaacgttgt ggaaaggttc tcagcagtta    8940
cagcttaaac cgggtgaatc agcgtttatt gccgccaacg aatcaccggt gactgtcaaa    9000
ggccacggcc gttagcgcg  tgtttacaac aagctgtaag agcttactga aaaaattaac    9060
atctcttgct aagctgggag ctcgatccgt cgacctgcag atcgttcaaa catttggcaa    9120
```

```
taaagtttct taagattgaa tcctgttgcc ggtcttgcga tgattatcat ataatttctg    9180
ttgaattacg ttaagcatgt aataattaac atgtaatgca tgacgttatt tatgagatgg    9240
gtttttatga ttagagtccc gcaattatac atttaatacg cgatagaaaa caaaatatag    9300
cgcgcaaact aggataaatt atcgcgcgcg tgtcatcta tgttactaga tccccgggtc     9360
tagacaattc agtacattaa aaacgtccgc catggtctga aggcaacaga taaggcatac    9420
tgggccttgt ggtagttgtt ttactgggcc ttttttgtatg atctataaaa ttcactggga   9480
tcaacccgga gaggaatggc agcagatgca gtccccaggg tcctccgtcg ccgcctgagc    9540
acccggcacc cgcgctgaac cggagaggga cgcgcggacg ccgtgcagct ggtgcggagg    9600
gggctgtggc agatgaggat gagacgcgta cgtggctggg aaggccagca ggccaccggg    9660
tcttcgtcca gcccggcgcg agtggacagg actagagatg gcaacggtta caaacccgct    9720
gggttttacc gtcccaaacc cgtacccgtg aaaaatatct atgcccatta aaaaacccgt    9780
acccatgacg ggtttgagat tttgcccaaa cccgtaccca tcgggttaac gggtacccat    9840
gggttacccg cgggtttcat ctccaatata cctgttcttc tcataatcaa taagtatcgt    9900
aatgattaat gatatcatga tccaaaatct atgtaatgaa caacgagttc atgatttggt    9960
ataaaaatta ttagtagaga gaatgaaata caaataataa gttgtataat taagtgacct   10020
tgcactaagt tatccatcca tcacatatat aacgctagta aaaactataa tatcaagcaa   10080
gcaacactct caccgactac tgatacattc accaattgat aaaaaatatg aagtaaataa   10140
ggaataacaa gtttgttgtt cgtttataaa ataaaatgac aatatgcact aggtttggtc   10200
gggtttaaaa aacccacggg ttcacggggt tgggtactat aggaacaaac ccgtacccat   10260
aaacccattg ggtacagatt tatgcccgtt aacaaaccca tgggtatgaa aattgaccca   10320
aacctatacc ctaatggggt aaaaacccat cgggtttcgg atttcgggta cccattgcca   10380
tctctagaca ggacaaccct ggccggtcct gtatgtaggc caccagcatc ggccagttgg   10440
tacatccagc cggggtcagg tcacttttac tcgtctcaat cagacaatca ccgtccacca   10500
acgaacgcca acgttgtcac ttgtcaggtc ggttgagact tgtattttttt tttgtcctcc   10560 gtaaaaatcg gttcaccag                                                10579
```

<210> SEQ ID NO 2
<211> LENGTH: 7314
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (5831)..(5842)
<223> OTHER INFORMATION: n is absent or is a, c, g, or t

<400> SEQUENCE: 2

```
tcctgtgttg ttggaacaga cttctgtctc ttctggtgat cataaatatt taaatgaacc      60
agttgtgttg gaaaatgttg ttttcttttg tctctagact ggaaagcgga gttctcgtca     120
acacggttct ttcaactagg gatgaaagtg gtaatccgaa ttgttagtac aaatttaata     180
ttttaaaata gatatgtata aaattttatg ttgatctttt ttatgttatc aagcacatta     240
gtataaatta gtataaatat gaataaaata ttacataaaa tgtttatgt attatttggt      300 ccctacaaca taaatagttg aaaaaattac taaatttgtt ttcgaatcta tatcgaagtt     360
tatatctatt atttaagaaa aatataggat gaaaaggttt atcttttatg aatctttaca     420
agctggatct tataaacaag aaaataaatt tatattgtag attttatatc ctatttattc     480
```

```
gcaatcaaag aaaagcgact aaaaaactga ttaccgagta aatactgttt ccaaccgttt    540
tcgtccctac tatcaacgcc ttctcccaac cgcagtcgat ctgtccgtct gtatcaggcg    600
cagcggcacc cctgctgttc gactatctag accatagaat attttaggta tacaataatt    660
ttagttccac gctagaacat tttagttaga ataataacaa gatttgctat tgatgtagga    720
ctcgcccgtc actgtctaaa aaagcattct gtcggtctta ttctttaggc atcagcggt    780 gtactatctc attttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga ctttgtttt atcaattagt atactcccaa   1020
aaaactgatg acaccaatga tgcaaatagg ctgggaatag tctgtctaat agtttgagtg   1080
aatcatgtca ctgatagttt aaactgaagg cgggaaacga caatctgatc atgagcggag   1140
aattaaggga gtcacgttat gaccccgcc gatgacgcgg gacaagccgt tttacgtttg   1200
gaactgacag aaccgcaacg ttgaaggagc cactcagcaa gctggtacaa gcttgcatgc   1260
ctgcagtgca gcgtgacccg tcgtgcccc tctctagaga taatgagcat tgcatgtcta   1320
agttataaaa aattaccaca tattttttt gtcacacttg tttgaagtgc agtttatcta   1380
tctttataca tatatttaaa ctttactcta cgaataatat aatctatagt actacaataa   1440
tatcagtgtt ttagagaatc atataaatga acagttagac atggtctaaa ggacaattga   1500
gtattttgac aacaggactc tacagtttta tcttttagt gtgcatgtgt tctcctttt    1560 ttttgcaaat agcttcacct atataatact tcatccattt tattagtaca tccatttagg   1620
gtttagggtt aatggttttt atagactaat ttttttagta catctatttt attctatttt   1680
agcctctaaa ttaagaaaac taaaactcta ttttagttt tttatttaat aatttagata   1740
taaaatagaa taaaataaag tgactaaaaa ttaaacaaat acccttaag aaattaaaa    1800 aactaaggaa acattttct tgtttcgagt agataatgcc agcctgttaa acgccgtcga   1860
cgagtctaac ggacaccaac cagcgaacca gcagcgtcgc gtcgggccaa gcgaagcaga   1920
cggcacggca tctctgtcgc tgcctctgga cccctctcga gagttccgct ccaccgttgg   1980
acttgctccg ctgtcggcat ccagaaattg cgtggcggag cggcagacgt gagccggcac   2040
ggcaggcggc ctcctcctcc tctcacggca ccggcagcta cggggattc ctttccccacc   2100 gctccttcgc tttcccttcc tcgcccgccg taataaatag acaccccctc cacaccctct   2160
ttccccaacc tcgtgttgtt cggagcgcac acacacacaa ccagatctcc cccaaatcca   2220
cccgtcggca cctccgcttc aaggtacgcc gctcgtcctc ccccccccc cctctctacc   2280 ttctctagat cggcgttccg gtccatggtt agggccccggt agttctactt ctgttcatgt   2340
ttgtgttaga tccgtgttg tgttagatcc gtgctgctag cgttcgtaca cggatgcgac   2400
ctgtacgtca gacacgttct gattgctaac ttgccagtgt ttctctttgg ggaatcctgg   2460
gatggctcta gccgttccgc agacgggatc gatttcatga ttttttttgt ttcgttgcat   2520
agggtttggt ttgcccttt cctttatttc aatatatgcc gtgcacttgt ttgtcgggtc   2580
atcttttcat gcttttttt gtcttggttg tgatgatgtg gtctggttgg gcggtcgttc   2640
tagatcggag tagaattctg tttcaaacta cctggtggat ttattaattt tggatctgta   2700
tgtgtgtgcc atacatattc atagttacga attgaagatg atggatggaa atatcgatct   2760
aggataggta tacatgttga tgcgggtttt actgatgcat atacagagat gcttttgtt    2820
```

```
cgcttggttg tgatgatgtg gtgtggttgg gcggtcgttc attcgttcta gatcggagta    2880
gaatactgtt tcaaactacc tggtgtattt attaattttg gaactgtatg tgtgtgtcat    2940
acatcttcat agttacgagt ttaagatgga tggaaatatc gatctaggat aggtatacat    3000
gttgatgtgg gttttactga tgcatataca tgatggcata tgcagcatct attcatatgc    3060
tctaaccttg agtacctatc tattataata aacaagtatg ttttataatt attttgatct    3120
tgatatactt ggatgatggc atatgcagca gctatatgtg gatttttta gcccthgcctt    3180 catacgctat ttatttgctt ggtactgttt cttttgtcga tgctcaccct gttgtttggt    3240
gttacttctg caggtcgact ctagaggatc caccatgaac aagaacaaca ccaagctgag    3300
cacccgcgcc ctgccgagct tcatcgacta cttcaacggc atctacggct cgccaccgg    3360 catcaaggac atcatgaaca tgatcttcaa gaccgacacc ggcggcgacc tgaccctgga    3420
cgagatcctg aagaaccagc agctgctgaa cgacatcagc ggcaagctgg acggcgtgaa    3480
cggcagcctg aacgacctga tcgcccaggg caacctgaac accgagctga caaggagat    3540 ccttaagatc gccaacgagc agaaccaggt gctgaacgac gtgaacaaca agctggacgc    3600
catcaacacc atgctgcgcg tgtacctgcc gaagatcacc agcatgctga gcgacgtgat    3660
gaagcagaac tacgccctga gcctgcagat cgagtacctg agcaagcagc tgcaggagat    3720
cagcgacaag ctggacatca tcaacgtgaa cgtcctgatc aacagcaccc tgaccgagat    3780
caccccggcc taccagcgca tcaagtacgt gaacgagaag ttcgaagagc tgaccttcgc    3840
caccgagacc agcagcaagg tgaagaagga cggcagcccg gccgacatcc tggacgagct    3900
gaccgagctg accgagctgg cgaagagcgt gaccaagaac gacgtggacg gcttcgagtt    3960
ctacctgaac accttccacg acgtgatggt gggcaacaac ctgttcggcc gcagcgccct    4020
gaagaccgcc agcgagctga tcaccaagga gaacgtgaag accagcggca gcgaggtggg    4080
caacgtgtac aacttcctga tcgtgctgac cgccctgcag gcccaggcct tcctgaccct    4140 gaccaccctgt cgcaagctgc tgggcctggc cgacatcgac tacaccagca tcatgaacga    4200
gcacttgaac aaggagaagg aggagttccg cgtgaacatc ctgccgaccc tgagcaacac    4260
cttcagcaac ccgaactacg ccaaggtgaa gggcagcgac gaggacgcca agatgatcgt    4320
ggaggctaag ccgggccacg cgttgatcgg cttcgagatc agcaacgaca gcatcaccgt    4380
gctgaaggtg tacgaggcca agctgaagca gaactaccag gtggacaagg acagcttgag    4440
cgaggtgatc tacggcgaca tggacaagct gctgtgtccg gaccagagcg agcaaatcta    4500
ctacaccaac aacatcgtgt cccgaacga gtacgtgatc accaagatcg acttcaccaa    4560
gaagatgaag accctgcgct acgaggtgac cgccaacttc tacgacagca gcaccggcga    4620
gatcgacctg aacaagaaga aggtggagag cagcgaggcc gagtaccgca ccctgagcgc    4680
gaacgacgac ggcgtctaca tgccactggg cgtgatcagc gagaccttcc tgaccccgat    4740
caacggcttt ggcctgcagg ccgacgagaa cagccgcctg atcaccctga cctgtaagag    4800
ctacctgcgc gagctgctgc tagccaccga cctgagcaac aaggagacca agctgatcgt    4860
gccaccgagc ggcttcatca gcaacatcgt ggagaacggc agcatcgagg aggacaacct    4920
ggagccgtgg aaggccaaca acaagaacgc ctacgtggac cacaccggcg gcgtgaacgg    4980
caccaaggcc ctgtacgtgc acaaggacgg cggcatcagc cagttcatcg gcgacaagct    5040
gaagccgaag accgagtacg tgatccagta caccgtgaag ggcaagccat cgattcacct    5100
gaaggacgag aacaccggct acatccacta cgaggacacc aacaacaacc tggaggacta    5160
ccagaccatc aacaagcgct tcaccaccgg caccgacctg aagggcgtgt acctgatcct    5220
```

```
gaagagccag aacggcgacg aggcctgggg cgacaacttc atcatcctgg agatcagccc    5280
gagcgagaag ctgctgagcc cggagctgat caacaccaac aactggacca gcaccggcag    5340
caccaacatc agcggcaaca ccctgaccct gtaccagggc ggccgcggca tcctgaagca    5400
gaacctgcag ctggacagct tcagcaccta ccgcgtgtac ttcagcgtga gcggcgacgc    5460
caacgtgcgc atccgcaact cccgcgaggt gctgttcgag aagaggtaca tgagcggcgc    5520
caaggacgtg agcgagatgt tcaccaccaa gttcgagaag gacaacttct acatcgagct    5580
gagccagggc aacaacctgt acggcggccc gatcgtgcac ttctacgacg tgagcatcaa    5640
gtaggagctc tagatctgtt ctgcacaaag tggagtagtc agtcatcgat caggaaccag    5700
acaccagact tttattcata cagtgaagtg aagtgaagtg cagtgcagtg agttgctggt    5760
ttttgtacaa cttagtatgt atttgtattt gtaaaatact tctatcaata aaatttctaa    5820
ttcctaaaac nnnnnnnnnn nnaaacattt ggcaataaag tttcttaaga ttgaatcctg    5880
ttgccggtct tgcgatgatt atcatataat ttctgttgaa ttcgttaag catgtaataa    5940
ttaacatgta atgcatgacg ttatttatga gatgggtttt tatgattaga gtcccgcaat    6000
tatacattta atacgcgata gaaaacaaaa tatagcgcgc aaactaggat aaattatcgc    6060
gcgcggtgtc atctatgtta ctagatcccc gggtctagac aattcagtac attaaaaacg    6120
tccgccatgg tctgaaggca acagataagg catactgggc cttgtggtag ttgtttttact    6180
gggccttttt gtatgatcta taaaattcac tgggatcaac ccggagagga atggcagcag    6240
atgcagtccc cagggtcctc cgtcgccgcc tgagcacccg gcacccgcgc tgaaccggag    6300
agggacgcgc ggacgccgtg cagctggtgc ggagggggct gtggcagatg aggatgagac    6360
gcgtacgtgg ctgggaaggc cagcaggcca ccgggtcttc gtccagcccg gcgcgagtgg    6420
acaggactag agatggcaac ggttacaaac ccgctgggtt ttaccgtccc aaacccgtac    6480
ccgtgaaaaa tatctatgcc cattaaaaaa cccgtaccca tgacgggttt gagattttgc    6540
ccaaacccgt acccatcggg ttaacgggta cccatgggtt acccgcgggt tcatctcca    6600
atatacctgt tcttctcata atcaataagt atcgtaatga ttaatgatat catgatccaa    6660
aatctatgta atgaacaacg agttcatgat ttggtataaa aattattagt agagagaatg    6720
aaatacaaat aataagttgt ataattaagt gaccttgcac taagttatcc atccatcaca    6780
tataacgc tagtaaaaac tataatatca agcaagcaac actctcaccg actactgata    6840
cattcaccaa ttgataaaaa atatgaagta aataaggaat aacaagtttg ttgttcgttt    6900
ataaaataaa atgacaatat gcactaggtt tggtcgggtt taaaaaaccc acgggttcac    6960
gggtttgggt actataggaa caaacccgta cccataaacc cattgggtac agatttatgc    7020
ccgttaacaa acccatgggt atgaaaattg acccaaacct atacctaat gggtaaaaa    7080
cccatcgggt ttcggatttc gggtacccat tgccatctct agacaggaca acctcggccg    7140
gtcctgtatg taggccacca gcatcggcca gttggtacat ccagccgggg tcaggtcact    7200
tttactcgtc tcaatcagac aatcaccgtc caccaacgaa cgccaacgtt gtcacttgtc    7260
aggtcggttg agacttgtat ttttttttgt cctccgtaaa aatcggttca ccag         7314
```

<210> SEQ ID NO 3
<211> LENGTH: 7314
<212> TYPE: DNA
<213> ORGANISM: Artificial
<220> FEATURE:
<223> OTHER INFORMATION: synthetic
<220> FEATURE:

```
<221> NAME/KEY: misc_feature
<222> LOCATION: (1081)..(1104)
<223> OTHER INFORMATION: n is absent or is a, c, g, or t
<220> FEATURE:
<221> NAME/KEY: misc_feature
<222> LOCATION: (5831)..(5842)
<223> OTHER INFORMATION: n is absent or is a, c, g, or t

<400> SEQUENCE: 3
```

| | | | | |
|---|---|---|---|---|
| tcctgtgttg | ttggaacaga | cttctgtctc | ttctggtgat | cataaatatt | taaatgaacc | 60 |
| agttgtgttg | gaaatgttg | ttttcttttg | tctctagact | ggaaagcgga | gttctcgtca | 120 |
| acacggttct | ttcaactagg | gatgaaagtg | gtaatccgaa | ttgttagtac | aaatttaata | 180 |
| ttttaaaata | gatatgtata | aaattttatg | ttgatctttt | ttatgttatc | aagcacatta | 240 |
| gtataaatta | gtataaatat | gaataaaata | ttacataaaa | tgttttatgt | attatttggt | 300 |
| ccctacaaca | taaatagttg | aaaaaattac | taaatttgtt | ttcgaatcta | tatcgaagtt | 360 |
| tatatctatt | atttaagaaa | aatataggat | gaaaaggttt | atcttttatg | aatctttaca | 420 |
| agctggatct | tataaacaag | aaaataaatt | tatattgtag | attttatatc | ctatttattc | 480 |
| gcaatcaaag | aaaagcgact | aaaaaactga | ttaccgagta | aatactgttt | ccaaccgttt | 540 |
| tcgtccctac | tatcaacgcc | ttctcccaac | cgcagtcgat | ctgtccgtct | gtatcaggcg | 600 |
| cagcggcacc | cctgctgttc | gactatctag | accatagaat | attttaggta | tacaataatt | 660 |
| ttagttccac | gctagaacat | tttagttaga | ataataacaa | gatttgctat | tgatgtagga | 720 |
| ctcgcccgtc | actgtctaaa | aaagcattct | gtcggtctta | ttctttaggc | atcagcgggt | 780 |
| gtactatctc | atttttccta | tcatattcct | cagtactctg | ttaagtataa | atggtctatt | 840 |
| ttacatgatg | aactaataaa | actaattaag | gatcctaact | ttttgtgaag | gtaatttgga | 900 |
| tcattatgca | ttaccatcct | acgtatacct | gctgcagcag | catctgcgta | agcacagcct | 960 |
| agatatatgc | ttctgtgtgg | actgaaagga | gactttgttt | atcaattagt | atactcccaa | 1020 |
| aaaactgatg | acaccaatga | tgcaaatagg | ctgggaatag | tctgtctaat | agtttgagtg | 1080 |
| nnnnnnnnnn | nnnnnnnnnn | nnnntgaagg | cgggaaacga | caatctgatc | atgagcggag | 1140 |
| aattaaggga | gtcacgttat | gacccccgcc | gatgacgcgg | gacaagccgt | tttacgtttg | 1200 |
| gaactgacag | aaccgcaacg | ttgaaggagc | cactcagcaa | gctggtacaa | gcttgcatgc | 1260 |
| ctgcagtgca | gcgtgacccg | gtcgtgcccc | tctctagaga | taatgagcat | tgcatgtcta | 1320 |
| agttataaaa | aattaccaca | tatttttttt | gtcacacttg | tttgaagtgc | agtttatcta | 1380 |
| tctttataca | tatatttaaa | ctttactcta | cgaataatat | aatctatagt | actacaataa | 1440 |
| tatcagtgtt | ttagagaatc | atataaatga | acagttagac | atggtctaaa | ggacaattga | 1500 |
| gtattttgac | aacaggactc | tacagtttta | tctttttagt | gtgcatgtgt | tctccttttt | 1560 |
| ttttgcaaat | agcttcacct | atataatact | tcatccattt | tattagtaca | tccatttagg | 1620 |
| gtttagggtt | aatggttttt | atagactaat | ttttttagta | catctatttt | attctatttt | 1680 |
| agcctctaaa | ttaagaaaac | taaaactcta | ttttagtttt | tttatttaat | aatttagata | 1740 |
| taaaatagaa | taaaataaag | tgactaaaaa | ttaaacaaat | acccctttaag | aaattaaaaa | 1800 |
| aactaaggaa | acattttctc | tgtttcgagt | agataatgcc | agcctgttaa | acgccgtcga | 1860 |
| cgagtctaac | ggacaccaac | cagcgaacca | gcagcgtcgc | gtcgggccaa | gcgaagcaga | 1920 |
| cggcacggca | tctctgtcgc | tgcctctgga | cccctctcga | gagttccgct | ccaccgttgg | 1980 |
| acttgctccg | ctgtcggcat | ccagaaaattg | cgtggcggag | cggcagacgt | gagccggcac | 2040 |
| ggcaggcggc | ctcctcctcc | tctcacggca | ccggcagcta | cggggattc | ctttcccacc | 2100 |

```
gctccttcgc tttcccttcc tcgcccgccg taataaatag acaccccctc cacaccctct    2160
ttccccaacc tcgtgttgtt cggagcgcac acacacacaa ccagatctcc cccaaatcca    2220
cccgtcggca cctccgcttc aaggtacgcc gctcgtcctc cccccccccc cctctctacc    2280
ttctctagat cggcgttccg gtccatggtt agggcccggt agttctactt ctgttcatgt    2340
ttgtgttaga tccgtgtttg tgttagatcc gtgctgctag cgttcgtaca cggatgcgac    2400
ctgtacgtca gacacgttct gattgctaac ttgccagtgt ttctctttgg ggaatcctgg    2460
gatggctcta gccgttccgc agacgggatc gatttcatga ttttttttgt ttcgttgcat    2520
agggtttggt ttgcccttt cctttatttc aatatatgcc gtgcacttgt ttgtcgggtc    2580
atcttttcat gcttttttt gtcttggttg tgatgatgtg gtctggttgg gcggtcgttc    2640
tagatcggag tagaattctg tttcaaacta cctggtggat ttattaattt tggatctgta    2700
tgtgtgtgcc atacatattc atagttacga attgaagatg atggatggaa atatcgatct    2760
aggataggta tacatgttga tgcgggtttt actgatgcat atacagagat gctttttgtt    2820
cgcttggttg tgatgatgtg gtgtggttgg gcggtcgttc attcgttcta gatcggagta    2880
gaatactgtt tcaaactacc tggtgtattt attaattttg gaactgtatg tgtgtgtcat    2940
acatcttcat agttacgagt ttaagatgga tggaaatatc gatctaggat aggtatacat    3000
gttgatgtgg gttttactga tgcatataca tgatggcata tgcagcatct attcatatgc    3060
tctaaccttg agtacctatc tattataata aacaagtatg ttttataatt attttgatct    3120
tgatatactt ggatgatggc atatgcagca gctatatgtg gatttttta gccctgcctt    3180 catacgctat ttatttgctt ggtactgttt cttttgtcga tgctcaccct gttgtttggt    3240
gttacttctg caggtcgact ctagaggatc caccatgaac aagaacaaca ccaagctgag    3300
cacccgcgcc ctgccgagct tcatcgacta cttcaacggc atctacggct cgccaccgg    3360 catcaaggac atcatgaaca tgatcttcaa gaccgcacacc ggcggcgacc tgaccctgga    3420
cgagatcctg aagaaccagc agctgctgaa cgacatcagc ggcaagctgg acggcgtgaa    3480
cggcagcctg aacgacctga tcgcccaggg caacctgaac accgagctga caaggagat    3540 ccttaagatc gccaacgagc agaaccaggt gctgaacgac gtgaacaaca agctggacgc    3600
catcaacacc atgctgcgcg tgtacctgcc gaagatcacc agcatgctga gcgacgtgat    3660
gaagcagaac tacgccctga gcctgcagat cgagtacctg agcaagcagc tgcaggagat    3720
cagcgacaag ctggacatca tcaacgtgaa cgtcctgatc aacagcaccc tgaccgagat    3780 cacccccggcc taccagcgca tcaagtacgt gaacgagaag ttcgaagagc tgaccttcgc    3840
caccgagacc agcagcaagg tgaagaagga cggcagcccg gccgacatcc tggacgagct    3900
gaccgagctg accgagctgg cgaagagcgt gaccaagaac gacgtggacg gcttcgagtt    3960
ctacctgaac accttccacg acgtgatggt gggcaacaac ctgttcggcc gcagcgccct    4020
gaagaccgcc agcgagctga tcaccaagga gaacgtgaag accagcggca gcgaggtggg    4080
caacgtgtac aacttcctga tcgtgctgac cgccctgcag gcccaggcct tcctgaccct    4140
gaccacctgt cgcaagctgc tgggcctggc cgacatcgac tacaccagca tcatgaacga    4200
gcacttgaac aaggagaagg aggagttccg cgtgaacatc ctgccgaccc tgagcaacac    4260
cttcagcaac ccgaactacg ccaaggtgaa gggcagcgac gaggacgcca agatgatcgt    4320
ggaggctaag ccgggccacg cgttgatcgg cttcgagatc agcaacgaca gcatcaccgt    4380
gctgaaggtg tacgaggcca agctgaagca gaactaccag gtggacaagg acagcttgag    4440
```

```
cgaggtgatc tacggcgaca tggacaagct gctgtgtccg gaccagagcg agcaaatcta      4500
ctacaccaac aacatcgtgt tcccgaacga gtacgtgatc accaagatcg acttcaccaa      4560
gaagatgaag accctgcgct acgaggtgac cgccaacttc tacgacagca gcaccggcga      4620
gatcgacctg aacaagaaga aggtggagag cagcgaggcc gagtaccgca ccctgagcgc      4680
gaacgacgac ggcgtctaca tgccactggg cgtgatcagc gagaccttcc tgaccccgat      4740
caacggcttt ggcctgcagg ccgacgagaa cagccgcctg atcaccctga cctgtaagag      4800
ctacctgcgc gagctgctgc tagccaccga cctgagcaac aaggagacca agctgatcgt      4860
gccaccgagc ggcttcatca gcaacatcgt ggagaacggc agcatcgagg aggacaacct      4920
ggagccgtgg aaggccaaca acaagaacgc ctacgtggac cacaccggcg gcgtgaacgg      4980
caccaaggcc ctgtacgtgc acaaggacgg cggcatcagc cagttcatcg gcgacaagct      5040
gaagccgaag accgagtacg tgatccagta caccgtgaag ggcaagccat cgattcacct      5100
gaaggacgag aacaccggct acatccacta cgaggacacc aacaacaacc tggaggacta      5160
ccagaccatc aacaagcgct tcaccaccgg caccgacctg aagggcgtgt acctgatcct      5220
gaagagccag aacggcgacg aggcctgggg cgacaacttc atcatcctgg agatcagccc      5280
gagcgagaag ctgctgagcc cggagctgat caacaccaac aactggacca gcaccggcag      5340
caccaacatc agcggcaaca ccctgaccct gtaccagggc ggccgcggca tcctgaagca      5400
gaacctgcag ctggacagct tcagcaccta ccgcgtgtac ttcagcgtga gcggcgacgc      5460
caacgtgcgc atccgcaact cccgcgaggt gctgttcgag aagaggtaca tgagcggcgc      5520
caaggacgtg agcgagatgt tcaccaccaa gttcgagaag acaacttct acatcgagct      5580 gagccagggc aacaacctgt acggcggccc gatcgtgcac ttctacgacg tgagcatcaa      5640
gtaggagctc tagatctgtt ctgcacaaag tggagtagtc agtcatcgat caggaaccag      5700
acaccagact tttattcata cagtgaagtg aagtgaagtg cagtgcagtg agttgctggt      5760 tttttgtacaa cttagtatgt atttgtattt gtaaaatact tctatcaata aaatttctaa      5820
ttcctaaaac nnnnnnnnnn nnaaacattt ggcaataaag tttcttaaga ttgaatcctg      5880
ttgccggtct tgcgatgatt atcatataat ttctgttgaa ttcgttaag catgtaataa      5940 ttaacatgta atgcatgacg ttatttatga gatgggtttt tatgattaga gtcccgcaat      6000
tatacattta atacgcgata gaaaacaaaa tatagcgcgc aaactaggat aaattatcgc      6060
gcgcggtgtc atctatgtta ctagatcccc gggtctagac aattcagtac attaaaaacg      6120
tccgccatgg tctgaaggca acagataagg catactgggc cttgtggtag ttgtttact      6180 gggcctttt gtatgatcta taaaattcac tgggatcaac ccggagagga atggcagcag      6240
atgcagtccc cagggtcctc cgtcgccgcc tgagcacccg gcaccgcgc tgaaccggag      6300 agggacgcgc ggacgccgtg cagctggtgc ggagggggct gtggcagatg aggatgagac      6360
gcgtacgtgg ctgggaaggc cagcaggcca ccgggtcttc gtccagcccg gcgcgagtgg      6420
acaggactag agatggcaac ggttacaaac ccgctgggtt ttaccgtccc aaacccgtac      6480
ccgtgaaaaa tatctatgcc cattaaaaaa cccgtaccca tgacgggttt gagattttgc      6540
ccaaacccgt acccatcggg ttaacgggta cccatgggtt acccgcgggt tcatctccca      6600
atatacctgt tcttctcata atcaataagt atcgtaatga ttaatgatat catgatccaa      6660
aatctatgta atgaacaacg agttcatgat ttggtataaa aattattagt agagagaatg      6720
aaatacaaat aataagttgt ataattaagt gaccttgcac taagttatcc atccatcaca      6780
tatataacgc tagtaaaaac tataatatca agcaagcaac actctcaccg actactgata      6840
```

| | |
|---|---:|
| cattcaccaa ttgataaaaa atatgaagta aataaggaat aacaagtttg ttgttcgttt | 6900 |
| ataaaataaa atgacaatat gcactaggtt tggtcgggtt taaaaaaccc acgggttcac | 6960 |
| gggtttgggt actataggaa caaacccgta cccataaacc cattgggtac agatttatgc | 7020 |
| ccgttaacaa acccatgggt atgaaaattg acccaaacct atccctaat ggggtaaaaa | 7080 |
| cccatcgggt ttcggatttc gggtacccat tgccatctct agacaggaca acctcggccg | 7140 |
| gtcctgtatg taggccacca gcatcggcca gttggtacat ccagccgggg tcaggtcact | 7200 |
| tttactcgtc tcaatcagac aatcaccgtc caccaacgaa cgccaacgtt gtcacttgtc | 7260 |
| aggtcggttg agacttgtat ttttttttgt cctccgtaaa aatcggttca ccag | 7314 |

<210> SEQ ID NO 4
<211> LENGTH: 7239
<212> TYPE: DNA
<213> ORGANISM: Artificial
<220> FEATURE:
<223> OTHER INFORMATION: synthetic

<400> SEQUENCE: 4

| | |
|---|---:|
| tcctgtgttg ttggaacaga cttctgtctc ttctggtgat cataaatatt taaatgaacc | 60 |
| agttgtgttg gaaatgttg ttttcttttg tctctagact ggaaagcgga gttctcgtca | 120 |
| acacggttct ttcaactagg gatgaaagtg gtaatccgaa ttgttagtac aaatttaata | 180 |
| ttttaaaata gatatgtata aaattttatg ttgatctttt ttatgttatc aagcacatta | 240 |
| gtataaatta gtataaatat gaataaaata ttacataaaa tgtttatgt attatttggt | 300 |
| ccctacaaca taaatagttg aaaaaattac taaatttgtt ttcgaatcta tatcgaagtt | 360 |
| tatatctatt atttaagaaa aatataggat gaaaaggttt atcttttatg aatctttaca | 420 |
| agctggatct tataaacaag aaaataaatt tatattgtag attttatatc ctatttattc | 480 |
| gcaatcaaag aaaagcgact aaaaaactga ttaccgagta aatactgttt ccaaccgttt | 540 |
| tcgtccctac tatcaacgcc ttctcccaac cgcagtcgat ctgtccgtct gtatcaggcg | 600 |
| cagcggcacc cctgctgttc gactatctag accatagaat attttaggta tacaataatt | 660 |
| ttagttccac gctagaacat tttagttaga ataataacaa gatttgctat tgatgtagga | 720 |
| ctcgcccgtc actgtctaaa aaagcattct gtcggtctta ttctttaggc atcagcgggt | 780 |
| gtactatctc attttttccta tcatattcct cagtactctg ttaagtataa atggtctatt | 840 |
| ttacatgatg aactaataaa actaattaag gatcctaact ttttgtgaag gtaatttgga | 900 |
| tcattatgca ttaccatcct acgtatacct gctgcagcag catctgcgta agcacagcct | 960 |
| agatatatgc ttctgtgtgg actgaaagga gactttgttt atcaattagt atactcccat | 1020 |
| agtttaaact gaaggcggga aacgacaatc tgatcatgag cggagaatta agggagtcac | 1080 |
| gttatgaccc ccgccgatga cgcgggacaa gccgtttac gtttggaact gacagaaccg | 1140 |
| caacgttgaa ggagccactc agcaagctgg tacaagcttg catgcctgca gtgcagcgtg | 1200 |
| acccggtcgt gccctctct agagataatg agcattgcat gtctaagtta taaaaaatta | 1260 |
| ccacatattt ttttgtcac acttgttga agtgcagttt atctatcttt atacatatat | 1320 |
| ttaaacttta ctctacgaat aatataatct atagtactac aataatatca gtgttttaga | 1380 |
| gaatcatata aatgaacagt tagacatggt ctaaaggaca attgagtatt ttgacaacag | 1440 |
| gactctacag ttttatcttt ttagtgtgca tgtgttctcc ttttttttg caaatagctt | 1500 |
| cacctatata atacttcatc cattttatta gtacatccat ttagggttta gggttaatgg | 1560 |

```
tttttataga ctaattttt tagtacatct attttattct attttagcct ctaaattaag    1620
aaaactaaaa ctctatttta gttttttat ttaataattt agatataaaa tagaataaaa    1680
taaagtgact aaaaattaaa caaatacct ttaagaaatt aaaaaaacta aggaaacatt    1740
tttcttgttt cgagtagata atgccagcct gttaaacgcc gtcgacgagt ctaacggaca    1800
ccaaccagcg aaccagcagc gtcgcgtcgg gccaagcgaa gcagacggca cggcatctct    1860
gtcgctgcct ctggacccct ctcgagagtt ccgctccacc gttggacttg ctccgctgtc    1920
ggcatccaga aattgcgtgg cggagcggca gacgtgagcc ggcacggcag gcggcctcct    1980
cctcctctca cggcaccggc agctacgggg gattcctttc ccaccgctcc ttcgctttcc    2040
cttcctcgcc cgccgtaata aatagacacc ccctccacac cctctttccc caacctcgtg    2100
ttgttcggag cgcacacaca cacaaccaga tctcccccaa atccacccgt cggcacctcc    2160
gcttcaaggt acgccgctcg tcctccccc ccccccctct ctaccttctc tagatcggcg    2220
ttccggtcca tggttagggc ccggtagttc tacttctgtt catgtttgtg ttagatccgt    2280
gtttgtgtta gatccgtgct gctagcgttc gtacacggat gcgacctgta cgtcagacac    2340
gttctgattg ctaacttgcc agtgtttctc tttggggaat cctgggatgg ctctagccgt    2400
tccgcagacg ggatcgattt catgattttt tttgtttcgt tgcataggt ttggtttgcc    2460 cttttccttt atttcaatat atgccgtgca cttgtttgtc gggtcatctt ttcatgcttt    2520
tttttgtctt ggttgtgatg atgtggtctg gttgggcggt cgttctagat cggagtagaa    2580
ttctgtttca aactacctgg tggatttatt aattttggat ctgtatgtgt gtgccataca    2640
tattcatagt tacgaattga agatgatgga tggaaatatc gatctaggat aggtatacat    2700
gttgatgcgg gttttactga tgcatataca gagatgcttt ttgttcgctt ggttgtgatg    2760
atgtggtgtg gttgggcggt cgttcattcg ttctagatcg gagtagaata ctgtttcaaa    2820
ctacctggtg tatttattaa ttttggaact gtatgtgtgt gtcatacatc ttcatagtta    2880
cgagtttaag atggatggaa atatcgatct aggataggta tacatgttga tgtgggtttt    2940
actgatgcat atacatgatg gcatatgcag catctattca tatgctctaa ccttgagtac    3000
ctatctatta taataaacaa gtatgttta taattattt gatcttgata tacttggatg    3060
atggcatatg cagcagctat atgtggatt ttttagcct gccttcatac gctatttatt    3120
tgcttggtac tgtttctttt gtcgatgctc accctgttgt ttggtgttac ttctgcaggt    3180
cgactctaga ggatccacca tgaacaagaa caacaccaag ctgagcaccc gcgccctgcc    3240
gagcttcatc gactacttca cggcatcta cggcttcgcc accggcatca aggacatcat    3300
gaacatgatc ttcaagaccg acaccggcgg cgacctgacc ctggacgaga tcctgaagaa    3360
ccagcagctg ctgaacgaca tcagcggcaa gctggacggc gtgaacgca gcctgaacga    3420 cctgatcgcc cagggcaacc tgaacaccga gctgagcaag gagatcctta agatcgccaa    3480
cgagcagaac caggtgctga cgacgtgaa caacaagctg gacgccatca acaccatgct    3540
gcgcgtgtac ctgccgaaga tcaccagcat gctgagcgac gtgatgaagc agaactacgc    3600
cctgagcctg cagatcgagt acctgagcaa gcagctgcag gagatcagcg acaagctgga    3660
catcatcaac gtgaacgtcc tgatcaacag caccctgacc gagatcaccc cggcctacca    3720
gcgcatcaag tacgtgaacg agaagttcga agagctgacc ttcgccaccg agaccagcag    3780
caaggtgaag aaggacggca gcccggccga catcctggac gagctgaccg agctgaccga    3840
gctggcgaag agcgtgacca agaacagcgt ggacggcttc gagttctacc tgaacaccctt    3900 ccacgacgtg atggtgggca acaacctgtt cggccgcagc gccctgaaga ccgccagcga    3960
```

```
gctgatcacc aaggagaacg tgaagaccag cggcagcgag gtgggcaacg tgtacaactt    4020
cctgatcgtg ctgaccgccc tgcaggccca ggccttcctg accctgacca cctgtcgcaa    4080
gctgctgggc ctggccgaca tcgactacac cagcatcatg aacgagcact gaacaagga    4140
gaaggaggag ttccgcgtga acatcctgcc gaccctgagc aacaccttca gcaacccgaa    4200
ctacgccaag gtgaagggca gcgacgagga cgccaagatg atcgtggagg ctaagccggg    4260
ccacgcgttg atcggcttcg agatcagcaa cgacagcatc accgtgctga aggtgtacga    4320
ggccaagctg aagcagaact accaggtgga caaggacagc ttgagcgagg tgatctacgg    4380
cgacatggac aagctgctgt gtccggacca gagcgagcaa atctactaca ccaacaacat    4440
cgtgttcccg aacgagtacg tgatcaccaa gatcgacttc accaagaaga tgaagaccct    4500
gcgctacgag gtgaccgcca acttctacga cagcagcacc ggcgagatcg acctgaacaa    4560
gaagaaggtg gagagcagcg aggccgagta ccgcaccctg agcgcgaacg acgacggcgt    4620
ctacatgcca ctgggcgtga tcagcgagac cttcctgacc ccgatcaacg gctttggcct    4680
gcaggccgac gagaacagcc gcctgatcac cctgacctgt aagagctacc tgcgcgagct    4740
gctgctagcc accgacctga gcaacaagga gaccaagctg atcgtgccac cgagcggctt    4800
catcagcaac atcgtggaga acggcagcat cgaggaggac aacctggagc cgtggaaggc    4860
caacaacaag aacgcctacg tggaccacac cggcggcgtg aacggcacca aggccctgta    4920
cgtgcacaag gacggcggca tcagccagtt catcggcgac aagctgaagc cgaagaccga    4980
gtacgtgatc cagtacaccg tgaagggcaa gccatcgatt cacctgaagg acgagaacac    5040
cggctacatc cactacgagg acaccaacaa caacctggag gactaccaga ccatcaacaa    5100
gcgcttcacc accggcaccg acctgaaggg cgtgtacctg atcctgaaga gccagaacgg    5160
cgacgaggcc tggggcgaca acttcatcat cctggagatc agcccgagcg agaagctgct    5220
gagcccggag ctgatcaaca ccaacaactg gaccagcacc ggcagcacca acatcagcgg    5280
caacaccctg accctgtacc agggcggccg cggcatcctg aagcagaacc tgcagctgga    5340
cagcttcagc acctaccgcg tgtacttcag cgtgagcggc gacgccaacg tgcgcatccg    5400
caactcccgc gaggtgctgt tcgagaagag gtacatgagc ggcgccaagg acgtgagcga    5460
gatgttcacc accaagttcg agaaggacaa cttctacatc gagctgagcc agggcaacaa    5520
cctgtacggc ggcccgatcg tgcacttcta cgacgtgagc atcaagtagg agctctagat    5580
ctgttctgca caaagtggag tagtcagtca tcgatcagga accagacacc agactttat    5640
tcatacagtg aagtgaagtg aagtgcagtg cagtgagttg ctggttttg tacaacttag    5700
tatgtatttg tatttgtaaa atacttctat caataaaatt tctaattcct aaaaccaaaa    5760
ttcgttcaaa catttggcaa taaagtttct taagattgaa tcctgttgcc ggtcttgcga    5820
tgattatcat ataatttctg ttgaattacg ttaagcatgt aataattaac atgtaatgca    5880
tgacgttatt tatgagatgg gtttttatga ttagagtccc gcaattatac atttaatacg    5940
cgatagaaaa caaaatatag cgcgcaaact aggataaatt atcgcgcgcg gtgtcatcta    6000
tgttactaga tccccgggtc tagacaattc agtacattaa aaacgtccgc catggtctga    6060
aggcaacaga taaggcatac tgggccttgt ggtagttgtt ttactgggcc ttttgtatg    6120
atctataaaa ttcactggga tcaacccgga gaggaatggc agcagatgca gtccccaggg    6180
tcctccgtcg ccgcctgagc acccggcacc cgcgctgaac cggagaggga cgcgcggacg    6240
ccgtgcagct ggtgcggagg gggctgtggc agatgaggat gagacgcgta cgtggctggg    6300
```

| | |
|---|---|
| aaggccagca ggccaccggg tcttcgtcca gcccggcgcg agtggacagg actagagatg | 6360 |
| gcaacggtta caaacccgct gggttttacc gtcccaaacc cgtacccgtg aaaaatatct | 6420 |
| atgcccatta aaaacccgt acccatgacg ggtttgagat tttgcccaaa cccgtaccca | 6480 |
| tcgggttaac gggtacccat gggttacccg cgggtttcat ctccaatata cctgttcttc | 6540 |
| tcataatcaa taagtatcgt aatgattaat gatatcatga tccaaaatct atgtaatgaa | 6600 |
| caacgagttc atgatttggt ataaaaatta ttagtagaga gaatgaaata caaataataa | 6660 |
| gttgtataat taagtgacct tgcactaagt tatccatcca tcacatatat aacgctagta | 6720 |
| aaaactataa tatcaagcaa gcaacactct caccgactac tgatacattc accaattgat | 6780 |
| aaaaaatatg aagtaaataa ggaataacaa gtttgttgtt cgtttataaa ataaaatgac | 6840 |
| aatatgcact aggtttggtc gggttttaaaa aacccacggg ttcacgggtt tgggtactat | 6900 |
| aggaacaaac ccgtacccat aaacccattg ggtacagatt tatgcccgtt aacaaaccca | 6960 |
| tgggtatgaa aattgaccca aacctatacc ctaatgggggt aaaaacccat cgggtttcgg | 7020 |
| atttcgggta cccattgcca tctctagaca ggacaacctc ggccggtcct gtatgtaggc | 7080 |
| caccagcatc ggccagttgg tacatccagc cggggtcagg tcacttttac tcgtctcaat | 7140 |
| cagacaatca ccgtccacca acgaacgcca acgttgtcac ttgtcaggtc ggttgagact | 7200 |
| tgtattttt tttgtcctcc gtaaaaatcg gttcaccag | 7239 |

<210> SEQ ID NO 5
<211> LENGTH: 7235
<212> TYPE: DNA
<213> ORGANISM: Artificial
<220> FEATURE:
<223> OTHER INFORMATION: synthetic

<400> SEQUENCE: 5

| | |
|---|---|
| tcctgtgttg ttggaacaga cttctgtctc ttctggtgat cataaatatt taaatgaacc | 60 |
| agttgtgttg gaaaatgttg ttttcttttg tctctagact ggaaagcgga gttctcgtca | 120 |
| acacggttct ttcaactagg gatgaaagtg gtaatccgaa ttgttagtac aaatttaata | 180 |
| ttttaaaata gatatgtata aaattttatg ttgatctttt ttatgttatc aagcacatta | 240 |
| gtataaatta gtataaatat gaataaaata ttacataaaa tgttttatgt attatttggt | 300 |
| ccctacaaca taaatagttg aaaaaattac taaatttgtt ttcgaatcta tatcgaagtt | 360 |
| tatatctatt atttaagaaa aatataggat gaaaaggttt atcttttatg aatctttaca | 420 |
| agctggatct tataaacaag aaaataaatt tatattgtag attttatatc ctatttattc | 480 |
| gcaatcaaag aaaagcgact aaaaaactga ttaccgagta aatactgttt ccaaccgttt | 540 |
| tcgtccctac tatcaacgcc ttctcccaac cgcagtcgat ctgtccgtct gtatcaggcg | 600 |
| cagcggcacc cctgctgttc gactatctag accatagaat attttaggta tacaataatt | 660 |
| ttagttccac gctagaacat tttagttaga ataataacaa gatttgctat tgatgtagga | 720 |
| ctcgcccgtc actgtctaaa aaagcattct gtcggtctta ttcttaggc atcagcgggt | 780 |
| gtactatctc attttccta tcatattcct cagtactctg ttaagtataa atggtctatt | 840 |
| ttacatgatg aactaataaa actaattaag gatcctaact ttttgtgaag gtaatttgga | 900 |
| tcattatgca ttaccatcct acgtatacct gctgcagcag catctgcgta agcacagcct | 960 |
| agatatatgc ttctgtgtgg actgaaagga gactttgttt atcaattagt atactcccat | 1020 |
| taaactgaag gcgggaaacg acaatctgat catgagcgga gaattaaggg agtcacgtta | 1080 |
| tgaccccgc cgatgacgcg ggacaagccg ttttacgttt ggaactgaca gaaccgcaac | 1140 |

```
gttgaaggag ccactcagca agctggtaca agcttgcatg cctgcagtgc agcgtgaccc    1200
ggtcgtgccc ctctctagag ataatgagca ttgcatgtct aagttataaa aaattaccac    1260
atattttttt tgtcacactt gtttgaagtg cagtttatct atctttatac atatatttaa    1320 acttactct acgaataata taatctatag tactacaata atatcagtgt tttagagaat     1380
catataaatg aacagttaga catggtctaa aggacaattg agtattttga caacaggact    1440
ctacagtttt atcttttttag tgtgcatgtg ttctcctttt tttttgcaaa tagcttcacc   1500
tatataatac ttcatccatt ttattagtac atccatttag ggtttagggt taatggtttt    1560
tatagactaa ttttttttagt acatctattt tattctattt tagcctctaa attaagaaaa   1620
ctaaaactct attttagttt ttttatttaa taatttagat ataaaataga ataaaataaa    1680
gtgactaaaa attaaacaaa tacccttttaa gaaattaaaa aaactaagga aacattttc    1740 ttgtttcgag tagataatgc cagcctgtta aacgccgtcg acgagtctaa cggacaccaa    1800
ccagcgaacc agcagcgtcg cgtcgggcca agcgaagcag acggcacggc atctctgtcg    1860
ctgcctctgg acccctctcg agagttccgc tccaccgttg acttgctcc gctgtcggca    1920 tccagaaatt gcgtggcgga gcggcagacg tgagccggca cggcaggcgg cctcctcctc    1980
ctctcacggc accggcagct acgggggatt ccttccccac cgctccttcg ctttcccttc    2040
ctcgcccgcc gtaataaata dacaccccct ccacaccctc tttccccaac ctcgtgttgt    2100
tcggagcgca cacacacaca accagatctc ccccaaatcc acccgtcggc acctccgctt    2160
caaggtacgc cgctcgtcct cccccccccc ccctctctac cttctctaga tcggcgttcc    2220
ggtccatggt tagggcccgg tagttctact tctgttcatg tttgtgttag atccgtgttt    2280
gtgttagatc cgtgctgcta gcgttcgtac acggatgcga cctgtacgtc agacacgttc    2340
tgattgctaa cttgccagtg tttctctttg gggaatcctg ggatggctct agccgttccg    2400
cagacgggat cgatttcatg atttttttg tttcgttgca tagggtttgg tttgccctt     2460 tcctttattt caatatatgc cgtgcacttg tttgtcgggt catcttttca tgcttttttt    2520
tgtcttggtt gtgatgatgt ggtctggttg ggcggtcgtt ctagatcgga gtagaattct    2580
gtttcaaact acctggtgga tttattaatt ttggatctgt atgtgtgtgc catacatatt    2640
catagttacg aattgaagat gatggatgga aatatcgatc taggataggt atacatgttg    2700
atgcgggttt tactgatgca tatacagaga tgctttttgt tcgcttggtt gtgatgatgt    2760
ggtgtggttg ggcggtcgtt cattcgttct agatcggagt agaatactgt ttcaaactac    2820
ctggtgtatt tattaatttt ggaactgtat gtgtgtgtca tacatcttca tagttacgag    2880
tttaagatgg atggaaatat cgatctagga taggtataca tgttgatgtg ggttttactg    2940
atgcatatac atgatggcat atgcagcatc tattcatatg ctctaacctt gagtacctat    3000
ctattataat aaacaagtat gttttataat tattttgatc ttgatatact tggatgatgg    3060
catatgcagc agctatatgt ggatttttt agccctgcct tcatacgcta tttatttgct    3120
tggtactgtt tcttttgtcg atgctcaccc tgttgtttgg tgttacttct gcaggtcgac    3180
tctagaggat ccaccatgaa caagaacaac accaagctga gcacccgcgc cctgccgagc    3240
ttcatcgact acttcaacgg catctacggc ttcgccaccg gcatcaagga catcatgaac    3300
atgatcttca agaccgacac cggcggcgac ctgaccctgg acgagatcct gaagaaccag    3360
cagctgctga cgacatcag cggcaagctg acggcgtga acggcagcct gaacgacctg    3420
atcgcccagg gcaacctgaa caccgagctg agcaaggaga tccttaagat cgccaacgag    3480
```

```
cagaaccagg tgctgaacga cgtgaacaac aagctggacg ccatcaacac catgctgcgc    3540
gtgtacctgc cgaagatcac cagcatgctg agcgacgtga tgaagcagaa ctacgccctg    3600
agcctgcaga tcgagtacct gagcaagcag ctgcaggaga tcagcgacaa gctggacatc    3660
atcaacgtga acgtcctgat caacagcacc ctgaccgaga tcaccccggc ctaccagcgc    3720
atcaagtacg tgaacgagaa gttcgaagag ctgaccttcg ccaccgagac cagcagcaag    3780
gtgaagaagg acggcagccc ggccgacatc ctggacgagc tgaccgagct gaccgagctg    3840
gcgaagagcg tgaccaagaa cgacgtggac ggcttcgagt tctacctgaa caccttccac    3900
gacgtgatgg tgggcaacaa cctgttcggc cgcagcgccc tgaagaccgc cagcgagctg    3960
atcaccaagg agaacgtgaa gaccagcggc agcgaggtgg gcaacgtgta caacttcctg    4020
atcgtgctga ccgccctgca ggcccaggcc ttcctgaccc tgaccaccctg tcgcaagctg    4080 ctgggcctgg ccgacatcga ctacaccagc atcatgaacg agcacttgaa caaggagaag    4140
gaggagttcc gcgtgaacat cctgccgacc ctgagcaaca ccttcagcaa cccgaactac    4200
gccaaggtga agggcagcga cgaggacgcc aagatgatcg tggagctaa gccgggccac    4260 gcgttgatcg gcttcgagat cagcaacgac agcatcaccg tgctgaaggt gtacgaggcc    4320
aagctgaagc agaactacca ggtggacaag acagcttga gcgaggtgat ctacggcgac    4380
atggacaagc tgctgtgtcc ggaccagagc gagcaaatct actacaccaa caacatcgtg    4440
ttcccgaacg agtacgtgat caccaagatc gacttcacca gaagatgaa gaccctgcgc    4500 tacgaggtga ccgccaactt ctacgacagc agcaccggcg agatcgacct gaacaagaag    4560
aaggtggaga gcagcgaggc cgagtaccgc accctgagcg cgaacgacga cggcgtctac    4620
atgccactgg gcgtgatcag cgagaccttc ctgaccccga tcaacggctt tggcctgcag    4680
gccgacgaga acagccgcct gatcaccctg acctgtaaga gctacctgcg cgagctgctg    4740
ctagccaccg acctgagcaa caaggagacc aagctgatcg tgccaccgag cggcttcatc    4800
agcaacatcg tggagaacgg cagcatcgag gaggacaacc tggagccgtg gaaggccaac    4860
aacaagaacg cctacgtgga ccacaccggc ggcgtgaacg gcaccaaggc cctgtacgtg    4920
cacaaggacg gcggcatcag ccagttcatc ggcgacaagc tgaagccgaa gaccgagtac    4980
gtgatccagt acaccgtgaa gggcaagcca tcgattcacc tgaaggacga gaacaccggc    5040
tacatccact acgaggacac caacaacaac ctggaggact accagaccat caacaagcgc    5100
ttcaccaccg gcaccgacct gaagggcgtg tacctgatcc tgaagagcca gaacggcgac    5160
gaggcctggg gcgacaactt catcatcctg gagatcagcc cgagcgagaa gctgctgagc    5220
ccggagctga tcaacaccaa caactggacc agcaccggca gcaccaacat cagcggcaac    5280
accctgaccc tgtaccaggg cggccgcggc atcctgaagc agaacctgca gctggacagc    5340
ttcagcacct accgcgtgta cttcagcgtg agcggcgacg ccaacgtgcg catccgcaac    5400
tcccgcgagg tgctgttcga gaagaggtac atgagcggcg ccaaggacgt gagcgagatg    5460
ttcaccacca agttcgagaa ggacaacttc tacatcgagc tgagccaggg caacaacctg    5520
tacggcggcc cgatcgtgca cttctacgac gtgagcatca gtaggagct ctagatctgt    5580 tctgcacaaa gtggagtagt cagtcatcga tcaggaacca gacaccagac ttttattcat    5640
acagtgaagt gaagtgaagt gcagtgcagt gagttgctgg ttttttgtaca acttagtatg    5700 tatttgtatt tgtaaaatac ttctatcaat aaaatttcta attcctaaaa ccaaaattcg    5760
ttcaaacatt tggcaataaa gtttcttaag attgaatcct gttgccggtc ttgcgatgat    5820
tatcatataa tttctgttga attacgttaa gcatgtaata attaacatgt aatgcatgac    5880
```

```
gttatttatg agatgggttt ttatgattag agtcccgcaa ttatacattt aatacgcgat    5940
agaaaacaaa atatagcgcg caaactagga taaattatcg cgcgcggtgt catctatgtt    6000
actagatccc cgggtctaga caattcagta cattaaaaac gtccgccatg gtctgaaggc    6060
aacagataag gcatactggg ccttgtggta gttgttttac tgggcctttt tgtatgatct    6120
ataaaattca ctgggatcaa cccggagagg aatggcagca gatgcagtcc ccagggtcct    6180
ccgtcgccgc ctgagcaccc ggcacccgcg ctgaaccgga gagggacgcg cggacgccgt    6240
gcagctggtg cggaggggc tgtggcagat gaggatgaga cgcgtacgtg gctgggaagg    6300
ccagcaggcc accgggtctt cgtccagccc ggcgcgagtg gacaggacta gagatggcaa    6360
cggttacaaa cccgctgggt tttaccgtcc caaacccgta cccgtgaaaa atatctatgc    6420
ccattaaaaa acccgtaccc atgacgggtt tgagattttg cccaaacccg tacccatcgg    6480
gttaacgggt acccatgggt tacccgcggg tttcatctcc aatatacctg ttcttctcat    6540
aatcaataag tatcgtaatg attaatgata tcatgatcca aaatctatgt aatgaacaac    6600
gagttcatga tttggtataa aaattattag tagagagaat gaaatacaaa taataagttg    6660
tataattaag tgaccttgca ctaagttatc catccatcac atatataacg ctagtaaaaa    6720
ctataatatc aagcaagcaa cactctcacc gactactgat acattcacca attgataaaa    6780
aatatgaagt aaataaggaa taacaagttt gttgttcgtt tataaaataa aatgacaata    6840
tgcactaggt ttggtcgggt ttaaaaaacc cacgggttca cgggtttggg tactatagga    6900
acaaacccgt acccataaac ccattgggta cagatttatg cccgttaaca aacccatggg    6960
tatgaaaatt gacccaaacc tatacccctaa tggggtaaaa acccatcggg tttcggattt    7020
cgggtaccca ttgccatctc tagacaggac aacctcggcc ggtcctgtat gtaggccacc    7080
agcatcggcc agttggtaca tccagccggg gtcaggtcac ttttactcgt ctcaatcaga    7140
caatcaccgt ccaccaacga acgccaacgt tgtcacttgt caggtcggtt gagacttgta    7200 ttttttttg tcctccgtaa aaatcggttc accag                                7235

<210> SEQ ID NO 6
<211> LENGTH: 7310
<212> TYPE: DNA
<213> ORGANISM: Artificial
<220> FEATURE:
<223> OTHER INFORMATION: synthetic

<400> SEQUENCE: 6
tcctgtgttg ttggaacaga cttctgtctc ttctggtgat cataaatatt taaatgaacc      60
agttgtgttg gaaatgttg ttttcttttg tctctagact ggaaagcgga gttctcgtca     120
acacggttct ttcaactagg gatgaaagtg gtaatccgaa ttgttagtac aaatttaata     180
ttttaaaata gatatgtata aaattttatg ttgatctttt ttatgttatc aagcacatta     240
gtataaatta gtaaaatat gaataaaata ttacataaaa tgtttatgt attatttggt      300 ccctacaaca taaatagttg aaaaaattac taaatttgtt ttcgaatcta tatcgaagtt     360
tatatctatt atttaagaaa aatataggat gaaaaggttt atcttttatg aatctttaca     420
agctggatct tataaacaag aaaataaatt tatattgtag attttatatc ctatttattc     480
gcaatcaaag aaaagcgact aaaaaactga ttaccgagta aatactgttt ccaaccgttt     540
tcgtccctac tatcaacgcc ttctcccaac cgcagtcgat ctgtccgtct gtatcaggcg     600
cagcggcacc cctgctgttc gactatctag accatagaat attttaggta tacaataatt     660
```

```
ttagttccac gctagaacat tttagttaga ataataacaa gatttgctat tgatgtagga    720
ctcgcccgtc actgtctaaa aaagcattct gtcggtctta ttctttaggc atcagcgggt    780
gtactatctc attttcccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccaa   1020
aaaactgatg acaccaatga tgcaaatagg ctgggaatag tctgtctaat agtttgagtg   1080
aatcatgtca tagtttaaac tgaaggcggg aaacgacaat ctgatcatga gcggagaatt   1140
aagggagtca cgttatgacc cccgccgatg acgcgggaca agccgtttta cgtttggaac   1200
tgacagaacc gcaacgttga aggagccact cagcaagctg gtacaagctt gcatgcctgc   1260
agtgcagcgt gacccggtcg tgcccctctc tagagataat gagcattgca tgtctaagtt   1320
ataaaaaatt accacatatt tttttgtca cacttgtttg aagtgcagtt tatctatctt   1380
tatacatata tttaaacttt actctacgaa taatataatc tatagtacta caataatatc   1440
agtgttttag agaatcatat aaatgaacag ttagacatgg tctaaaggac aattgagtat   1500
tttgacaaca ggactctaca gttttatctt tttagtgtgc atgtgttctc ctttttttt    1560 gcaaatagct tcacctatat aatacttcat ccattttatt agtacatcca tttagggttt   1620
agggttaatg gttttttatag actaattttt ttagtacatc tattttattc tattttagcc   1680
tctaaattaa gaaaactaaa actctatttt agttttttta tttaataatt tagatataaa   1740
atagaataaa ataagtgac taaaaattaa acaaatacc tttaagaaat taaaaaaact    1800
aaggaaacat ttttcttgtt tcgagtagat aatgccagcc tgttaaacgc cgtcgacgag   1860
tctaacggac accaaccagc gaaccagcag cgtcgcgtcg ggccaagcga agcagacggc   1920
acggcatctc tgtcgctgcc tctggacccc tctcgagagt tccgctccac cgttggactt   1980
gctccgctgt cggcatccag aaattgcgtg gcggagcggc agacgtgagc cggcacggca   2040
ggcggcctcc tcctcctctc acggcaccgg cagctacggg ggattccttt cccaccgctc   2100
cttcgctttc ccttcctcgc ccgccgtaat aaatagacac cccctccaca ccctcttcc    2160 ccaacctcgt gttgttcgga gcgcacacac acacaaccag atctccccca aatccacccg   2220
tcggcacctc cgcttcaagg tacgccgctc gtcctccccc ccccccctc tctaccttct    2280 ctagatcggc gttccggtcc atggttaggg cccggtagtt ctacttctgt tcatgtttgt   2340
gttagatccg tgtttgtgtt agatccgtgc tgctagcgtt cgtacacgga tgcgacctgt   2400
acgtcagaca cgttctgatt gctaacttgc cagtgtttct ctttggggaa tcctgggatg   2460
gctctagccg ttccgcagac gggatcgatt tcatgatttt ttttgtttcg ttgcataggg   2520
tttggtttgc ccttttcctt tatttcaata tatgccgtgc acttgtttgt cgggtcatct   2580
tttcatgctt ttttttgtct tggttgtgat gatgtggtct ggttgggcgg tcgttctaga   2640
tcggagtaga attctgtttc aaactacctg gtggatttat taattttgga tctgtatgtg   2700
tgtgccatac atattcatag ttacgaattg aagatgatgg atggaaatat cgatctagga   2760
taggtataca tgttgatgcg ggttttactg atgcatatac agagatgctt tttgttcgct   2820
tggttgtgat gatgtggtgt ggttgggcgg tcgttcattc gttctagatc ggagtagaat   2880
actgtttcaa actacctggt gtatttatta attttggaac tgtatgtgtg tgtcatacat   2940
cttcatagtt acgagtttaa gatggatgga aatatcgatc taggataggt atacatgttg   3000
atgtgggttt tactgatgca tatacatgat ggcatatgca gcatctattc atatgctcta   3060
```

```
accttgagta cctatctatt ataataaaca agtatgtttt ataattattt tgatcttgat   3120
atacttggat gatggcatat gcagcagcta tatgtggatt tttttagccc tgccttcata   3180
cgctatttat ttgcttggta ctgtttcttt tgtcgatgct caccctgttg tttggtgtta   3240
cttctgcagg tcgactctag aggatccacc atgaacaaga acaacaccaa gctgagcacc   3300
cgcgccctgc cgagcttcat cgactacttc aacggcatct acggcttcgc caccggcatc   3360
aaggacatca tgaacatgat cttcaagacc gacaccggcg cgacctgac cctggacgag    3420
atcctgaaga accagcagct gctgaacgac atcagcggca agctggacgg cgtgaacggc   3480
agcctgaacg acctgatcgc ccagggcaac ctgaacaccg agctgagcaa ggagatcctt   3540
aagatcgcca acgagcagaa ccaggtgctg aacgacgtga acaacaagct ggacgccatc   3600
aacaccatgc tgcgcgtgta cctgccgaag atcaccagca tgctgagcga cgtgatgaag   3660
cagaactacg ccctgagcct gcagatcgag tacctgagca gcagctgca ggagatcagc    3720
gacaagctgg acatcatcaa cgtgaacgtc ctgatcaaca gcaccctgac cgagatcacc   3780
ccggcctacc agcgcatcaa gtacgtgaac gagaagttcg aagagctgac cttcgccacc   3840
gagaccagca gcaaggtgaa gaaggacggc agcccggccg acatcctgga cgagctgacc   3900
gagctgaccg agctggcgaa gagcgtgacc aagaacgacg tggacggctt cgagttctac   3960
ctgaacacct tccacgacgt gatggtgggc aacaacctgt tcggccgcag cgccctgaag   4020
accgccagcg agctgatcac caaggagaac gtgaagacca gcgcagcga ggtgggcaac    4080
gtgtacaact tcctgatcgt gctgaccgcc ctgcaggccc aggccttcct gaccctgacc   4140
acctgtcgca agctgctggg cctggccgac atcgactaca ccagcatcat gaacgagcac   4200
ttgaacaagg agaaggagga gttccgcgtg aacatcctgc cgaccctgag caacaccttc   4260
agcaacccga actacgccaa ggtgaagggc agcgacgagg acgccaagat gatcgtggag   4320
gctaagccgg ccacgcgtt gatcggcttc gagatcagca cgacagcat caccgtgctg     4380
aaggtgtacg aggccaagct gaagcagaac taccaggtgg acaaggacag cttgagcgag   4440
gtgatctacg cgacatgga caagctgctg tgtccggacc agagcgagca aatctactac    4500
accaacaaca tcgtgttccc gaacgagtac gtgatcacca gatcgactt caccaagaag    4560
atgaagaccc tgcgctacga ggtgaccgcc aacttctacg acagcagcac cggcgagatc   4620
gacctgaaca agaagaaggt ggagagcagc gaggccgagt accgcaccct gagcgcgaac   4680
gacgacggcg tctacatgcc actgggcgtg atcagcgaga ccttcctgac cccgatcaac   4740
ggctttggcc tgcaggccga cgagaacagc cgcctgatca ccctgacctg taagagctac   4800
ctgcgcgagc tgctgctagc caccgacctg agcaacaagg agaccaagct gatcgtgcca   4860
ccgagcggct tcatcagcaa catcgtggag aacggcagca tcgaggagga caacctggag   4920
ccgtggaagg ccaacaacaa gaacgcctac gtggaccaca ccggcggcgt gaacggcacc   4980
aaggccctgt acgtgcacaa ggacggcggc atcagccagt tcatcggcga caagctgaag   5040
ccgaagaccg agtacgtgat ccagtacacc gtgaagggca agccatcgat tcacctgaag   5100
gacgagaaca ccggctacat ccactacgag gacaccaaca caacctgga ggactaccag    5160
accatcaaca agcgcttcac caccggcacc gacctgaagg gcgtgtacct gatcctgaag   5220
agccagaacg gcgacgaggc ctggggcgac aacttcatca tcctggagat cagcccgagc   5280
gagaagctgc tgagcccgga gctgatcaac accaacaact ggaccagcac cggcagcacc   5340
aacatcagcg gcaacaccct gaccctgtac cagggcggcc gcggcatcct gaagcagaac   5400
```

```
ctgcagctgg acagcttcag cacctaccgc gtgtacttca gcgtgagcgg cgacgccaac    5460
gtgcgcatcc gcaactcccg cgaggtgctg ttcgagaaga ggtacatgag cggcgccaag    5520
gacgtgagcg agatgttcac caccaagttc gagaaggaca acttctacat cgagctgagc    5580
cagggcaaca acctgtacgg cggcccgatc gtgcacttct acgacgtgag catcaagtag    5640
gagctctaga tctgttctgc acaaagtgga gtagtcagtc atcgatcagg aaccagacac    5700 cagacttta ttcatacagt gaagtgaagt gaagtgcagt gcagtgagtt gctggttttt    5760
gtacaactta gtatgtattt gtatttgtaa atacttcta tcaataaaat ttctaattcc     5820
taaaaccaaa attcgttcaa acatttggca ataaagtttc ttaagattga atcctgttgc    5880
cggtcttgcg atgattatca tataatttct gttgaattac gttaagcatg taataattaa    5940
catgtaatgc atgacgttat ttatgagatg ggttttatg attagagtcc cgcaattata     6000
catttaatac gcgatagaaa acaaaatata gcgcgcaaac taggataaat tatcgcgcgc    6060
ggtgtcatct atgttactag atccccgggt ctagacaatt cagtacatta aaaacgtccg    6120
ccatggtctg aaggcaacag ataaggcata ctgggccttg tggtagttgt tttactgggc    6180 cttttttgtat gatctataaa attcactggg atcaacccgg agaggaatgg cagcagatgc    6240
agtccccagg gtcctccgtc gccgcctgag cacccggcac ccgcgctgaa ccggagaggg    6300
acgcgcggac gccgtgcagc tggtgcggag ggggctgtgg cagatgagga tgagacgcgt    6360
acgtggctgg gaaggccagc aggccaccgg gtcttcgtcc agcccggcgc gagtggacag    6420
gactagagat ggcaacggtt acaaacccgc tgggttttac cgtcccaaac ccgtacccgt    6480 gaaaatatc tatgcccatt aaaaaacccg tacccatgac gggtttgaga ttttgcccaa    6540
acccgtaccc atcgggttaa cgggtaccca tgggttaccc gcgggtttca tctccaatat    6600
acctgttctt ctcataatca ataagtatcg taatgattaa tgatatcatg atccaaaatc    6660
tatgtaatga acaacgagtt catgatttgg tataaaaatt attagtagag agaatgaaat    6720
acaaataata agttgtataa ttaagtgacc ttgcactaag ttatccatcc atcacatata    6780
taacgctagt aaaaactata atatcaagca agcaacactc tcaccgacta ctgatacatt    6840
caccaattga taaaaaatat gaagtaaata aggaataaca agtttgttgt tcgtttataa    6900
aataaaatga caatatgcac taggtttggt cgggtttaaa aaacccacgg gttcacgggt    6960
ttgggtacta taggaacaaa cccgtaccca taaacccatt gggtacagat ttatgcccgt    7020
taacaaaccc atgggtatga aaattgaccc aaacctatac cctaatgggg taaaaaccca    7080
tcgggtttcg gatttcgggt acccattgcc atctctagac aggacaacct cggccggtcc    7140
tgtatgtagg ccaccagcat cggccagttg gtacatccag ccggggtcag gtcacttta    7200 ctcgtctcaa tcagacaatc accgtccacc aacgaacgcc aacgttgtca cttgtcaggt    7260
cggttgagac ttgtattttt ttttgtcctc cgtaaaaatc ggttcaccag             7310
```

<210> SEQ ID NO 7
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (3)..(22)
<223> OTHER INFORMATION: n is absent or is a, c, g, or t

<400> SEQUENCE: 7

```
aannnnnnnn nnnnnnnnnn nnac                                             24
```

```
<210> SEQ ID NO 8
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (8)..(17)
<223> OTHER INFORMATION: n is absent or is a, c, g, or t

<400> SEQUENCE: 8
aatcatgnnn nnnnnnnttt aaac                                          24

<210> SEQ ID NO 9
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (10)..(15)
<223> OTHER INFORMATION: n is absent or is a, c, g, or t

<400> SEQUENCE: 9
aatcatgtcn nnnnnagttt aaac                                          24

<210> SEQ ID NO 10
<211> LENGTH: 16
<212> TYPE: DNA
<213> ORGANISM: Artificial
<220> FEATURE:
<223> OTHER INFORMATION: synthetic

<400> SEQUENCE: 10
aatcatgtgt ttaaac                                                   16

<210> SEQ ID NO 11
<211> LENGTH: 16
<212> TYPE: DNA
<213> ORGANISM: Artificial
<220> FEATURE:
<223> OTHER INFORMATION: synthetic

<400> SEQUENCE: 11
aatcatgagt ttaaac                                                   16

<210> SEQ ID NO 12
<211> LENGTH: 16
<212> TYPE: DNA
<213> ORGANISM: Artificial
<220> FEATURE:
<223> OTHER INFORMATION: synthetic

<400> SEQUENCE: 12
aatcatgtct ttaaac                                                   16

<210> SEQ ID NO 13
<211> LENGTH: 14
<212> TYPE: DNA
<213> ORGANISM: Artificial
<220> FEATURE:
<223> OTHER INFORMATION: synthetic

<400> SEQUENCE: 13
```

```
aatcatgttt aaac                                               14

<210> SEQ ID NO 14
<211> LENGTH: 14
<212> TYPE: DNA
<213> ORGANISM: Artificial
<220> FEATURE:
<223> OTHER INFORMATION: synthetic

<400> SEQUENCE: 14
aatcaagttt aaac                                               14

<210> SEQ ID NO 15
<211> LENGTH: 14
<212> TYPE: DNA
<213> ORGANISM: Artificial
<220> FEATURE:
<223> OTHER INFORMATION: synthetic

<400> SEQUENCE: 15
aatcatgtct aaac                                               14

<210> SEQ ID NO 16
<211> LENGTH: 18
<212> TYPE: DNA
<213> ORGANISM: Artificial
<220> FEATURE:
<223> OTHER INFORMATION: synthetic

<400> SEQUENCE: 16
aatcatgtca gtttaaac                                           18

<210> SEQ ID NO 17
<211> LENGTH: 18
<212> TYPE: DNA
<213> ORGANISM: Artificial
<220> FEATURE:
<223> OTHER INFORMATION: synthetic

<400> SEQUENCE: 17
aatcatgtta gtttaaac                                           18

<210> SEQ ID NO 18
<211> LENGTH: 18
<212> TYPE: DNA
<213> ORGANISM: Artificial
<220> FEATURE:
<223> OTHER INFORMATION: synthetic

<400> SEQUENCE: 18
aatcatgtca gtttaaac                                           18

<210> SEQ ID NO 19
<211> LENGTH: 24
<212> TYPE: DNA
<213> ORGANISM: Artificial
<220> FEATURE:
<223> OTHER INFORMATION: synthetic

<400> SEQUENCE: 19
aatcatgtca tagtttaaac tgaa                                    24

<210> SEQ ID NO 20
<211> LENGTH: 23
<212> TYPE: DNA
<213> ORGANISM: Artificial
```

```
<220> FEATURE:
<223> OTHER INFORMATION: synthetic

<400> SEQUENCE: 20
ccgccttcag tttaaactat cag                                              23

<210> SEQ ID NO 21
<211> LENGTH: 23
<212> TYPE: DNA
<213> ORGANISM: Artificial
<220> FEATURE:
<223> OTHER INFORMATION: synthetic

<400> SEQUENCE: 21
catcattggt gtcatcagtt ttt                                              23

<210> SEQ ID NO 22
<211> LENGTH: 23
<212> TYPE: DNA
<213> ORGANISM: Artificial
<220> FEATURE:
<223> OTHER INFORMATION: synthetic

<400> SEQUENCE: 22
agtgaatcat gtcactgata gtt                                              23

<210> SEQ ID NO 23
<211> LENGTH: 23
<212> TYPE: DNA
<213> ORGANISM: Artificial
<220> FEATURE:
<223> OTHER INFORMATION: synthetic

<400> SEQUENCE: 23
taattcctaa aaccaaaatc cag                                              23

<210> SEQ ID NO 24
<211> LENGTH: 23
<212> TYPE: DNA
<213> ORGANISM: Artificial
<220> FEATURE:
<223> OTHER INFORMATION: synthetic

<400> SEQUENCE: 24
ttgccaaatg tttgaacgat ctg                                              23

<210> SEQ ID NO 25
<211> LENGTH: 29
<212> TYPE: DNA
<213> ORGANISM: Artificial
<220> FEATURE:
<223> OTHER INFORMATION: synthetic

<400> SEQUENCE: 25
taaaaccaaa attcgttcaa acatttggc                                        29

<210> SEQ ID NO 26
<211> LENGTH: 26
<212> TYPE: DNA
<213> ORGANISM: Artificial
<220> FEATURE:
<223> OTHER INFORMATION: synthetic

<400> SEQUENCE: 26
tttaatgtac tgaattgtct agaccc                                           26
```

<210> SEQ ID NO 27
<211> LENGTH: 27
<212> TYPE: DNA
<213> ORGANISM: Artificial
<220> FEATURE:
<223> OTHER INFORMATION: synthetic

<400> SEQUENCE: 27
tttatagatc atacaaaaag gcccagt                                       27

<210> SEQ ID NO 28
<211> LENGTH: 27
<212> TYPE: DNA
<213> ORGANISM: Artificial
<220> FEATURE:
<223> OTHER INFORMATION: synthetic

<400> SEQUENCE: 28
tttaatgtac tgaattgtct agacccg                                       27

<210> SEQ ID NO 29
<211> LENGTH: 7309
<212> TYPE: DNA
<213> ORGANISM: Artificial
<220> FEATURE:
<223> OTHER INFORMATION: synthetic

<400> SEQUENCE: 29
tcctgtgttg ttggaacaga cttctgtctc ttctggtgat cataaatatt taaatgaacc      60
agttgtgttg gaaatgttg tttcttttg tctctagact ggaaagcgga gttctcgtca      120
acacggttct ttcaactagg gatgaaagtg gtaatccgaa ttgttagtac aaatttaata     180
ttttaaaata gatatgtata aaattttatg ttgatctttt ttatgttatc aagcacatta     240
gtataaatta gtataaatat gaataaaata ttacataaaa tgttttatgt attatttggt     300
ccctacaaca taaatagttg aaaaaattac taaatttgtt ttcgaatcta tatcgaagtt     360
tatatctatt atttaagaaa aatataggat gaaaaggttt atcttttatg aatctttaca     420
agctggatct tataaacaag aaaataaatt tatattgtag attttatatc ctatttattc     480
gcaatcaaag aaaagcgact aaaaaactga ttaccgagta aatactgttt ccaaccgttt     540
tcgtccctac tatcaacgcc ttctcccaac cgcagtcgat ctgtccgtct gtatcaggcg     600
cagcggcacc cctgctgttc gactatctag accatagaat attttaggta taacataatt     660
ttagttccac gctagaacat tttagttaga ataataacaa gatttgctat tgatgtagga     720
ctcgcccgtc actgtctaaa aaagcattct gtcggtctta ttctttaggc atcagcgggt     780
gtactatctc atttttccta tcatattcct cagtactctg ttaagtataa atggtctatt     840
ttacatgatg aactaataaa actaattaag gatcctaact ttttgtgaag gtaatttgga     900
tcattatgca ttaccatcct acgtatacct gctgcagcag catctgcgta agcacagcct     960
agatatatgc ttctgtgtgg actgaaagga ctttgtttt atcaattagt atactcccaa     1020
aaaactgatg acaccaatga tgcaaatagg ctgggaatag tctgtctaat agtttgagtg     1080
aatcatgtca ctgattaaac tgaaggcggg aaacgacaat ctgatcatga gcggagaatt     1140
aagggagtca cgttatgacc cccgccgatg acgcgggaca agccgtttta cgtttggaac     1200
tgacagaacc gcaacgttga aggagccact cagcaagctg gtacaagctt gcatgcctgc     1260
agtgcagcgt gacccggtcg tgcccctctc tagagataat gagcattgca tgtctaagtt     1320
ataaaaaatt accacatatt ttttttgtca cacttgtttg aagtgcagtt tatctatctt     1380

```
tatacatata tttaaacttt actctacgaa taatataatc tatagtacta caataatatc    1440
agtgttttag agaatcatat aaatgaacag ttagacatgg tctaaaggac aattgagtat    1500
tttgacaaca ggactctaca gttttatctt tttagtgtgc atgtgttctc ctttttttt    1560 gcaaatagct tcacctatat aatacttcat ccattttatt agtacatcca tttagggttt    1620
agggttaatg gttttatag actaattttt ttagtacatc tattttattc tattttagcc    1680
tctaaattaa gaaaactaaa actctatttt agttttttta tttaataatt tagatataaa    1740
atagaataaa ataaagtgac taaaaattaa acaaatacc tttaagaaat taaaaaaact    1800
aaggaaacat ttttcttgtt tcgagtagat aatgccagcc tgttaaacgc cgtcgacgag    1860
tctaacggac accaaccagc gaaccagcag cgtcgcgtcg ggccaagcga agcagacggc    1920
acggcatctc tgtcgctgcc tctggacccc tctcgagagt tccgctccac cgttggactt    1980
gctccgctgt cggcatccag aaattgcgtg gcggagcggc agacgtgagc cggcacggca    2040
ggcggcctcc tcctcctctc acggcaccgg cagctacggg ggattccttt cccaccgctc    2100
cttcgctttc ccttcctcgc ccgccgtaat aaatagacac cccctccaca ccctctttcc    2160
ccaacctcgt gttgttcgga gcgcacacac acacaaccag atctccccca aatccacccg    2220
tcggcacctc cgcttcaagg tacgccgctc gtcctccccc cccccccctc tctaccttct    2280
ctagatcggc gttccggtcc atggttaggg cccggtagtt ctacttctgt tcatgtttgt    2340
gttagatccg tgtttgtgtt agatccgtgc tgctagcgtt cgtacacgga tgcgacctgt    2400
acgtcagaca cgttctgatt gctaacttgc cagtgtttct cttggggaa tcctgggatg    2460 gctctagccg ttccgcagac gggatcgatt tcatgatttt ttttgtttcg ttgcataggg    2520
tttggtttgc cctttccctt tatttcaata tatgccgtgc acttgtttgt cgggtcatct    2580
tttcatgctt ttttttgtct tggttgtgat gatgtggtct ggttgggcgg tcgttctaga    2640
tcggagtaga attctgtttc aaactacctg gtggatttat taattttgga tctgtatgtg    2700
tgtgccatac atattcatag ttacgaattg aagatgatgg atggaaatat cgatctagga    2760
taggtataca tgttgatgcg ggttttactg atgcatatac agagatgctt tttgttcgct    2820
tggttgtgat gatgtggtgt ggttgggcgg tcgttcattc gttctagatc ggagtagaat    2880
actgtttcaa actacctggt gtatttatta attttggaac tgtatgtgtg tgtcatacat    2940
cttcatagtt acgagtttaa gatggatgga aatatcgatc taggataggt atacatgttg    3000
atgtgggttt tactgatgca tatacatgat ggcatatgca gcatctattc atatgctcta    3060
accttgagta cctatctatt ataataaaca agtatgtttt ataattattt tgatcttgat    3120
atacttggat gatggcatat gcagcagcta tatgtggatt ttttagccc tgccttcata    3180 cgctatttat ttgcttggta ctgtttcttt tgtcgatgct cacctgttg tttggtgtta    3240 cttctgcagg tcgactctag aggatccacc atgaacaaga acaacaccaa gctgagcacc    3300
cgcgccctgc cgagcttcat cgactacttc aacggcatct acggcttcgc caccggcatc    3360
aaggacatca tgaacatgat cttcaagacc gacaccggcg gcgacctgac cctggacgag    3420
atcctgaaga accagcagct gctgaacgac atcagcggca agctggacgg cgtgaacggc    3480
agcctgaacg acctgatcgc ccagggcaac ctgaacaccg agctgagcaa ggagatcctt    3540
aagatcgcca acgagcagaa ccaggtgctg aacgacgtga acaacaagct ggacgccatc    3600
aacaccatgc tgcgcgtgta cctgccgaag atcaccagca tgctgagcga cgtgatgaag    3660
cagaactacg ccctgagcct gcagatcgag tacctgagca agcagctgca ggagatcagc    3720
```

```
gacaagctgg acatcatcaa cgtgaacgtc ctgatcaaca gcaccctgac cgagatcacc    3780
ccggcctacc agcgcatcaa gtacgtgaac gagaagttcg aagagctgac cttcgccacc    3840
gagaccagca gcaaggtgaa gaaggacggc agcccggccg acatcctgga cgagctgacc    3900
gagctgaccg agctggcgaa gagcgtgacc aagaacgacg tggacggctt cgagttctac    3960
ctgaacacct tccacgacgt gatggtgggc aacaacctgt tcggccgcag cgccctgaag    4020
accgccagcg agctgatcac caaggagaac gtgaagacca cgggcagcga ggtgggcaac    4080
gtgtacaact tcctgatcgt gctgaccgcc ctgcaggccc aggccttcct gaccctgacc    4140
acctgtcgca agctgctggg cctggccgac atcgactaca ccagcatcat gaacgagcac    4200
ttgaacaagg agaaggagga gttccgcgtg aacatcctgc cgaccctgag caacaccttc    4260
agcaacccga actacgccaa ggtgaagggc agcgacgagg acgccaagat gatcgtggag    4320
gctaagccgg gccacgcgtt gatcggcttc gagatcagca cgacagcat caccgtgctg    4380
aaggtgtacg aggccaagct gaagcagaac taccaggtgg acaaggacag cttgagcgag    4440
gtgatctacg cgacatgga caagctgctg tgtccggacc agagcgagca aatctactac    4500
accaacaaca tcgtgttccc gaacgagtac gtgatcacca agatcgactt caccaagaag    4560
atgaagaccc tgcgctacga ggtgaccgcc aacttctacg acagcagcac cggcgagatc    4620
gacctgaaca agaagaaggt ggagagcagc gaggccgagt accgcaccct gagcgcgaac    4680
gacgacggcg tctacatgcc actgggcgtg atcagcgaga ccttcctgac cccgatcaac    4740
ggctttggcc tgcaggccga cgagaacagc cgcctgatca ccctgaccctg taagagctac    4800
ctgcgcgagc tgctgctagc caccgacctg agcaacaagg agaccaagct gatcgtgcca    4860
ccgagcggct tcatcagcaa catcgtggag aacggcagca tcgaggagga caacctggag    4920
ccgtggaagg ccaacaacaa gaacgcctac gtggaccaca ccggcggcgt gaacggcacc    4980
aaggccctgt acgtgcacaa ggacggcggc atcagccagt tcatcggcga caagctgaag    5040
ccgaagaccg agtacgtgat ccagtacacc gtgaagggca gccatcgat tcacctgaag    5100
gacgagaaca ccggctacat ccactacgag gacaccaaca caacctgga ggactaccag    5160
accatcaaca agcgcttcac caccggcacc gacctgaagg gcgtgtacct gatcctgaag    5220
agccagaacg gcgacgaggc ctggggcgac aacttcatca tcctggagat cagcccgagc    5280
gagaagctgc tgagcccgga gctgatcaac accaacaact ggaccagcac cggcagcacc    5340
aacatcagcg gcaacaccct gaccctgtac cagggcggcc gcggcatcct gaagcagaac    5400
ctgcagctgg acagcttcag cacctaccgc gtgtacttca gcgtgagcgg cgacgccaac    5460
gtgcgcatcc gcaactcccg cgaggtgctg ttcgagaaga ggtacatgag cggcgccaag    5520
gacgtgagcg agatgttcac caccaagttc gagaaggaca acttctacat cgagctgagc    5580
cagggcaaca acctgtacgg cggcccgatc gtgcacttct acgacgtgag catcaagtag    5640
gagctctaga tctgttctgc acaaagtgga gtagtcagtc atcgatcagg aaccagacac    5700
cagactttta ttcatacagt gaagtgaagt gaagtgcagt gcagtgagtt gctggttttt    5760
gtacaactta gtatgtattt gtatttgtaa aatacttcta tcaataaaat ttctaattcc    5820
taaaaccaaa attcgttcaa acatttggca ataaagtttc ttaagattga atcctgttgc    5880
cggtcttgcg atgattatca tataatttct gttgaattac gttaagcatg taataattaa    5940
catgtaatgc atgacgttat ttatgagatg gttttttatg attagagtcc cgcaattata    6000
catttaatac gcgatagaaa acaaaatata gcgcgcaaac taggataaat tatcgcgcgc    6060
ggtgtcatct atgttactag atccccgggt ctagacaatt cagtacatta aaaacgtccg    6120
```

```
ccatggtctg aaggcaacag ataaggcata ctgggccttg tggtagttgt tttactgggc    6180 cttttttgtat gatctataaa attcactggg atcaacccgg agaggaatgg cagcagatgc   6240
agtccccagg gtcctccgtc gccgcctgag cacccggcac ccgcgctgaa ccggagaggg    6300
acgcgcggac gccgtgcagc tggtgcggag ggggctgtgg cagatgagga tgagacgcgt    6360
acgtggctgg gaaggccagc aggccaccgg gtcttcgtcc agcccggcgc gagtggacag    6420
gactagagat ggcaacggtt acaaacccgc tgggttttac cgtcccaaac ccgtacccgt    6480
gaaaaatatc tatgcccatt aaaaaacccg tacccatgac gggtttgaga ttttgcccaa    6540
acccgtaccc atcgggttaa cgggtaccca tgggttaccc gcgggtttca tctccaatat    6600
acctgttctt ctcataatca ataagtatcg taatgattaa tgatatcatg atccaaaatc    6660
tatgtaatga acaacgagtt catgatttgg tataaaaatt attagtagag agaatgaaat    6720
acaaataata agttgtataa ttaagtgacc ttgcactaag ttatccatcc atcacatata    6780
taacgctagt aaaaactata atatcaagca agcaacactc tcaccgacta ctgatacatt    6840
caccaattga taaaaaatat gaagtaaata aggaataaca agtttgttgt tcgtttataa    6900
aataaaatga caatatgcac taggtttggt cgggtttaaa aaacccacgg gttcacgggt    6960
ttgggtacta taggaacaaa cccgtaccca taaacccatt gggtacagat ttatgcccgt    7020
taacaaaccc atgggtatga aaattgaccc aaacctatac cctaatgggg taaaaaccca    7080
tcgggtttcg gatttcgggt acccattgcc atctctagac aggacaacct cggccggtcc    7140
tgtatgtagg ccaccagcat cggccagttg gtacatccag ccggggtcag gtcacttttα    7200 ctcgtctcaa tcagacaatc accgtccacc aacgaacgcc aacgttgtca cttgtcaggt    7260
cggttgagac ttgtatttt ttttgtcctc cgtaaaaatc ggttcacca                 7309

<210> SEQ ID NO 30
<211> LENGTH: 27
<212> TYPE: DNA
<213> ORGANISM: Artificial
<220> FEATURE:
<223> OTHER INFORMATION: synthetic

<400> SEQUENCE: 30
tttgcatcat tggtgtcatc agttttt                                          27

<210> SEQ ID NO 31
<211> LENGTH: 27
<212> TYPE: DNA
<213> ORGANISM: Artificial
<220> FEATURE:
<223> OTHER INFORMATION: synthetic

<400> SEQUENCE: 31
tttcccgcct tcagttaaa ctatcag                                           27

<210> SEQ ID NO 32
<211> LENGTH: 1243
<212> TYPE: DNA
<213> ORGANISM: Artificial
<220> FEATURE:
<223> OTHER INFORMATION: synthetic

<400> SEQUENCE: 32
tcgcaatcaa agaaaagcga ctaaaaaact gattaccgag taaatactgt ttccaaccgt      60
tttcgtccct actatcaacg ccttctccca accgcagtcg atctgtccgt ctgtatcagg     120
```

-continued

| | |
|---|---|
| cgcagcggca cccctgctgt tcgactatct agaccataga atattttagg tatacaataa | 180 |
| ttttagttcc acgctagaac attttagtta gaataataac aagatttgct attgatgtag | 240 |
| gactcgcccg tcactgtcta aaaaagcatt ctgtcggtct tattctttag gcatcagcgg | 300 |
| gtgtactatc tcattttttcc tatcatattc ctcagtactc tgttaagtat aaatggtcta | 360 |
| ttttacatga tgaactaata aaactaatta aggatcctaa cttttttgtga aggtaatttg | 420 |
| gatcattatg cattaccatc ctacgtatac ctgctgcagc agcatctgcg taagcacagc | 480 |
| ctagatatat gcttctgtgt ggactgaaag gagactttgt ttatcaatta gtatactccc | 540 |
| aaaaaactga tgcaccaat gatgcaaata ggctgggaat agtctgtcta atagtttgag | 600 |
| tgaatcatgt cactgattta tagatcatac aaaaaggccc agttagttta aactgaaggc | 660 |
| gggaaacgac aatctgatca tgagcggaga attaagggag tcacgttatg accccgccg | 720 |
| atgacgcggg acaagccgtt ttacgtttgg aactgacaga accgcaacgt tgaaggagcc | 780 |
| actcagcaag ctggtacaag cttgcatgcc tgcagtgcag cgtgacccgg tcgtgcccct | 840 |
| ctctagagat aatgagcatt gcatgtctaa gttataaaaa attaccacat attttttttg | 900 |
| tcacacttgt ttgaagtgca gtttatctat ctttatacat atatttaaac tttactctac | 960 |
| gaataatata atctatagta ctacaataat atcagtgttt tagagaatca tataaatgaa | 1020 |
| cagttagaca tggtctaaag gacaattgag tattttgaca acaggactct acagttttat | 1080 |
| cttttttagtg tgcatgtgtt ctccttttttt tttgcaaata gcttcaccta tataatactt | 1140 |
| catccatttt attagtacat ccatttaggg tttagggtta atggttttta tagactaatt | 1200 |
| tttttagtac atctatttta ttctatttta gcctctaaat taa | 1243 |

<210> SEQ ID NO 33
<211> LENGTH: 25
<212> TYPE: DNA
<213> ORGANISM: Artificial
<220> FEATURE:
<223> OTHER INFORMATION: synthetic

<400> SEQUENCE: 33
ttttatgtat tatttggtcc ctaca                              25

<210> SEQ ID NO 34
<211> LENGTH: 25
<212> TYPE: DNA
<213> ORGANISM: Artificial
<220> FEATURE:
<223> OTHER INFORMATION: synthetic

<400> SEQUENCE: 34
gtcgacggcg tttaacaggc tggca                              25

<210> SEQ ID NO 35
<211> LENGTH: 25
<212> TYPE: DNA
<213> ORGANISM: Artificial
<220> FEATURE:
<223> OTHER INFORMATION: synthetic

<400> SEQUENCE: 35
ggcaacaacc tgtacggcgg cccga                              25

<210> SEQ ID NO 36
<211> LENGTH: 25
<212> TYPE: DNA
<213> ORGANISM: Artificial

```
<220> FEATURE:
<223> OTHER INFORMATION: synthetic

<400> SEQUENCE: 36
gttgccttca gaccatggcg gacgt                                              25

<210> SEQ ID NO 37
<211> LENGTH: 47
<212> TYPE: DNA
<213> ORGANISM: Artificial
<220> FEATURE:
<223> OTHER INFORMATION: synthetic

<400> SEQUENCE: 37
atgtcactga tttatagatc atacaaaaag gcccagttag tttaaac                      47

<210> SEQ ID NO 38
<211> LENGTH: 1307
<212> TYPE: PRT
<213> ORGANISM: Unknown
<220> FEATURE:
<223> OTHER INFORMATION: Acidaminococcus sp.

<400> SEQUENCE: 38
```

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

```
Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
        290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
        370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685
```

```
Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
                820                 825                 830

Arg Leu Ser His Asp Leu Ser Asp Glu Ala Arg Ala Leu Leu Pro Asn
                835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
                915                 920                 925

Gln Arg Ser Leu Asn Thr Ile Gln Gln Phe Asp Tyr Gln Lys Lys Leu
                930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
                980                 985                 990

Glu Asn Leu Asn Phe Gly Phe Lys Ser Lys Arg Thr Gly Ile Ala Glu
                995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
```

```
                  1100                1105                1110
Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 39
<211> LENGTH: 20
<212> TYPE: DNA
<213> ORGANISM: Artificial
<220> FEATURE:
<223> OTHER INFORMATION: synthetic

<400> SEQUENCE: 39
atgtcactga ttaaactgaa                                          20

<210> SEQ ID NO 40
<211> LENGTH: 40
<212> TYPE: DNA
<213> ORGANISM: Artificial
<220> FEATURE:
<223> OTHER INFORMATION: synthetic

<400> SEQUENCE: 40
tgagtgaatc atgtcactga ttaaactgaa ggcgggaaac                    40

<210> SEQ ID NO 41
<211> LENGTH: 20
<212> TYPE: DNA
<213> ORGANISM: Artificial
<220> FEATURE:
<223> OTHER INFORMATION: synthetic

<400> SEQUENCE: 41
cctaaaacca tcaaacattt                                          20

<210> SEQ ID NO 42
```

```
<211> LENGTH: 39
<212> TYPE: DNA
<213> ORGANISM: Artificial
<220> FEATURE:
<223> OTHER INFORMATION: synthetic

<400> SEQUENCE: 42
atttctaatt cctaaaacca tcaaacattt ggcaataaa                              39

<210> SEQ ID NO 43
<211> LENGTH: 7302
<212> TYPE: DNA
<213> ORGANISM: Artificial
<220> FEATURE:
<223> OTHER INFORMATION: synthetic

<400> SEQUENCE: 43
tcctgtgttg ttggaacaga cttctgtctc ttctggtgat cataaatatt taaatgaacc       60
agttgtgttg gaaatgttg ttttcttttg tctctagact ggaaagcgga gttctcgtca      120
acacggttct ttcaactagg gatgaaagtg gtaatccgaa ttgttagtac aaatttaata      180
ttttaaaata gatatgtata aaattttatg ttgatctttt ttatgttatc aagcacatta      240
gtataaatta gtataaatat gaataaaata ttacataaaa tgttttatgt attatttggt      300
ccctacaaca taaatagttg aaaaaattac taaatttgtt ttcgaatcta tatcgaagtt      360
tatatctatt atttaagaaa aatataggat gaaaaggttt atcttttatg aatctttaca      420
agctggatct tataaacaag aaaataaatt tatattgtag attttatatc ctatttattc      480
gcaatcaaag aaaagcgact aaaaaactga ttaccgagta aatactgttt ccaaccgttt      540
tcgtccctac tatcaacgcc ttctcccaac cgcagtcgat ctgtccgtct gtatcaggcg      600
cagcggcacc cctgctgttc gactatctag accatagaat attttaggta tacaataatt      660
ttagttccac gctagaacat tttagttaga ataataacaa gatttgctat tgatgtagga      720
ctcgcccgtc actgtctaaa aaagcattct gtcggtctta ttctttaggc atcagcgggt      780
gtactatctc atttttccta tcatattcct cagtactctg ttaagtataa atggtctatt      840
ttacatgatg aactaataaa actaattaag gatcctaact ttttgtgaag gtaatttgga      900
tcattatgca ttaccatcct acgtatacct gctgcagcag catctgcgta agcacagcct      960
agatatatgc ttctgtgtgg actgaaagga gactttgttt atcaattagt atactcccaa     1020
aaaactgatg acaccaatga tgcaaatagg ctgggaatag tctgtctaat agtttgagtg     1080
aatcatgtca ctgattaaac tgaaggcggg aaacgacaat ctgatcatga gcggagaatt     1140
aagggagtca cgttatgacc cccgccgatg acgcgggaca agccgtttta cgtttggaac     1200
tgacagaacc gcaacgttga aggagccact cagcaagctg gtacaagctt gcatgcctgc     1260
agtgcagcgt gacccggtcg tgcccctctc tagagataat gagcattgca tgtctaagtt     1320
ataaaaaatt accacatatt ttttttgtca cacttgtttg aagtgcagtt tatctatctt     1380
tatacatata tttaaacttt actctacgaa taatataatc tatagtacta caataatatc     1440
agtgttttag agaatcatat aaatgaacag ttagacatgg tctaaaggac aattgagtat     1500
tttgacaaca ggactctaca gttttatctt ttagtgtgc atgtgttctc ctttttttt      1560 gcaaatagct tcacctatat aatacttcat ccatttatt agtacatcca tttagggttt      1620
agggttaatg gtttttatag actaatttt ttagtacatc tatttattc tattttagcc       1680 tctaaattaa gaaaactaaa actctatttt agtttttta tttaataatt tagatataaa      1740
atagaataaa ataaagtgac taaaaattaa acaaataccc tttaagaaat taaaaaaact     1800
```

```
aaggaaacat ttttcttgtt tcgagtagat aatgccagcc tgttaaacgc cgtcgacgag   1860
tctaacggac accaaccagc gaaccagcag cgtcgcgtcg ggccaagcga agcagacggc   1920
acggcatctc tgtcgctgcc tctggacccc tctcgagagt tccgctccac cgttggactt   1980
gctccgctgt cggcatccag aaattgcgtg gcggagcggc agacgtgagc cggcacggca   2040
ggcggcctcc tcctcctctc acggcaccgg cagctacggg ggattccttt cccaccgctc   2100
cttcgctttc ccttcctcgc ccgccgtaat aaatagacac ccctccaca ccctctttcc    2160 ccaacctcgt gttgttcgga gcgcacacac acacaaccag atctccccca aatccacccg   2220
tcggcacctc cgcttcaagg tacgccgctc gtcctccccc cccccccctc tctaccttct   2280
ctagatcggc gttccggtcc atggttaggg cccggtagtt ctacttctgt tcatgtttgt   2340
gttagatccg tgtttgtgtt agatccgtgc tgctagcgtt cgtacacgga tgcgacctgt   2400
acgtcagaca cgttctgatt gctaacttgc cagtgtttct ctttgggaa tcctgggatg    2460 gctctagccg ttccgcagac gggatcgatt tcatgatttt ttttgtttcg ttgcataggg   2520
tttggtttgc ccttttcctt tatttcaata tatgccgtgc acttgtttgt cgggtcatct   2580
tttcatgctt tttttgtct tggttgtgat gatgtggtct ggttgggcgg tcgttctaga    2640
tcggagtaga attctgtttc aaactacctg gtggatttat taattttgga tctgtatgtg   2700
tgtgccatac atattcatag ttacgaattg aagatgatgg atggaaatat cgatctagga   2760
taggtataca tgttgatgcg ggttttactg atgcatatac agagatgctt tttgttcgct   2820
tggttgtgat gatgtggtgt ggttgggcgg tcgttcattc gttctagatc ggagtagaat   2880
actgtttcaa actacctggt gtatttatta attttggaac tgtatgtgtg tgtcatacat   2940
cttcatagtt acgagtttaa gatggatgga aatatcgatc taggataggt atacatgttg   3000
atgtgggttt tactgatgca tatacatgat ggcatatgca gcatctattc atatgctcta   3060
accttgagta cctatctatt ataataaaca agtatgtttt ataattattt tgatcttgat   3120
atacttggat gatggcatat gcagcagcta tatgtggatt tttttagccc tgccttcata   3180
cgctatttat ttgcttggta ctgtttcttt tgtcgatgct caccctgttg tttggtgtta   3240
cttctgcagg tcgactctag aggatccacc atgaacaaga caacaccaa gctgagcacc    3300 cgcgccctgc cgagcttcat cgactacttc aacggcatct acggcttcgc caccggcatc   3360
aaggacatca tgaacatgat cttcaagacc gacaccggcg cgacctgac cctggacgag    3420 atcctgaaga accagcagct gctgaacgac atcagcggca agctggacgg cgtgaacggc   3480
agcctgaacg acctgatcgc ccagggcaac ctgaacaccg agctgagcaa ggagatcctt   3540
aagatcgcca acgagcagaa ccaggtgctg aacgacgtga acaacaagct ggacgccatc   3600
aacaccatgc tgcgcgtgta cctgccgaag atcaccagca tgctgagcga cgtgatgaag   3660
cagaactacg ccctgagcct gcagatcgag tacctgagca agcagctgca ggagatcagc   3720
gacaagctgg acatcatcaa cgtgaacgtc ctgatcaaca gcaccctgac cgagatcacc   3780
ccggcctacc agcgcatcaa gtacgtgaac gagaagttcg aagagctgac cttcgccacc   3840
gagaccagca gcaaggtgaa gaaggacggc agcccggccg acatcctgga cgagctgacc   3900
gagctgaccg agctggcgaa gagcgtgacc aagaacgacg tggacggctt cgagttctac   3960
ctgaacacct tccacgacgt gatggtgggc aacaacctgt tcggccgcag cgccctgaag   4020
accgccagcg agctgatcac caaggagaac gtgaagacca cgcggcagcga ggtgggcaac   4080 gtgtacaact tcctgatcgt gctgaccgcc ctgcaggccc aggccttcct gaccctgacc   4140
```

```
acctgtcgca agctgctggg cctggccgac atcgactaca ccagcatcat gaacgagcac    4200
ttgaacaagg agaaggagga gttccgcgtg aacatcctgc cgaccctgag caacaccttc    4260
agcaacccga actacgccaa ggtgaagggc agcgacgagg acgccaagat gatcgtggag    4320
gctaagccgg ccacgcgtt gatcggcttc gagatcagca cgacagcat caccgtgctg     4380 aaggtgtacg aggccaagct gaagcagaac taccaggtgg acaaggacag cttgagcgag    4440
gtgatctacg cgacatgga caagctgctg tgtccggacc agagcgagca aatctactac     4500
accaacaaca tcgtgttccc gaacgagtac gtgatcacca agatcgactt caccaagaag    4560
atgaagaccc tgcgctacga ggtgaccgcc aacttctacg acagcagcac cggcgagatc    4620
gacctgaaca agaagaaggt ggagagcagc gaggccgagt accgcaccct gagcgcgaac    4680
gacgacggcg tctacatgcc actgggcgtg atcagcgaga ccttcctgac cccgatcaac    4740
ggctttggcc tgcaggccga cgagaacagc cgcctgatca ccctgacctg taagagctac    4800
ctgcgcgagc tgctgctagc caccgacctg agcaacaagg agaccaagct gatcgtgcca    4860
ccgagcggct tcatcagcaa catcgtggag aacggcagca tcgaggagga caacctggag    4920
ccgtggaagg ccaacaacaa gaacgcctac gtggaccaca ccggcggcgt gaacggcacc    4980
aaggccctgt acgtgcacaa ggacggcggc atcagccagt tcatcggcga caagctgaag    5040
ccgaagaccg agtacgtgat ccagtacacc gtgaagggca agccatcgat tcacctgaag    5100
gacgagaaca ccggctacat ccactacgag gacaccaaca caacctgga ggactaccag     5160 accatcaaca agcgcttcac caccggcacc gacctgaagg gcgtgtacct gatcctgaag    5220
agccagaacg cgacgaggc ctggggcgac aacttcatca tcctggagat cagcccgagc     5280
gagaagctgc tgagcccgga gctgatcaac accaacaact ggaccagcac cggcagcacc    5340
aacatcagcg gcaacaccct gaccctgtac cagggcggcc gcggcatcct gaagcagaac    5400
ctgcagctgg acagcttcag cacctaccgc gtgtacttca gcgtgagcgg cgacgccaac    5460
gtgcgcatcc gcaactcccg cgaggtgctg ttcgagaaga ggtacatgag cggcgccaag    5520
gacgtgagcg agatgttcac caccaagttc gagaaggaca acttctacat cgagctgagc    5580
cagggcaaca acctgtacgg cggccccgatc gtgcacttct acgacgtgag catcaagtag    5640
gagctctaga tctgttctgc acaaagtgga gtagtcagtc atcgatcagg aaccagacac    5700 cagacttta ttcatacagt gaagtgaagt gaagtgcagt gcagtgagtt gctggttttt     5760
gtacaactta gtatgtattt gtatttgtaa atacttcta tcaataaaat ttctaattcc     5820
taaaaccatc aaacatttgg caataaagtt tcttaagatt gaatcctgtt gccggtcttg    5880
cgatgattat catataatt ctgttgaatt acgttaagca tgtaataatt aacatgtaat     5940
gcatgacgtt atttatgaga tgggtttta tgattagagt cccgcaatta tacatttaat     6000
acgcgataga aaacaaaata tagcgcgcaa actaggataa attatcgcgc gcggtgtcat    6060
ctatgttact agatccccgg gtctagacaa ttcagtacat taaaaacgtc cgccatggtc    6120
tgaaggcaac agataaggca tactgggcct tgtggtagtt gttttactgg gcctttttgt    6180
atgatctata aaattcactg ggatcaaccc ggagaggaat ggcagcagat gcagtcccca    6240
gggtcctccg tcgccgcctg agcacccggc accegcgctg aaccgagag ggacgcgcgg     6300 acgccgtgca gctggtgcgg aggggctgt ggcagatgag gatgagacgc gtacgtggct    6360
gggaaggcca gcaggccacc gggtcttcgt ccagcccggc gcgagtggac aggactagag    6420
atggcaacgg ttacaaaccc gctgggtttt accgtcccaa acccgtaccc gtgaaaaata    6480
tctatgccca ttaaaaaacc cgtacccatg acgggtttga gattttgccc aaacccgtac    6540
```

```
ccatcgggtt aacgggtacc catgggttac ccgcgggttt catctccaat atacctgttc    6600
ttctcataat caataagtat cgtaatgatt aatgatatca tgatccaaaa tctatgtaat    6660
gaacaacgag ttcatgattt ggtataaaaa ttattagtag agagaatgaa atacaaataa    6720
taagttgtat aattaagtga ccttgcacta agttatccat ccatcacata tataacgcta    6780
gtaaaaacta taatatcaag caagcaacac tctcaccgac tactgataca ttcaccaatt    6840
gataaaaaat atgaagtaaa taaggaataa caagtttgtt gttcgtttat aaaataaaat    6900
gacaatatgc actaggtttg gtcgggttta aaaaacccac gggttcacgg gtttgggtac    6960
tataggaaca aacccgtacc cataaaccca ttgggtacag atttatgccc gttaacaaac    7020
ccatgggtat gaaaattgac ccaaacctat accctaatgg ggtaaaaacc catcgggttt    7080
cggatttcgg gtacccattg ccatctctag acaggacaac ctcggccggt cctgtatgta    7140
ggccaccagc atcggccagt tggtacatcc agccggggtc aggtcacttt tactcgtctc    7200
aatcagacaa tcaccgtcca ccaacgaacg ccaacgttgt cacttgtcag gtcggttgag    7260
acttgtattt tttttgtcc tccgtaaaaa tcggttcacc ag                       7302
```

UNITED STATES PATENT AND TRADEMARK OFFICE
CERTIFICATE OF CORRECTION

PATENT NO. : 11,359,210 B2
APPLICATION NO. : 17/248936
DATED : June 14, 2022
INVENTOR(S) : Joshua L. Price et al.

It is certified that error appears in the above-identified patent and that said Letters Patent is hereby corrected as shown below:

In the Claims

In Claim 2, Column 125, Line 43:
DELETE: "original_MIR162"
INSERT: --original MIR162--

Signed and Sealed this
Nineteenth Day of July, 2022

Katherine Kelly Vidal
*Director of the United States Patent and Trademark Office*